US012697174B2

(12) United States Patent

Lindeman et al.

(10) Patent No.: US 12,697,174 B2
(45) Date of Patent: Aug. 4, 2026

(54) ROBOTIC HAND-HELD SURGICAL INSTRUMENT SYSTEMS WITH A VISUAL INDICATOR AND METHODS OF CONTROLLING THE SAME

(71) Applicant: MAKO Surgical Corp., Weston, FL (US)

(72) Inventors: Phillip Lindeman, Kalamazoo, MI (US); Dustin James Payne, Kalamazoo, MI (US); Jeffrey Timmer, Kalamazoo, MI (US); Nathaniel Abram Mishler, Middleville, MI (US)

(73) Assignee: MAKO Surgical Corp., Weston, FL (US)

( * ) Notice: Subject to any disclaimer, the term of this patent is extended or adjusted under 35 U.S.C. 154(b) by 782 days.

(21) Appl. No.: 17/759,927

(22) PCT Filed: Jan. 20, 2021

(86) PCT No.: PCT/US2021/014205

§ 371 (c)(1),
(2) Date: Aug. 2, 2022

(87) PCT Pub. No.: WO2021/158367

PCT Pub. Date: Aug. 12, 2021

(65) Prior Publication Data

US 2023/0068121 A1 Mar. 2, 2023

Related U.S. Application Data

(60) Provisional application No. 63/059,517, filed on Jul. 31, 2020, provisional application No. 62/970,074, filed on Feb. 4, 2020.

(51) Int. Cl.
*A61B 34/20* (2016.01)
*A61B 17/00* (2006.01)
(Continued)

(52) U.S. Cl.
CPC .............. *A61B 34/20* (2016.02); *A61B 17/15* (2013.01); *A61B 34/30* (2016.02); *A61B 50/13* (2016.02);
(Continued)

(58) Field of Classification Search
CPC ......... A61B 34/20; A61B 34/25; A61B 34/30; A61B 34/10; A61B 34/35; A61B 34/00;
(Continued)

(56) References Cited

U.S. PATENT DOCUMENTS 5,305,203 A 4/1994 Raab
5,411,514 A 5/1995 Fucci et al.
(Continued)

FOREIGN PATENT DOCUMENTS

DE 102011056927 A1 6/2013
EP 1103229 A2 5/2001
(Continued)

OTHER PUBLICATIONS

English language abstract and machine-assisted English translation for DE 10 2011 056 927 A1 extracted from espacenet.com database on Aug. 3, 2022, 19 pages.
(Continued)

*Primary Examiner* — Marcela I. Shirsat
(74) *Attorney, Agent, or Firm* — Howard & Howard Attorneys PLLC

(57) ABSTRACT

A system is provided comprising a robotic instrument for use with a surgical tool. In some versions, the robotic instrument comprises a hand-held portion to be held by a user and a tool support movably coupled to the hand-held portion to support the surgical tool. A plurality of actuators operatively interconnect the tool support and the hand-held portion to move the tool support in three degrees of freedom relative to the hand-held portion. An optional constraint
(Continued)

assembly may operatively interconnect the tool support and the hand-held portion to constrain movement of the tool support relative to the hand-held portion in three degrees of freedom. A visual indicator assists users in positioning hand-held portion of the instrument to maximize the useability of the system.

21 Claims, 41 Drawing Sheets

(51) Int. Cl.

| | |
|---|---|
| A61B 17/14 | (2006.01) |
| A61B 17/15 | (2006.01) |
| A61B 17/16 | (2006.01) |
| A61B 17/17 | (2006.01) |
| A61B 17/56 | (2006.01) |
| A61B 34/00 | (2016.01) |
| A61B 34/10 | (2016.01) |
| A61B 34/30 | (2016.01) |
| A61B 50/13 | (2016.01) |
| A61B 90/00 | (2016.01) |
| A61B 90/50 | (2016.01) |

(52) U.S. Cl.
CPC .............. *A61B 90/37* (2016.02); *A61B 90/50* (2016.02); *A61B 2017/00398* (2013.01); *A61B 2017/00477* (2013.01); *A61B 17/142* (2016.11); *A61B 17/1613* (2013.01); *A61B 17/1622* (2013.01); *A61B 17/1624* (2013.01); *A61B 17/1626* (2013.01); *A61B 17/1642* (2013.01); *A61B 17/1657* (2013.01); *A61B 17/1659* (2013.01); *A61B 17/1662* (2013.01); *A61B 17/1703* (2013.01); *A61B 17/1739* (2013.01); *A61B 17/1764* (2013.01); *A61B 2017/564* (2013.01); *A61B 34/10* (2016.02); *A61B 2034/107* (2016.02); *A61B 2034/108* (2016.02); *A61B 2034/2055* (2016.02); *A61B 34/25* (2016.02); *A61B 2090/3983* (2016.02)

(58) Field of Classification Search
CPC ....... A61B 17/142; A61B 17/15; A61B 17/14; A61B 17/17; A61B 17/1613; A61B 17/1622; A61B 17/1624; A61B 17/1626; A61B 17/16; A61B 17/1642; A61B 17/1657; A61B 17/1659; A61B 17/1662; A61B 17/1703; A61B 17/1739; A61B 17/1764; A61B 50/13; A61B 90/37; A61B 90/50; A61B 2017/564; A61B 2017/00398; A61B 2017/00477; A61B 2034/107; A61B 2034/2055; A61B 2034/108; A61B 2090/3983
See application file for complete search history.

(56) References Cited

U.S. PATENT DOCUMENTS

| | | | |
|---|---|---|---|
| 5,766,199 A | 6/1998 | Heisler et al. |
| 7,035,716 B2 | 4/2006 | Harris et al. |
| 7,302,288 B1 | 11/2007 | Schellengberg |
| 7,422,582 B2 | 9/2008 | Malackowski et al. |
| 7,660,623 B2 | 2/2010 | Hunter et al. |
| 8,388,541 B2 | 3/2013 | Messerly et al. |
| 8,560,047 B2 | 10/2013 | Haider et al. |
| 8,617,174 B2 | 12/2013 | Axelson, Jr. et al. |
| 8,734,432 B2 | 5/2014 | Tuma et al. |
| 8,858,455 B2 | 10/2014 | Rothenberg |
| 8,876,830 B2 | 11/2014 | Hodorek et al. |
| 8,898,043 B2 | 11/2014 | Ashby et al. |
| 8,903,546 B2 | 12/2014 | Diolaiti et al. |
| 9,008,757 B2 | 4/2015 | Wu |
| 9,060,794 B2 | 6/2015 | Kang et al. |
| 9,554,812 B2 | 1/2017 | Inkpen et al. |
| 9,707,043 B2 | 7/2017 | Bozung |
| 9,820,753 B2 | 11/2017 | Walen et al. |
| 10,070,849 B2 | 9/2018 | Marczyk |
| 10,080,617 B2 | 9/2018 | Haider et al. |
| 10,350,014 B2 | 7/2019 | Beelen et al. |
| 10,500,005 B2 | 12/2019 | Weir et al. |
| 10,687,823 B2 | 6/2020 | Mac an Tuile et al. |
| 11,185,378 B2 | 11/2021 | Weir et al. |
| 11,284,946 B2 | 3/2022 | Shalayev et al. |
| 11,389,304 B1 | 7/2022 | Nikou |
| 11,457,980 B2 | 10/2022 | Bonny et al. |
| 2005/0020909 A1 | 1/2005 | Moctezuma de la Barrera et al. |
| 2008/0027449 A1* | 1/2008 | Gundlapalli ........... A61B 17/14 606/82 |
| 2008/0302226 A1 | 12/2008 | Fischer |
| 2013/0060278 A1 | 3/2013 | Bozung et al. |
| 2013/0096574 A1* | 4/2013 | Kang ..................... A61B 34/30 606/130 |
| 2017/0007327 A1 | 1/2017 | Haider et al. |
| 2017/0156799 A1 | 6/2017 | Bozung |
| 2017/0281280 A1 | 10/2017 | Haider et al. |
| 2018/0055517 A1 | 3/2018 | Kang et al. |
| 2018/0142401 A1 | 5/2018 | Deshpande |
| 2018/0280159 A1 | 10/2018 | Hunter et al. |
| 2018/0333207 A1 | 11/2018 | Moctezuma De la Barrera |
| 2018/0344409 A1 | 12/2018 | Bonny et al. |
| 2018/0353245 A1 | 12/2018 | Mccloud et al. |
| 2019/0083179 A1 | 3/2019 | Kheradpir et al. |
| 2019/0090959 A1 | 3/2019 | Haider et al. |
| 2019/0223957 A1 | 7/2019 | Dekel et al. |
| 2019/0298404 A1 | 10/2019 | Stritch |
| 2020/0069373 A1 | 3/2020 | Yu et al. |
| 2020/0069377 A1 | 3/2020 | Finley et al. |
| 2020/0323540 A1 | 10/2020 | Kang et al. |
| 2022/0249107 A1 | 8/2022 | Bonny et al. |
| 2022/0265376 A1 | 8/2022 | Bonny et al. |
| 2022/0265377 A1 | 8/2022 | Bonny et al. |
| 2022/0273396 A1* | 9/2022 | Bozung ................. A61B 90/03 |
| 2022/0323162 A1 | 10/2022 | Bonny et al. |
| 2022/0323163 A1 | 10/2022 | Bonny et al. |
| 2023/0255701 A1* | 8/2023 | Post ....................... A61B 34/30 606/82 |

FOREIGN PATENT DOCUMENTS

| | | |
|---|---|---|
| EP | 2716252 B1 | 12/2015 |
| EP | 3007637 B1 | 11/2017 |
| WO | 2017091380 A1 | 6/2017 |
| WO | 2018104439 A1 | 6/2018 |
| WO | 2018175172 A1 | 9/2018 |
| WO | 2020236814 A1 | 11/2020 |
| WO | 2021011646 A2 | 1/2021 |
| WO | 2022055980 A1 | 3/2022 |

OTHER PUBLICATIONS

International Search Report for Application No. PCT/US2021/014205 dated May 10, 2021, 5 pages.
International Search Report for Application No. PCT/US2022/013108 dated Jun. 29, 2022, 2 pages.
Partal International Search Report for Application No. PCT/US2022/013108 dated May 2, 2022, 2 pages.

\* cited by examiner 500 500' 500"

502 502' 502"

600

602

Upper pitch
limit #1

Center of
pitch range of
motion

Actual
pitch

Lower pitch
limit #2

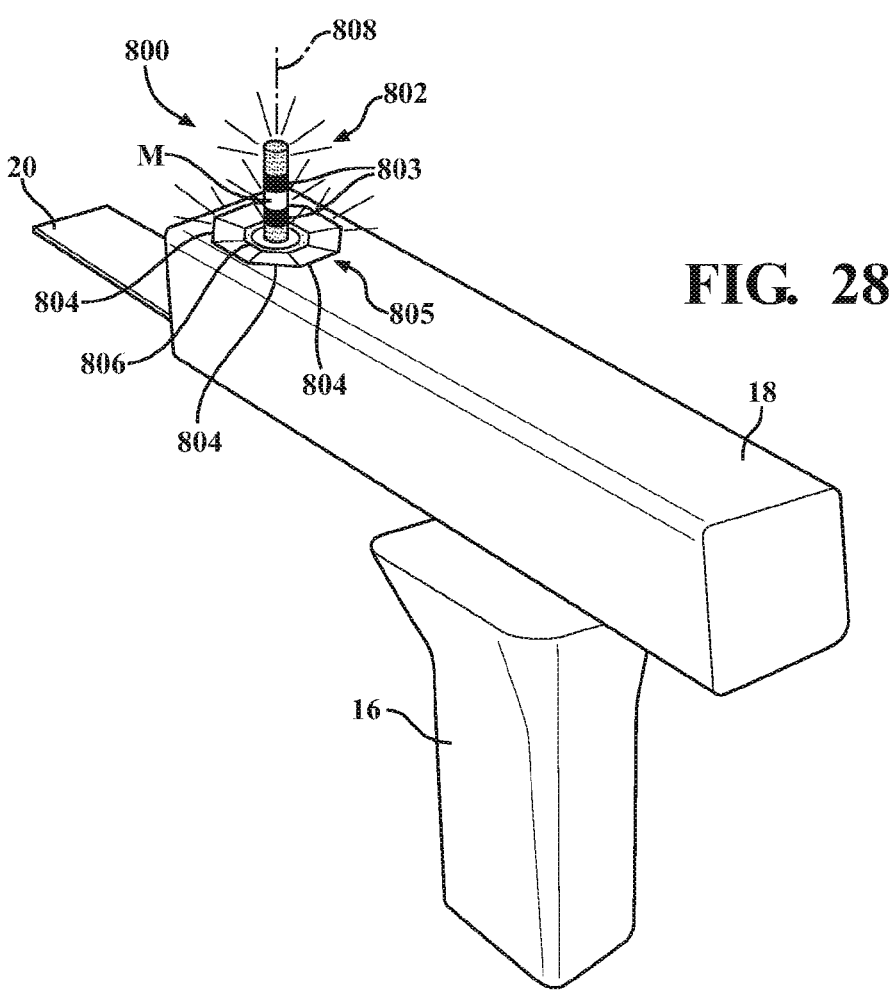
FIG. 28
FIG. 29A
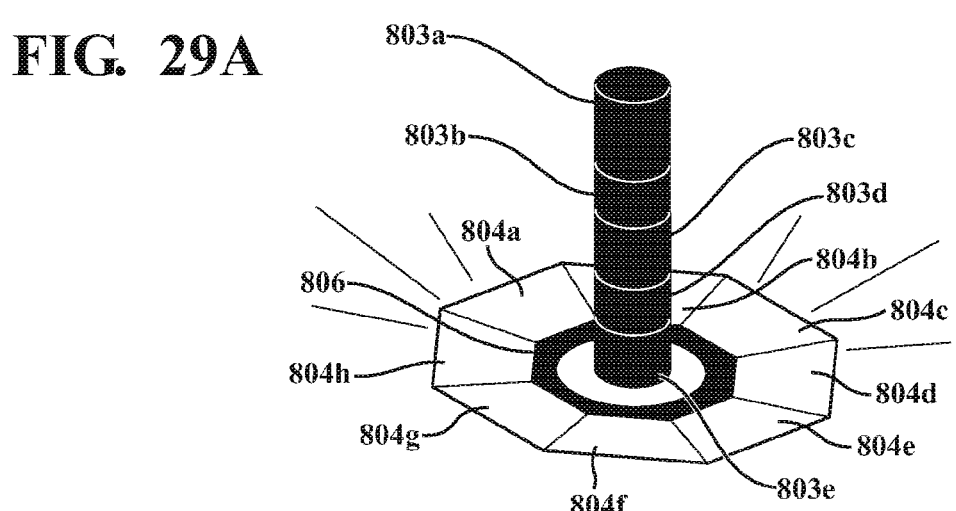

FIG. 31
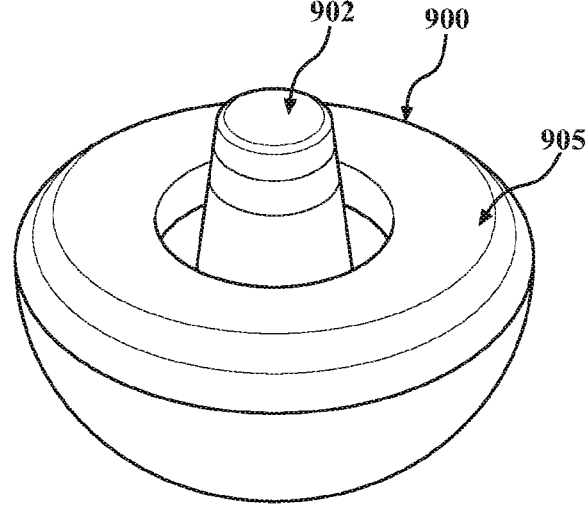
FIG. 32A
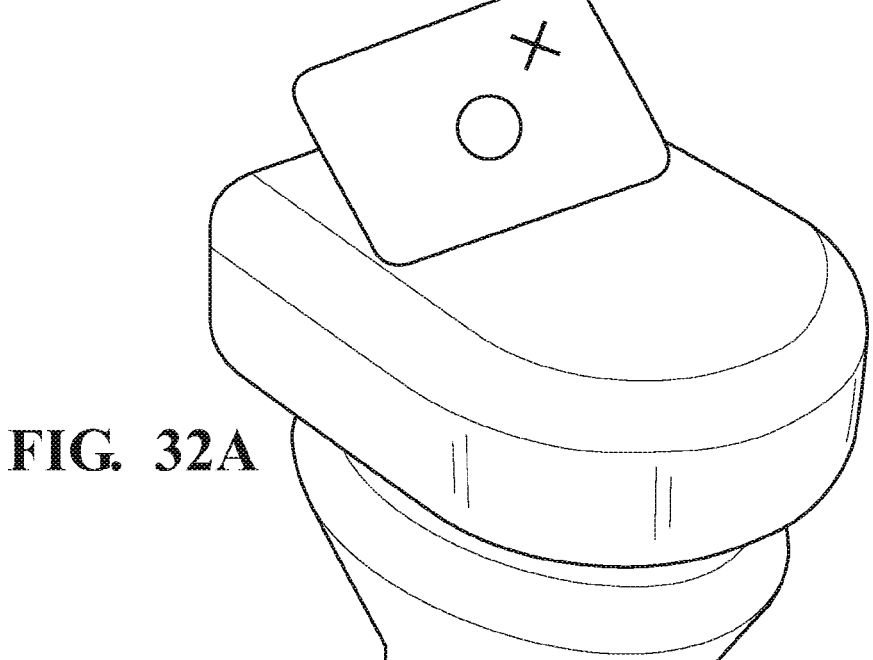
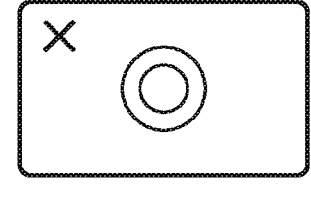
FIG. 32B
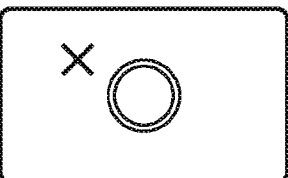
FIG. 32C

FIG. 35A
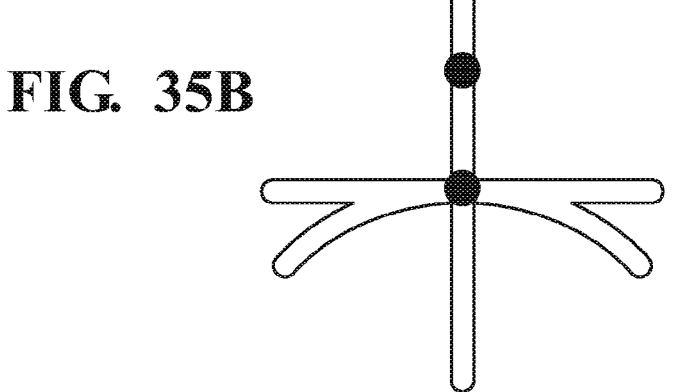
FIG. 35B
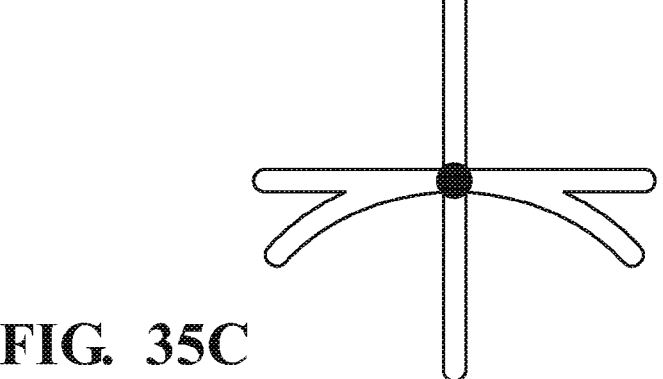
FIG. 35C

ROBOTIC HAND-HELD SURGICAL INSTRUMENT SYSTEMS WITH A VISUAL INDICATOR AND METHODS OF CONTROLLING THE SAME

The subject patent application is a national entry of International Application No. PCT/US2021/014205, filed Jan. 20, 2021, which claims priority to and all the benefits of U.S. Provisional Application No. 62/970,074, filed Feb. 4, 2020, and U.S. Provisional Application No. 63/059,517, filed Jul. 31, 2020 the entire contents of each are incorporated herein by reference.

TECHNICAL FIELD

The present disclosure relates generally to surgical robotic hand-held instrument systems and methods of use.

BACKGROUND

Physical cutting guides are used to constrain surgical tools when resecting tissue from a patient. In some cases, physical cutting guides constrain such surgical tools for the purpose of preparing joints to accept replacement implants. The time required to position and secure a physical cutting guide to the patient can represent a significant portion of the overall time required to perform a surgical procedure.

Navigation systems (also referred to as tracking systems) can be used to properly align and secure jigs, as well as track a position and/or orientation of a surgical tool used to resect tissue from a patient. Tracking systems typically employ one or more trackers associated with the tool and the tissue being resected. A display can then be viewed by a user to determine a current position of the tool relative to a desired cut path of tissue to be removed. The display may be arranged in a manner that requires the user to look away from the tissue and surgical site to visualize the tool's progress. This can distract the user from focusing on the surgical site. Also, it may be difficult for the user to place the tool in a desired manner.

Robotically assisted surgery typically relies on large robots with robotic arms that can move in six degrees of freedom (DOF). These large robots may be cumbersome to operate and maneuver in the operating room.

There is a need for systems and methods to address one or more of these challenges.

SUMMARY

One general aspect includes a hand-held robotic system for use with a surgical tool. The hand-held robotic system also includes an instrument that includes a hand-held portion to be held by a user and a tool support coupled to the hand-held portion. The tool support may include a tool drive motor to drive motion of the surgical tool and an actuator assembly operatively interconnecting the tool support and the hand-held portion to move the tool support to move the surgical tool in a plurality of degrees of freedom relative to the hand-held portion. The actuator assembly including a plurality of actuators. The system may also include a visual indicator to guide the user where to place the hand-held portion. The control system may be coupled to the plurality of actuators and the visual indicator, the control system being configured to determine a position and/or orientation of the hand-held portion in a first degree of freedom in a known coordinate system. The control system may also determine a range of motion of the tool support in a second degree of freedom based on the position and/or orientation of the hand-held portion in the first degree of freedom. The control system may also determine a position and/or orientation of the hand-held portion in the second degree of freedom in the known coordinate system. The control system may also control the visual indicator based on the position and/or orientation of the hand-held portion and the range of motion in the second degree of freedom.

Another general aspect includes a hand-held robotic system for use with a surgical tool. The hand-held robotic system also includes an instrument that includes a hand-held portion to be held by a user and a tool support coupled to the hand-held portion. The tool support may include a tool drive motor to drive motion of the surgical tool. The instrument may also include an actuator assembly operatively interconnecting the tool support and the hand-held portion to move the tool support to move the tool in a plurality of degrees of freedom relative to the hand-held portion, the actuator assembly including a plurality of actuators. The hand-held robotic system may also include a visual indicator to guide the user where to place the hand-held portion. The system may further include a control system coupled to the plurality of actuators and the visual indicator. The control system may be configured to determine a first pose of the hand-held portion in a known coordinate system. The control system may also be configured to determine a first range of motion in a first degree of freedom based on the first pose and determine a second pose of the hand-held portion in the known coordinate system. The control system may also determine a second range of motion in the first degree of freedom based on the second pose, where the first and second range of motion are different and the first and second poses are different. The control system may also determine a first position and/or orientation of the hand-held portion based on the first pose in the first degree of freedom and control the visual indicator based on the first position and/or orientation and the first range of motion, and determine a second position and/or orientation of the hand-held portion based on the second pose in the first degree of freedom and control the visual indicator based on second position and/or orientation and the second range of motion.

Another general aspect is a method of controlling a visual indicator of a hand-held robotic system for use with a saw blade. The robotic system may include a hand-held instrument having a hand-held portion to be held by a user and a blade support movably coupled to the hand-held portion to support the saw blade. The hand-held instrument may include an actuator assembly operatively interconnecting the blade support and the hand-held portion. The actuator assembly may include a plurality of actuators. The blade support may include a saw drive motor. The method may comprise the steps of determining a position and/or orientation of the hand-held portion in a first degree of freedom in a known coordinate system; determining a range of motion of the tool support in a second degree of freedom based on the position and/or orientation of the hand-held portion in the first degree of freedom in the known coordinate system. The method may also include determining a position and/or orientation of the hand-held portion in the second degree of freedom in the known coordinate system. The method may include controlling the visual indicator based on the position and/or orientation of the hand-held portion and the range of motion in the second degree of freedom.

Another general aspect is a hand-held robotic system for use with a tool. The system may include an instrument that features a hand-held portion to be held by a user and a tool support coupled to the hand-held portion. The tool support may include a tool drive motor to drive motion of the tool. The instrument may include an actuator assembly operatively interconnecting the tool support and the hand-held portion to move the tool support to move the tool in a plurality of degrees of freedom relative to the hand-held portion to align the tool. The actuator assembly including a plurality of actuators. The system may include a visual indicator to guide the user where to place the hand-held portion. The system may include a control system coupled to the plurality of actuators. The control system may be configured to determine a position and/or orientation of the hand-held portion in a first degree of freedom and a second degree of freedom in a known coordinate system. The control system may be configured to control the visual indicator based on the position and/or orientation of the hand-held portion in the first and second degrees of freedom and a range of motion of the tool support relative to the hand-held portion in the first and second degrees of freedom. A method is similarly contemplated.

A BRIEF DESCRIPTION OF THE DRAWINGS

Advantages of the present disclosure will be readily appreciated as the same becomes better understood by reference to the following detailed description when considered in connection with the accompanying drawings.

Figure 11:
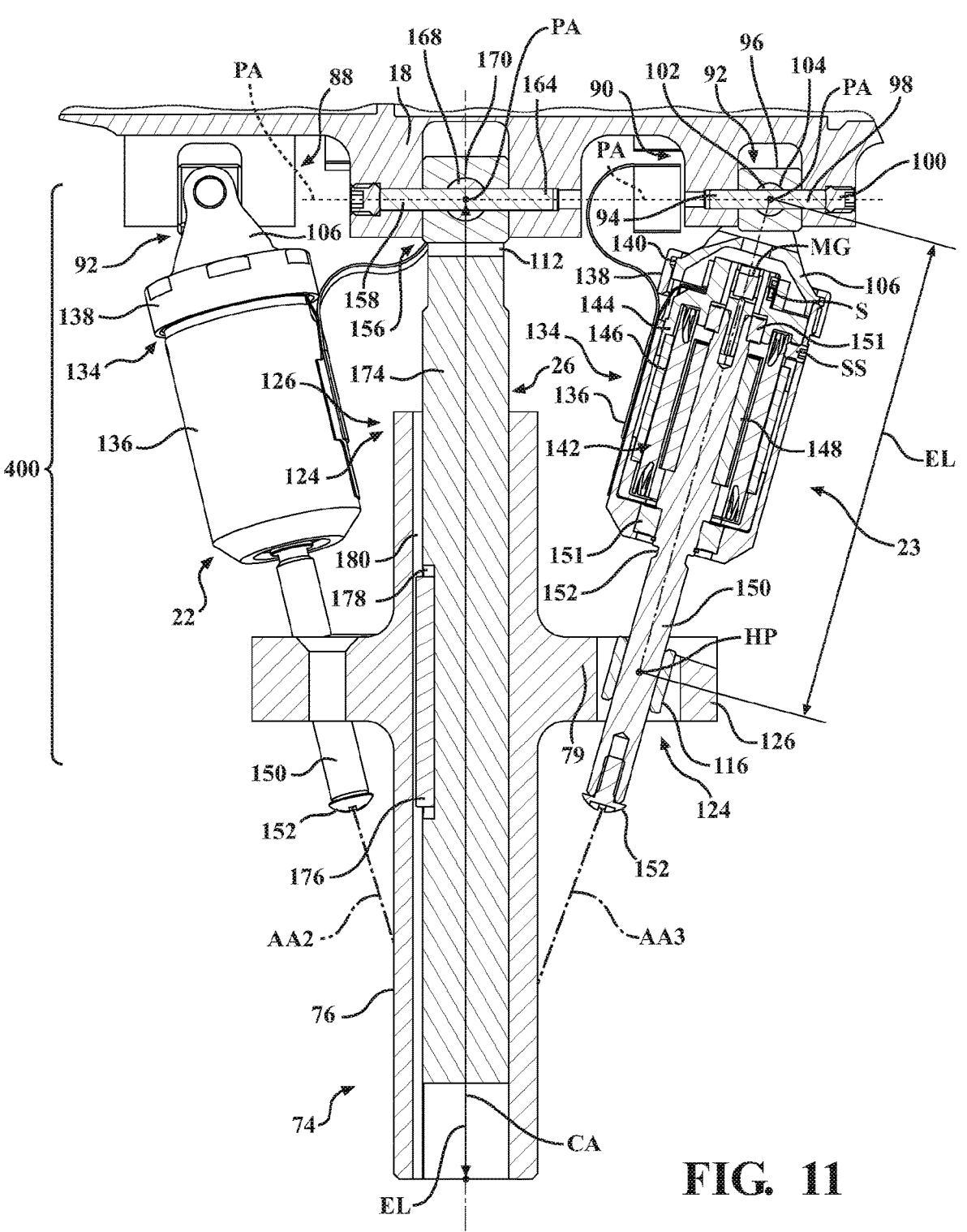

FIG. 11 a partial cross-sectional view of the robotic instrument

Figure 12:
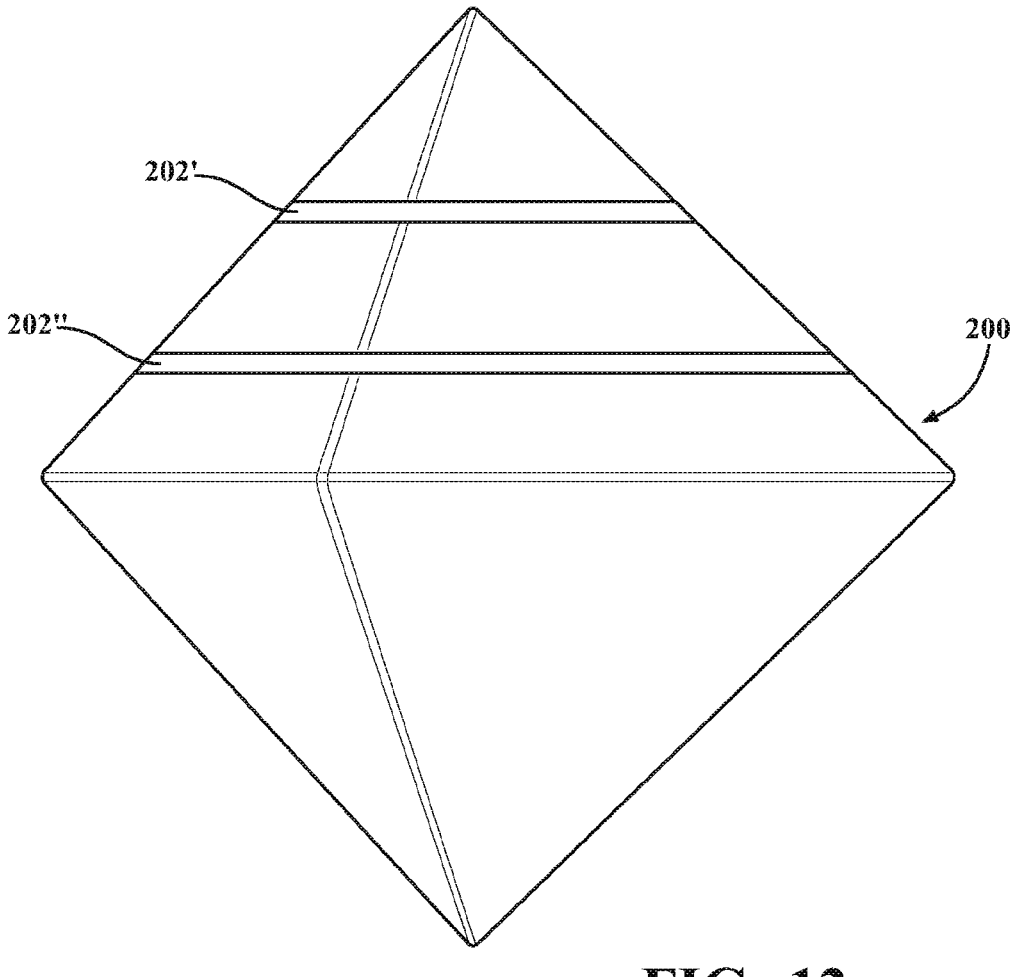

FIG. 12 illustrates a Cartesian model of a workspace of the robotic instrument.

Figure 13:
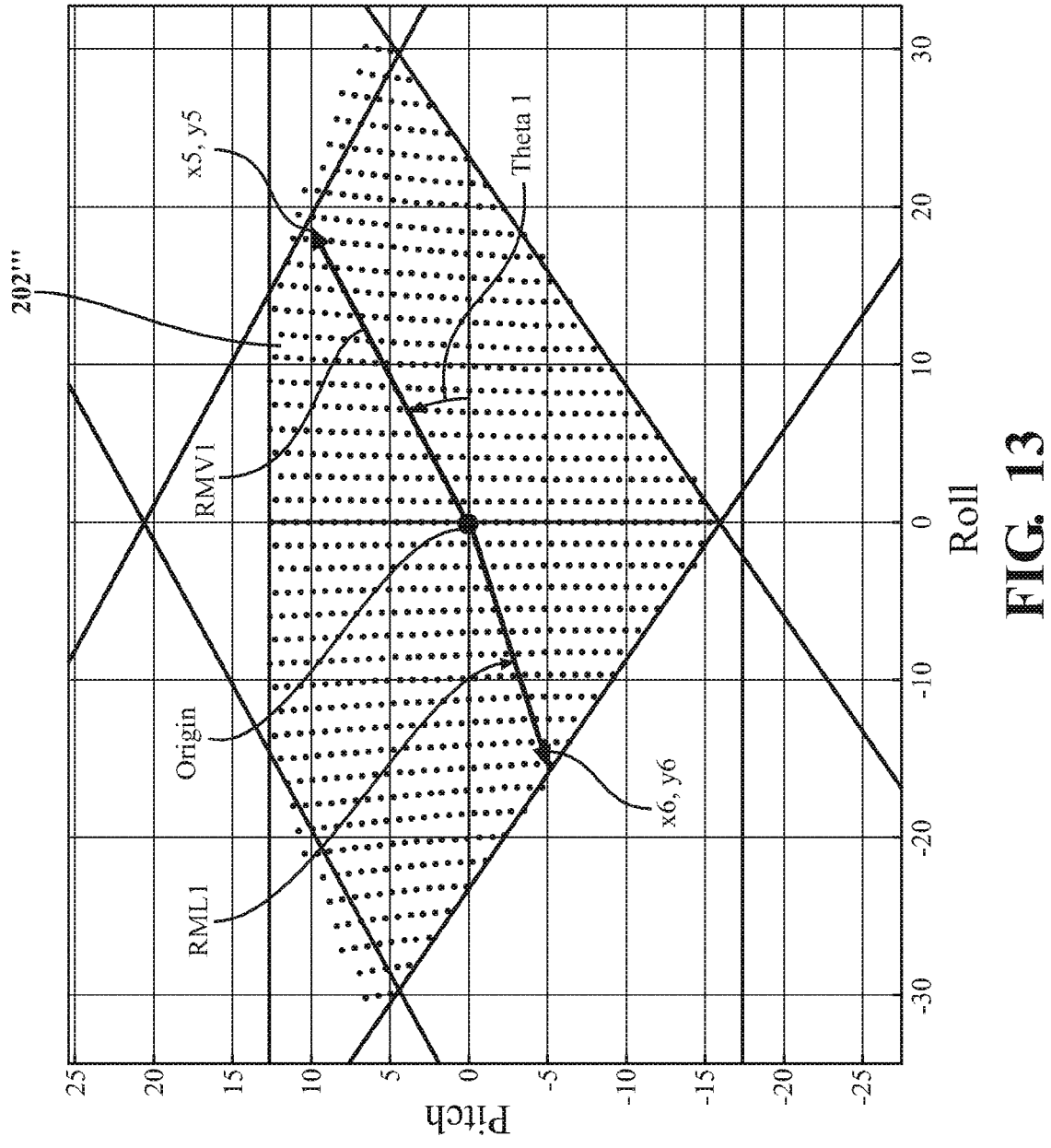

FIG. 13 illustrates a first two-dimensional slice region with a first range of motion vector.

Figure 14:
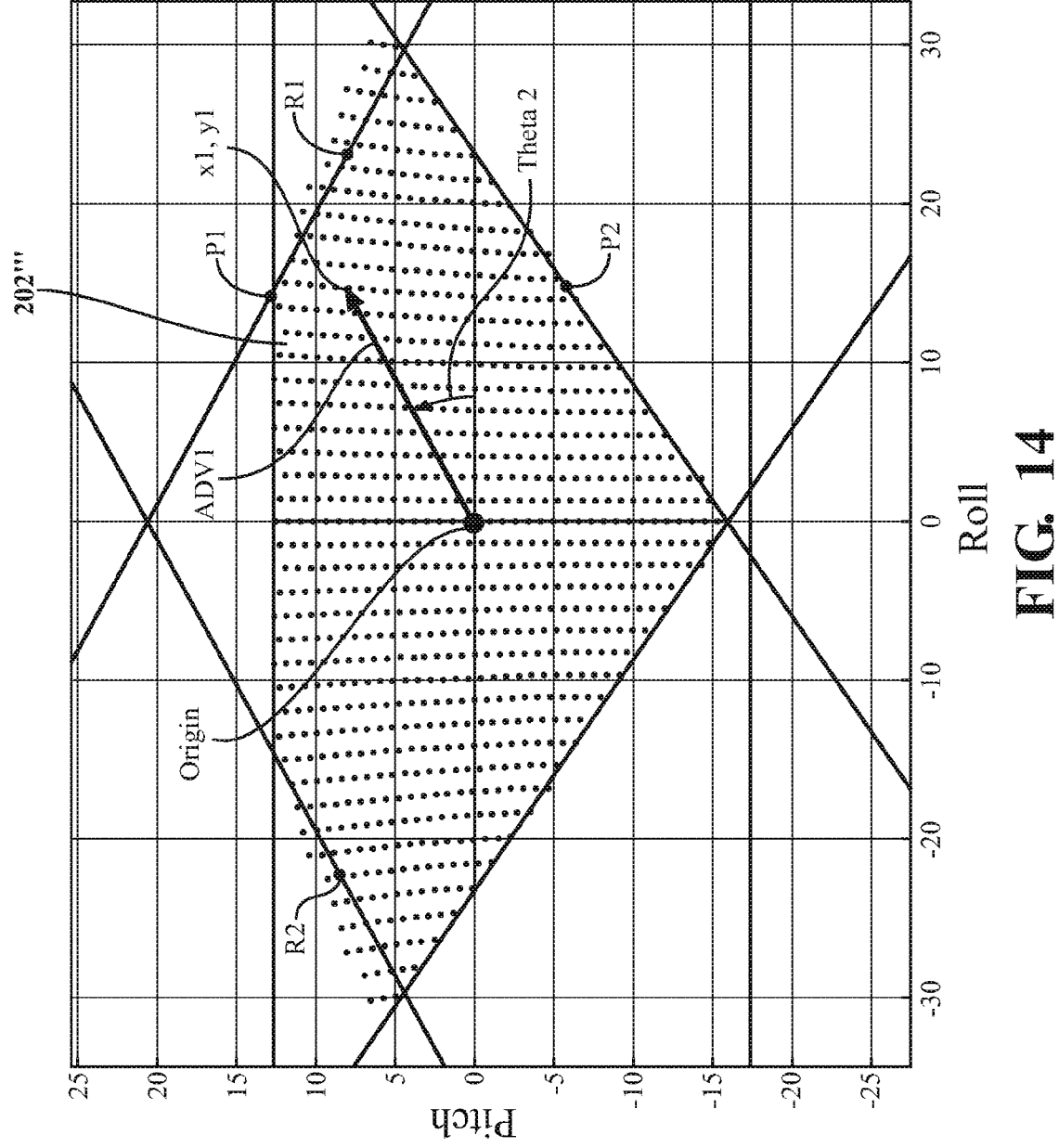

FIG. 14 illustrates the two-dimensional slice region of FIG. 13, with a first actual deviation vector.

Figure 15:
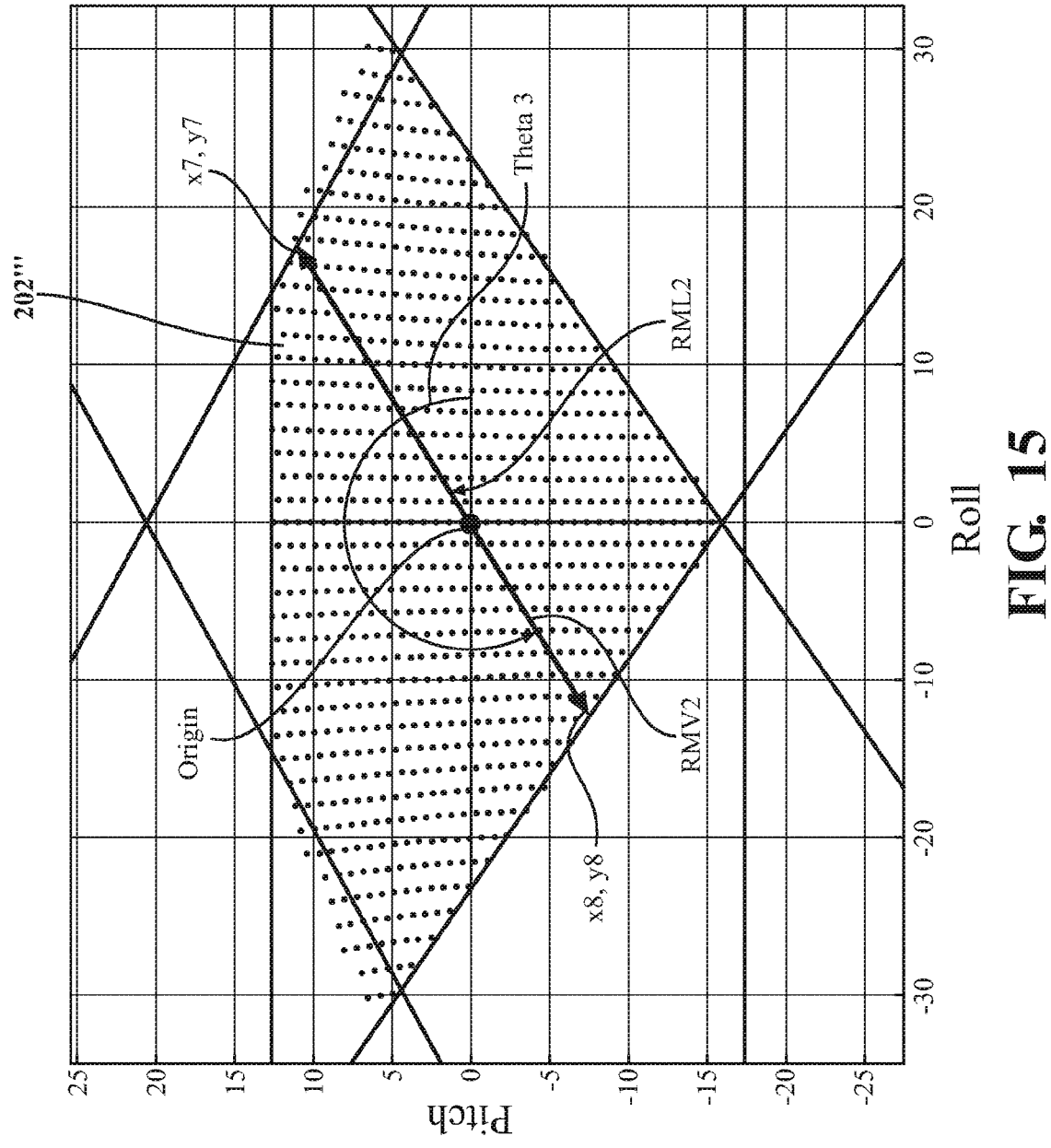

FIG. 15 illustrates the two-dimensional slice region of FIG. 13, with a second range of motion vector.

Figure 16:
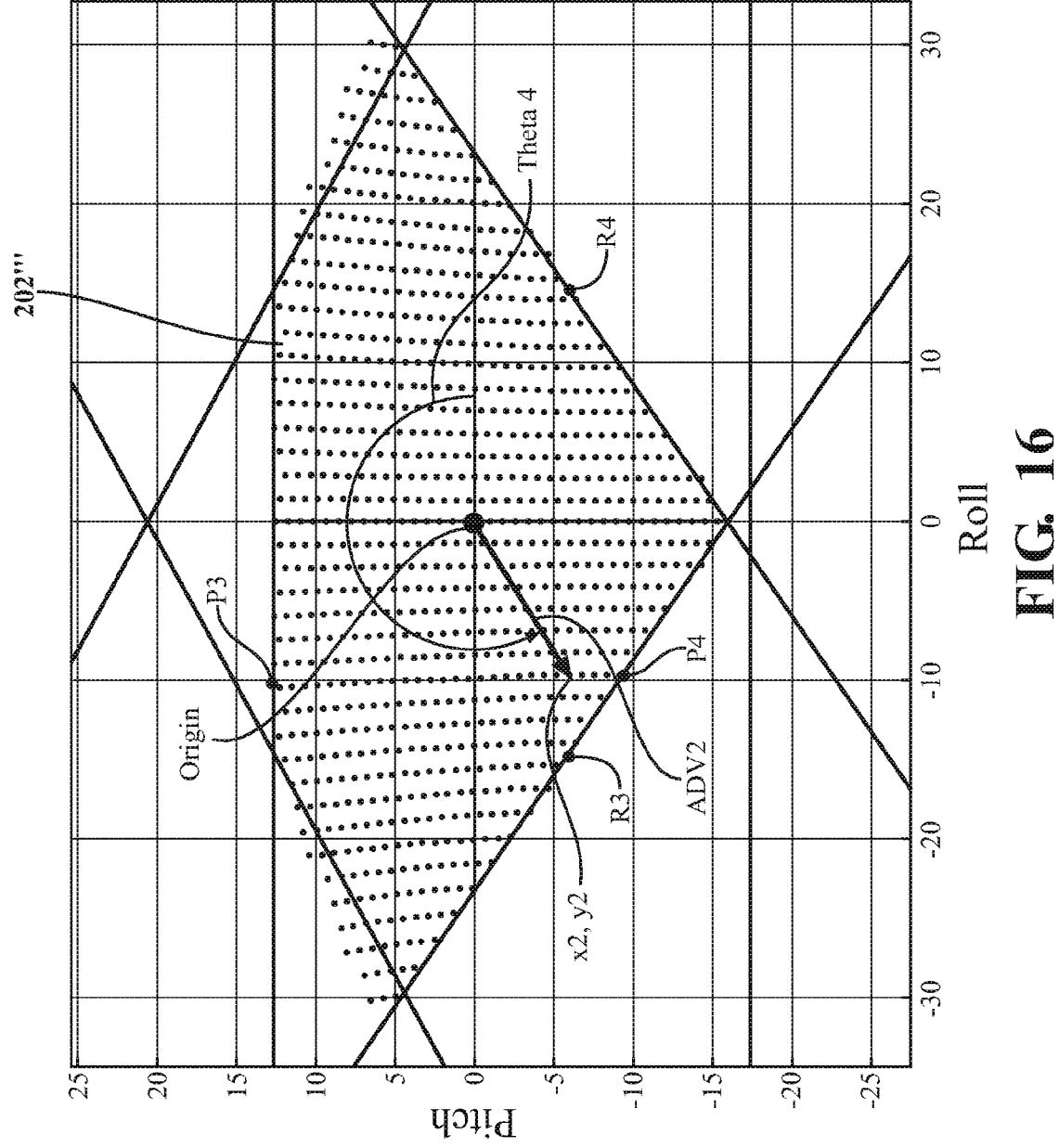

FIG. 16 illustrates the two-dimensional slice region of FIG. 15, with a second actual deviation vector.

Figure 17:
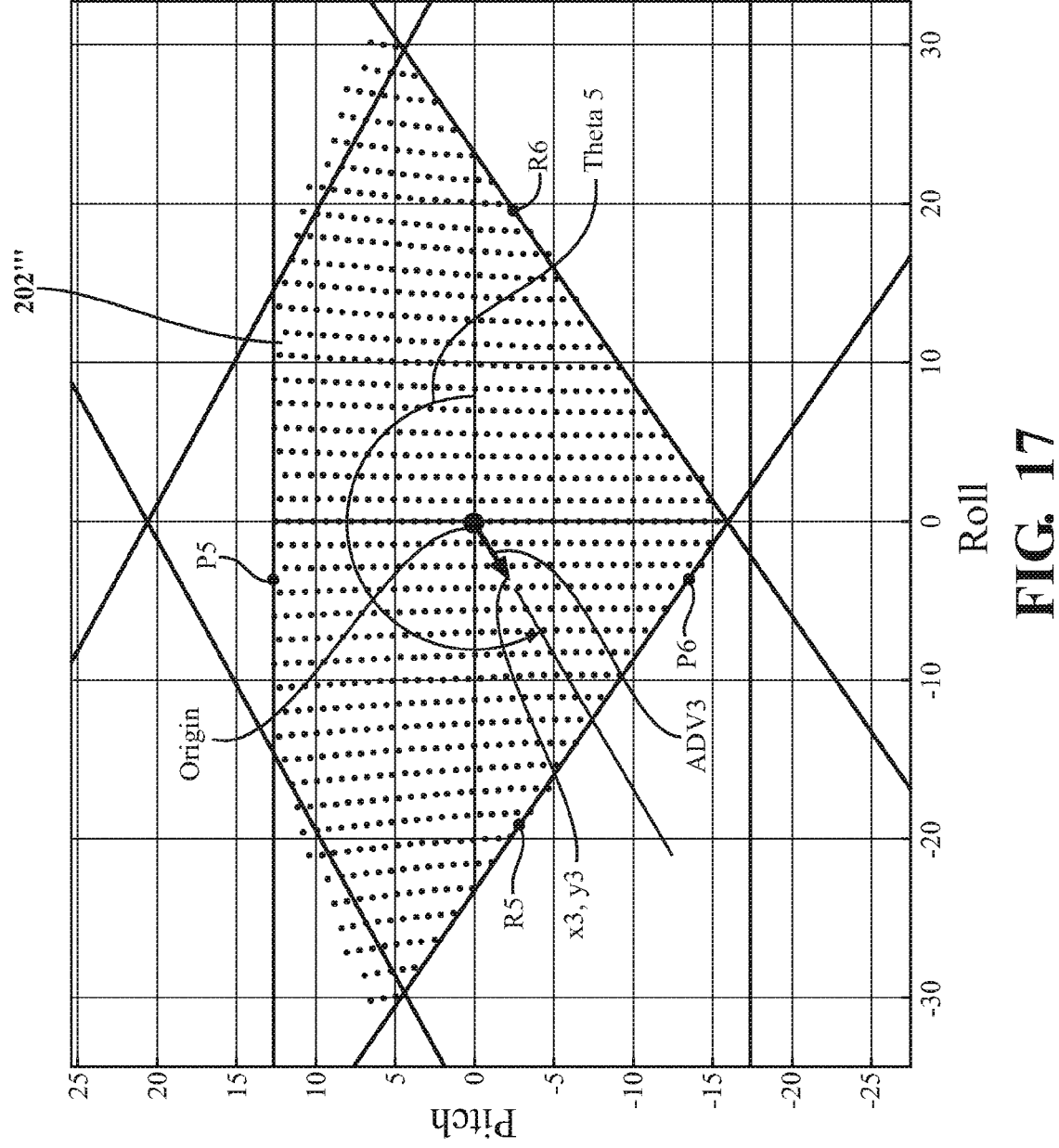

FIG. 17 illustrates the two-dimensional slice region of FIG. 16, with a third actual deviation vector.

Figure 18:
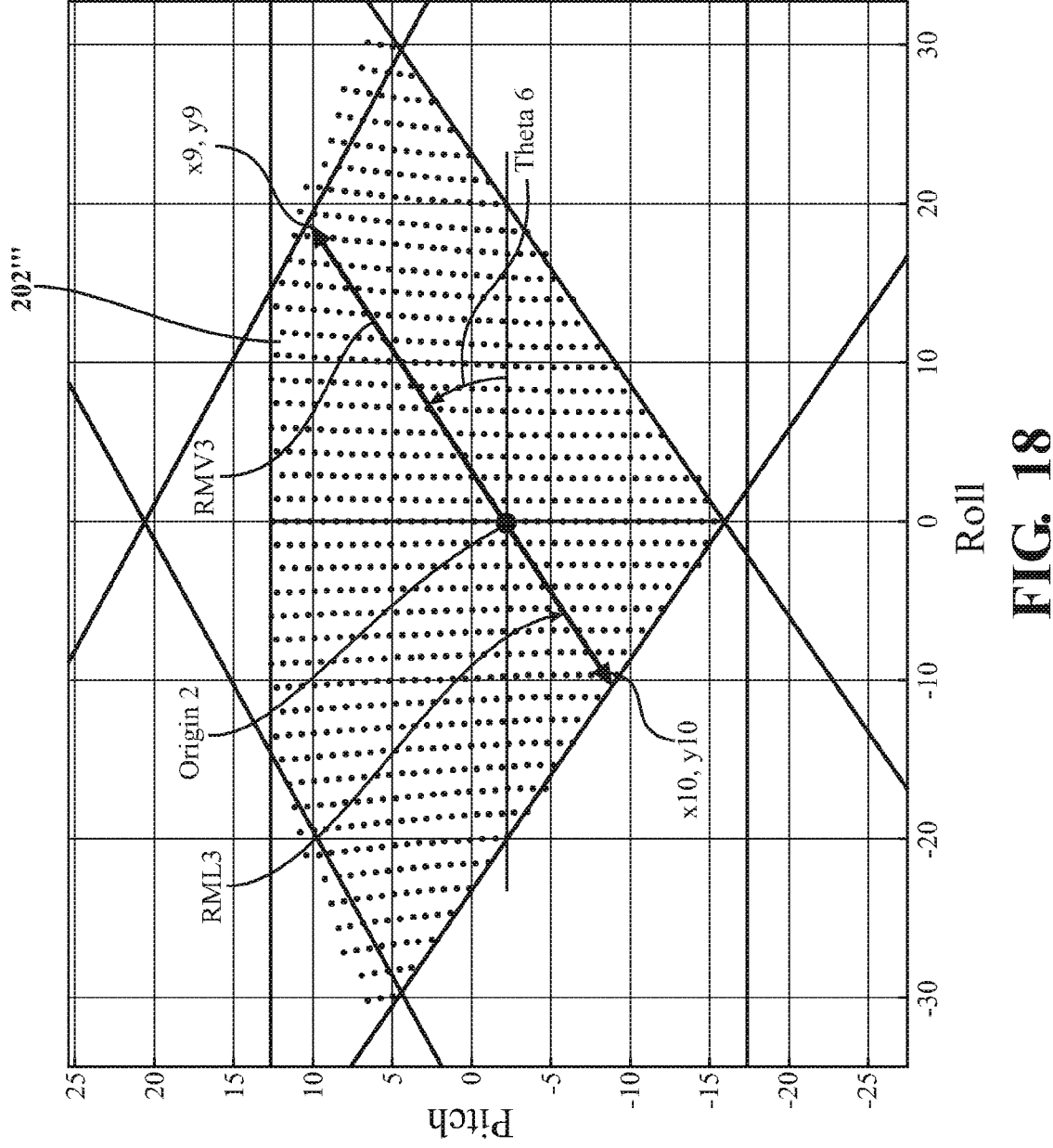

FIG. 18 illustrates the two-dimensional slice region of FIG. 13, with a third range of motion vector and a different origin.

Figure 19:
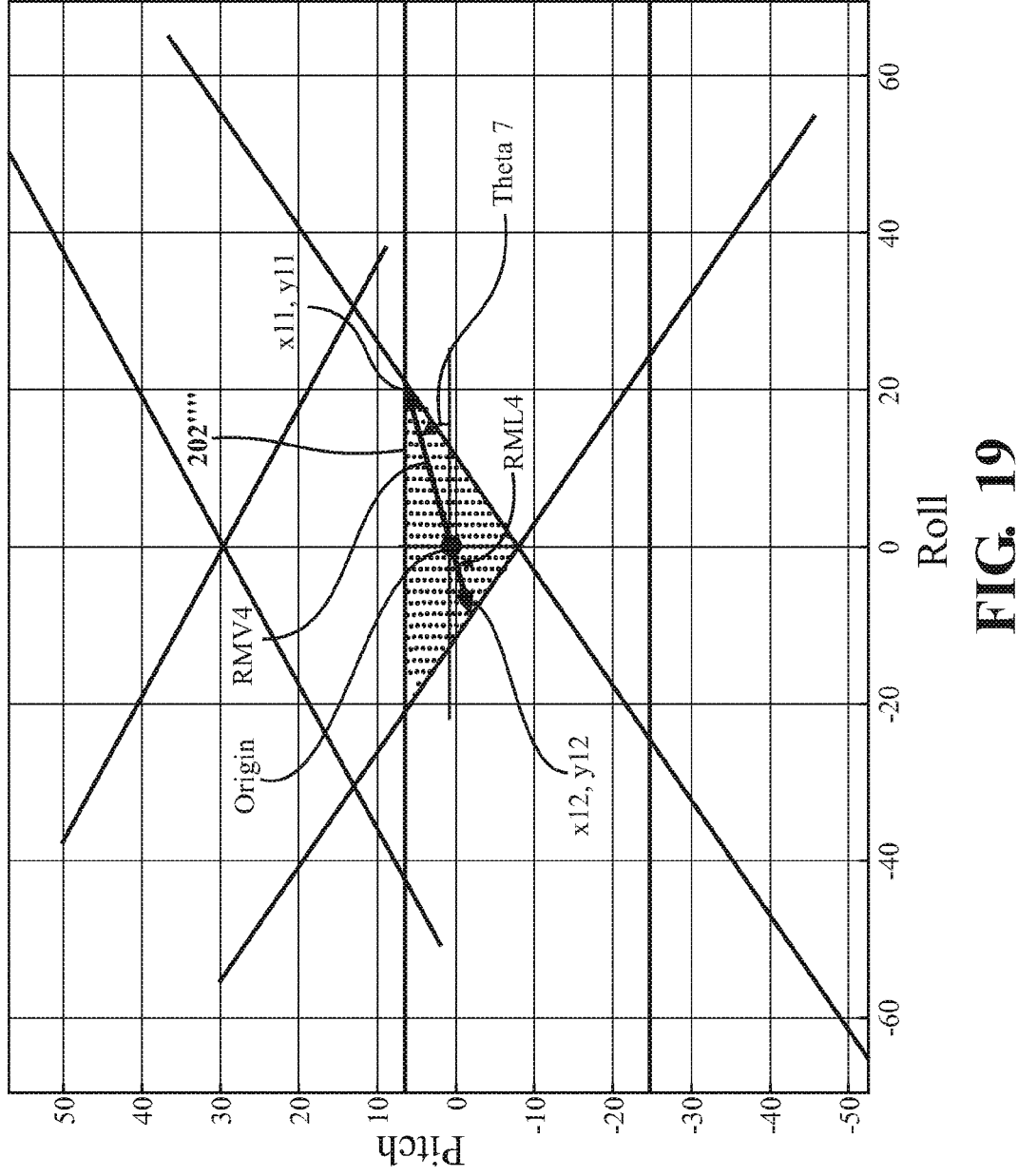

FIG. 19 illustrates a second two-dimensional slice region with a fourth range of motion vector.

Figure 20:
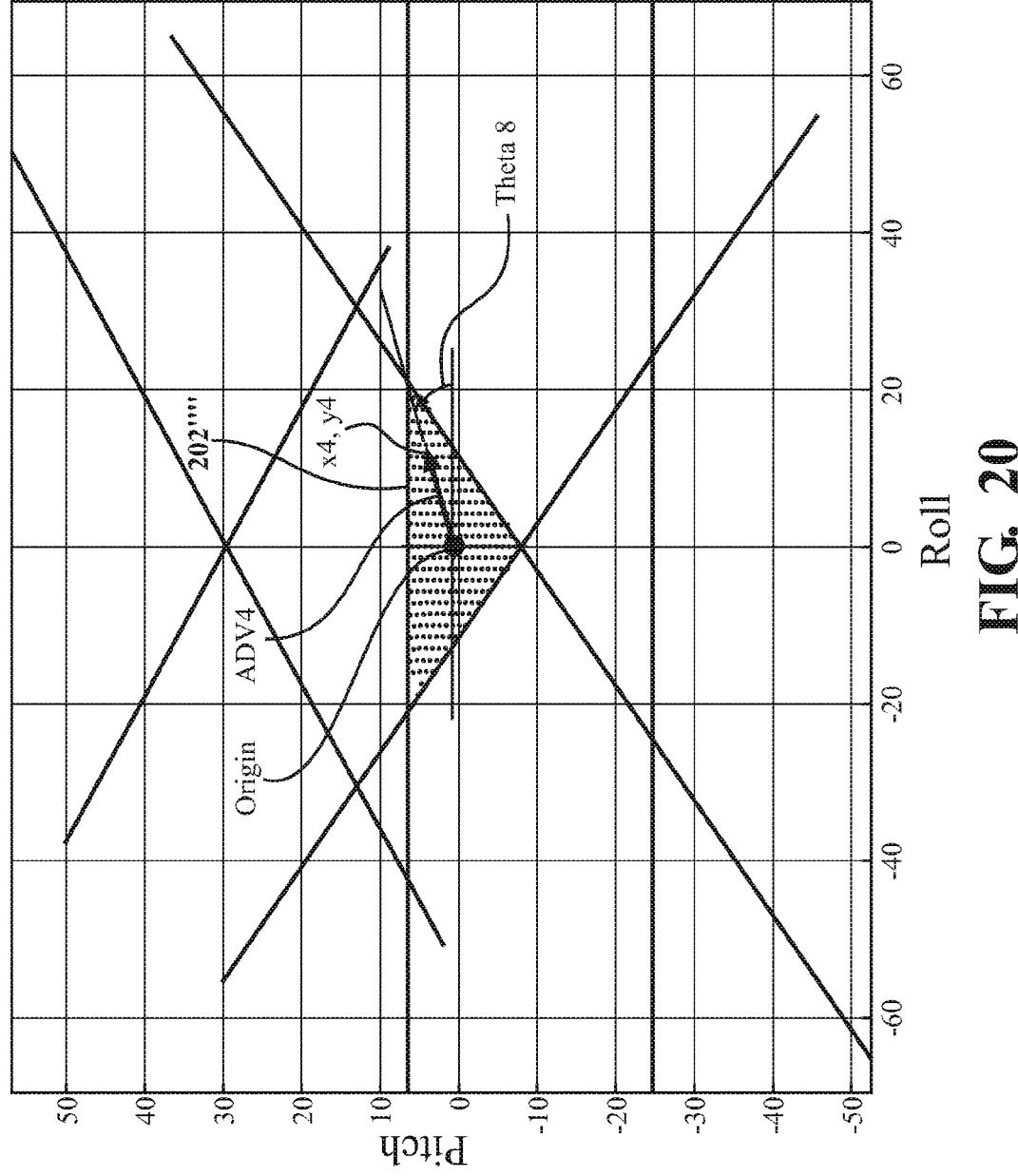

FIG. 20 illustrates the two-dimensional slice region of FIG. 19 with a fourth actual deviation vector.

Figure 21:
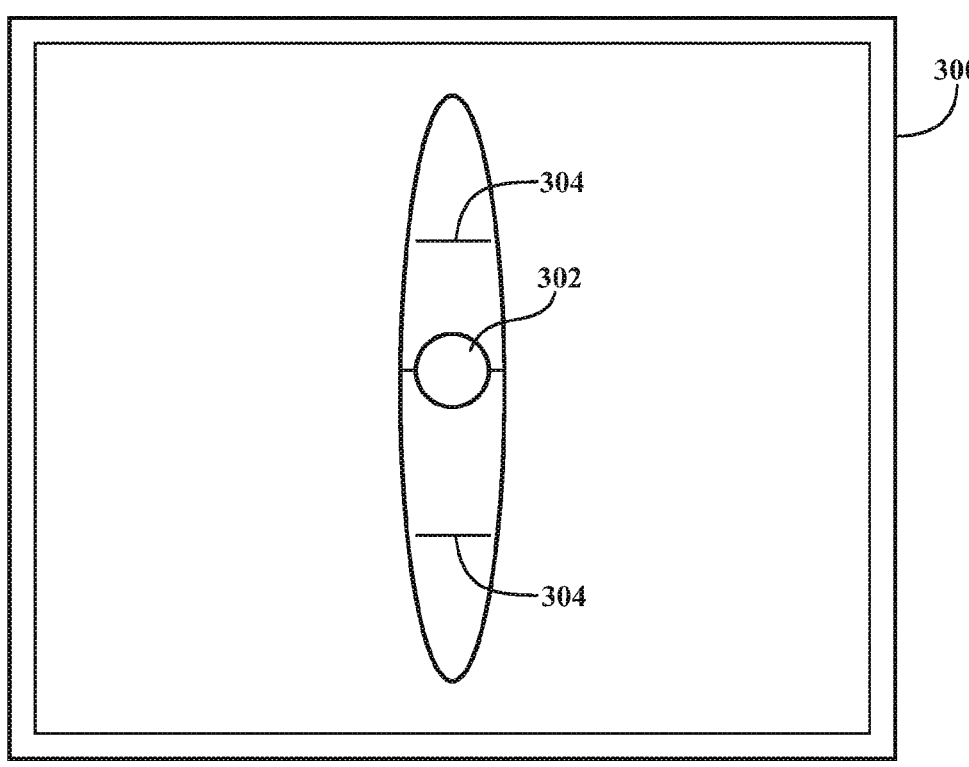

FIG. 21 illustrates a display screen with an elevation indicia.

Figure 22:
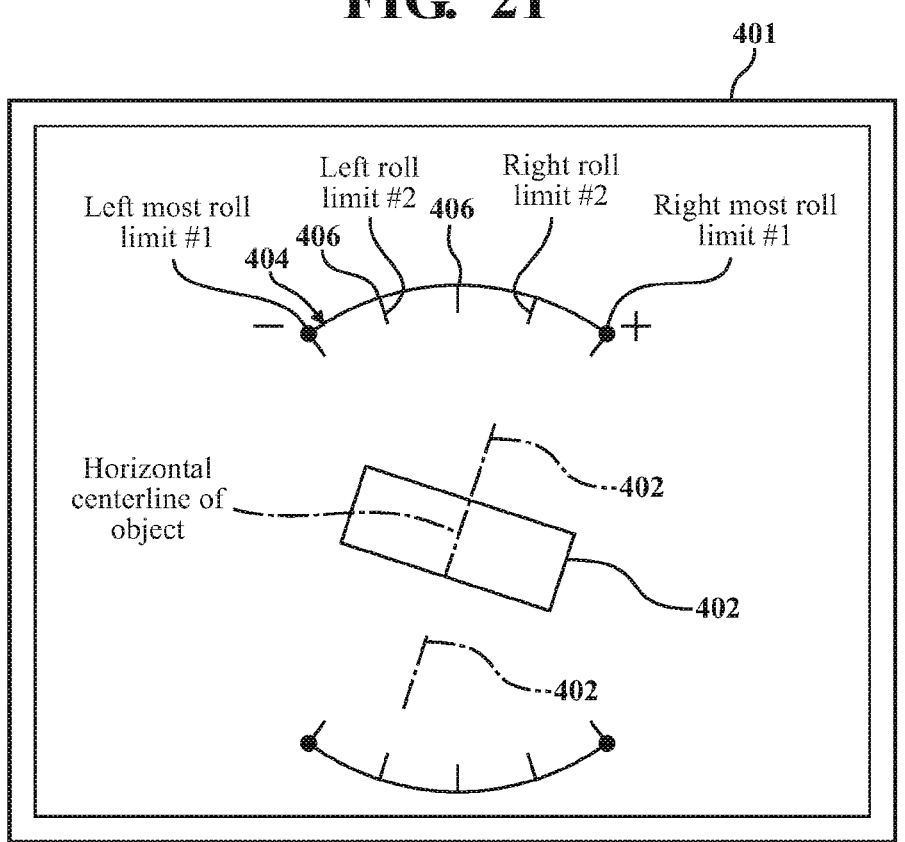

FIG. 22 illustrates a display screen with a roll indicia.

Figure 23:
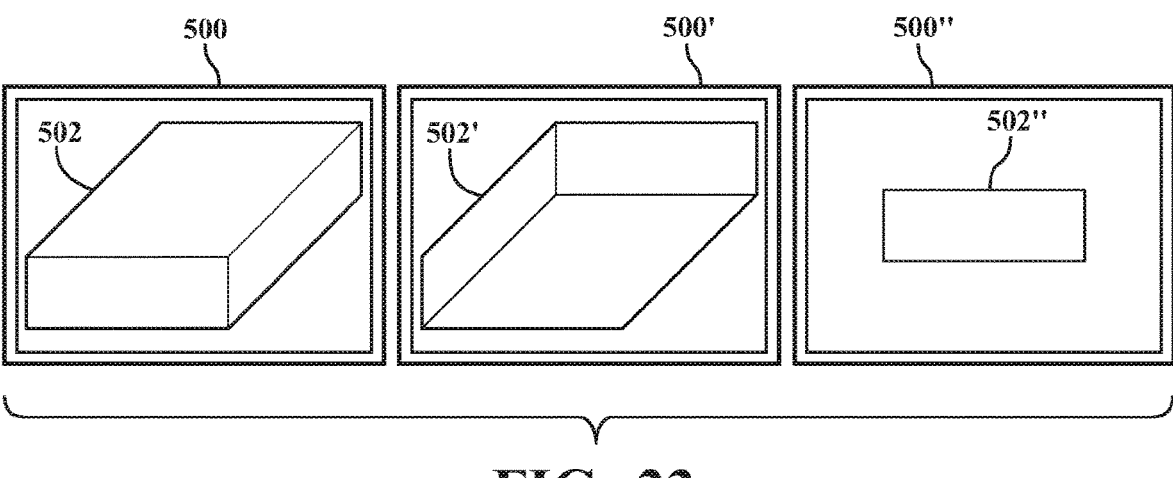

FIG. 23 illustrates three display screens with a pitch-roll indicia in three different configurations.

Figure 24:
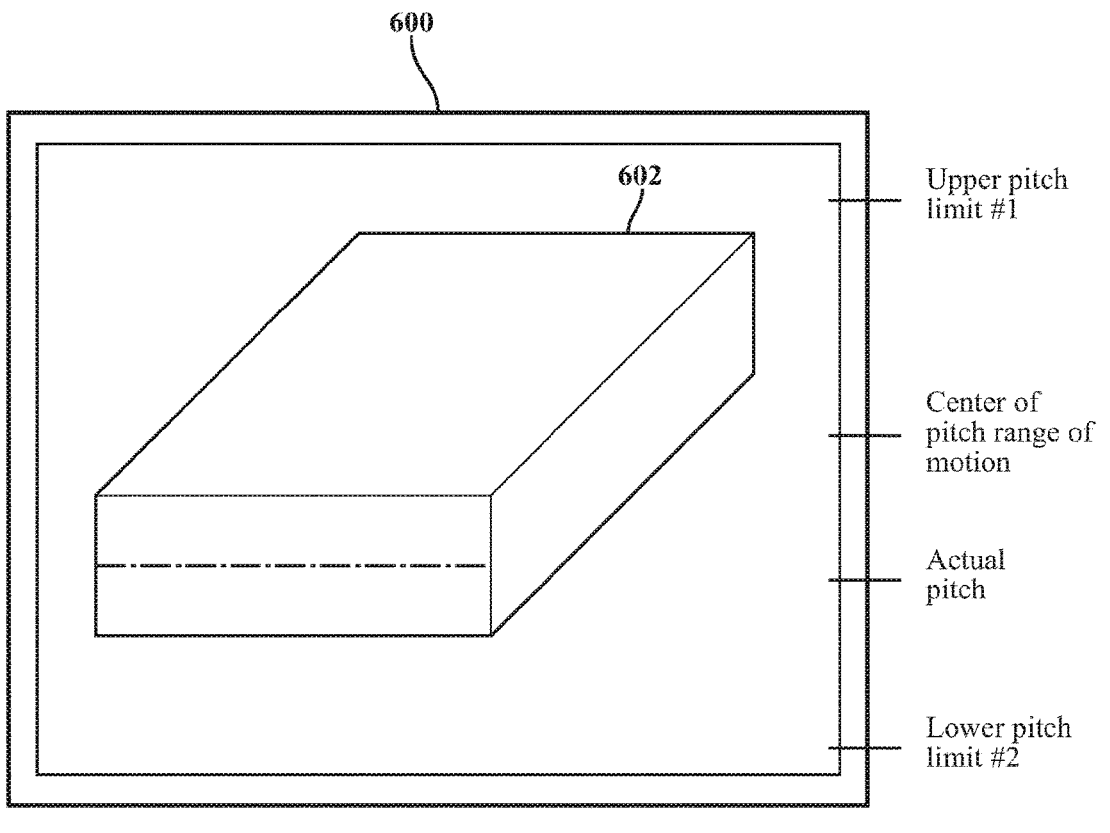

FIG. 24 illustrates a display screen with a pitch-roll indicia.

Figure 25:
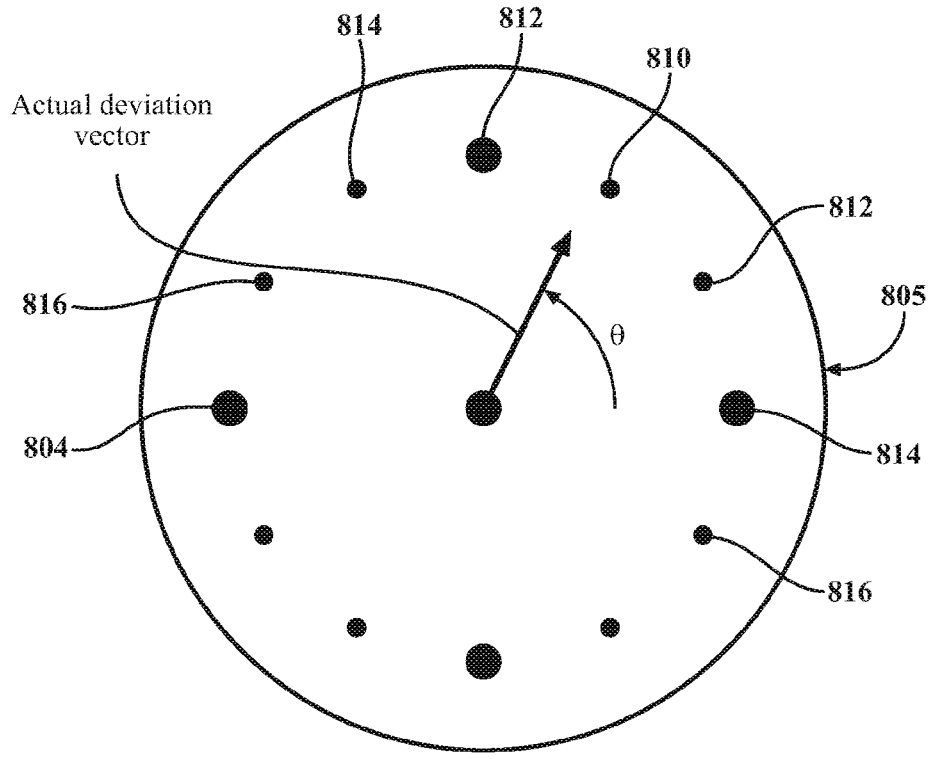

FIG. 25 illustrates a schematic representation of a visual indicator including a light array.

Figure 26:
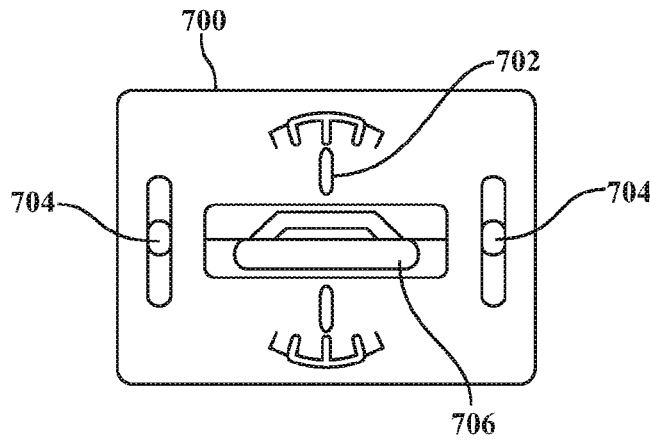

FIG. 26 illustrates a display screen including a roll indicia, a pitch-roll indicia and an elevation indicia when the instrument is in a home position.

Figure 27A:
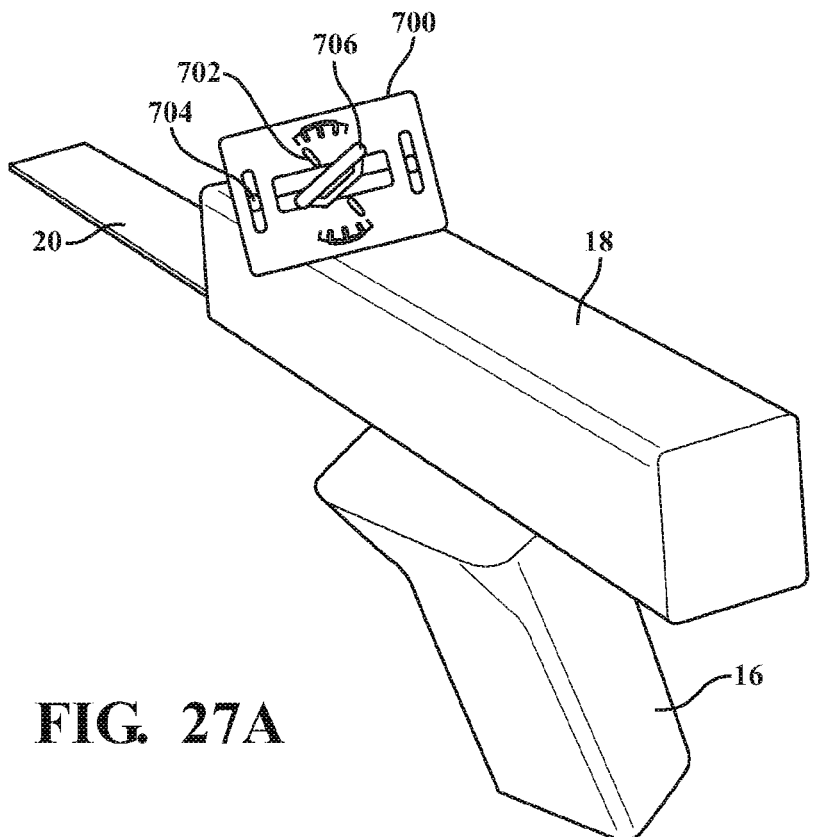

FIG. 27A illustrates a hand-held surgical instrument in a first spatial configuration other than a home position, with a display screen visual indicator.

Figures 27B, 27C:
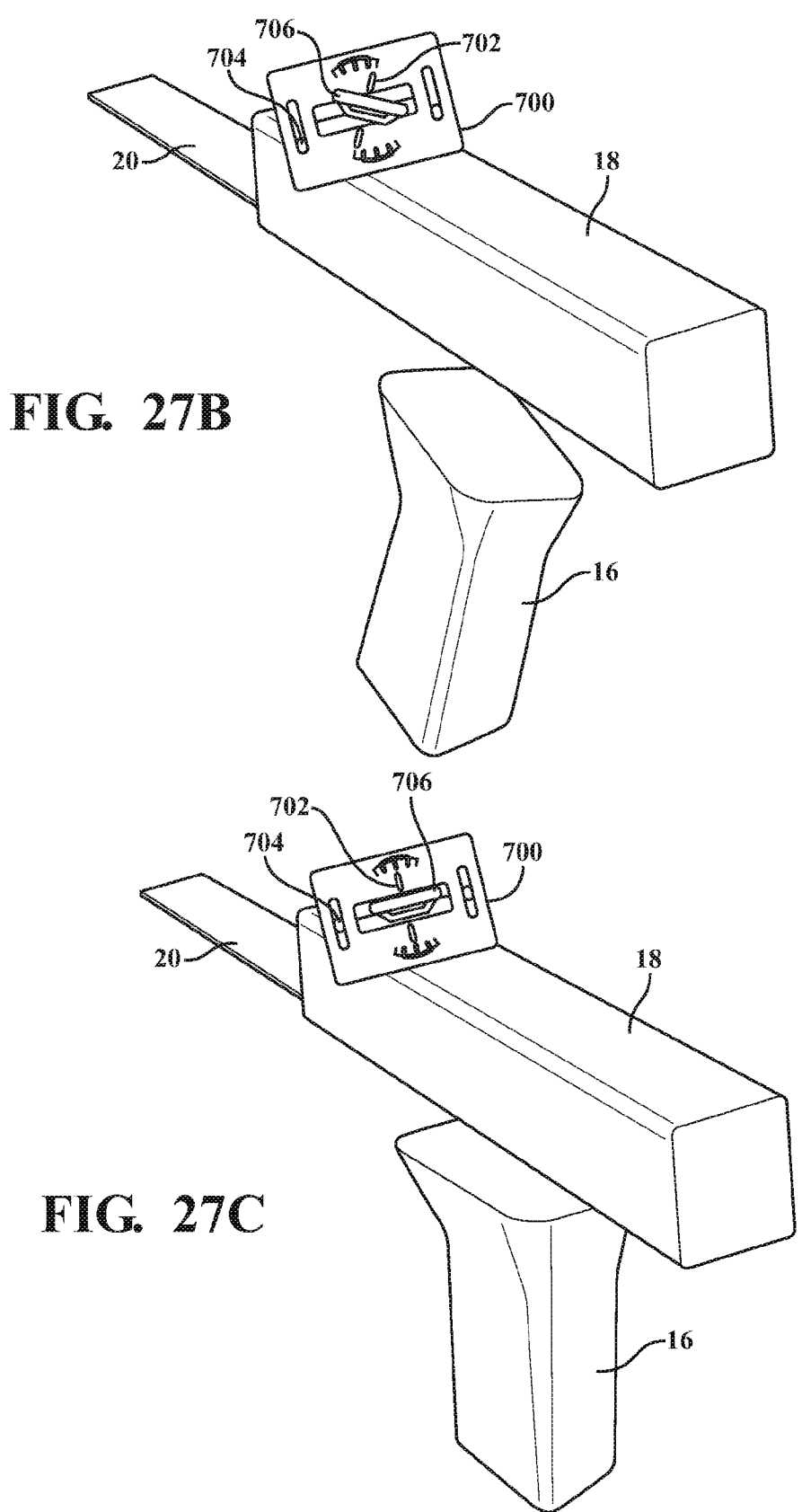

FIG. 27B illustrates a hand-held surgical instrument in a second spatial configuration other than a home position, with a display screen visual indicator.

FIG. 27C illustrates a hand-held surgical instrument in a third spatial configuration other than a home position, with a display screen visual indicator.

FIG. 28 illustrates a hand-held surgical instrument in a first spatial configuration with a visual indicator including a plurality of light sources.

FIG. 29A-29G show the visual indicator of FIG. 28 in different states pertaining to different spatial configurations of the hand-held surgical instrument.

FIG. 30A-30E show a schematic view of the translation visual indicator of FIG. 28 in different states pertaining to different elevation configurations of the hand-held surgical instrument.

FIG. 31 shows another visual indicator configuration with a plurality of light sources.

FIGS. 32A-C shows three exemplary display screen visual indicators to facilitate positioning of a user's hand.

Figures 33A, 33B:
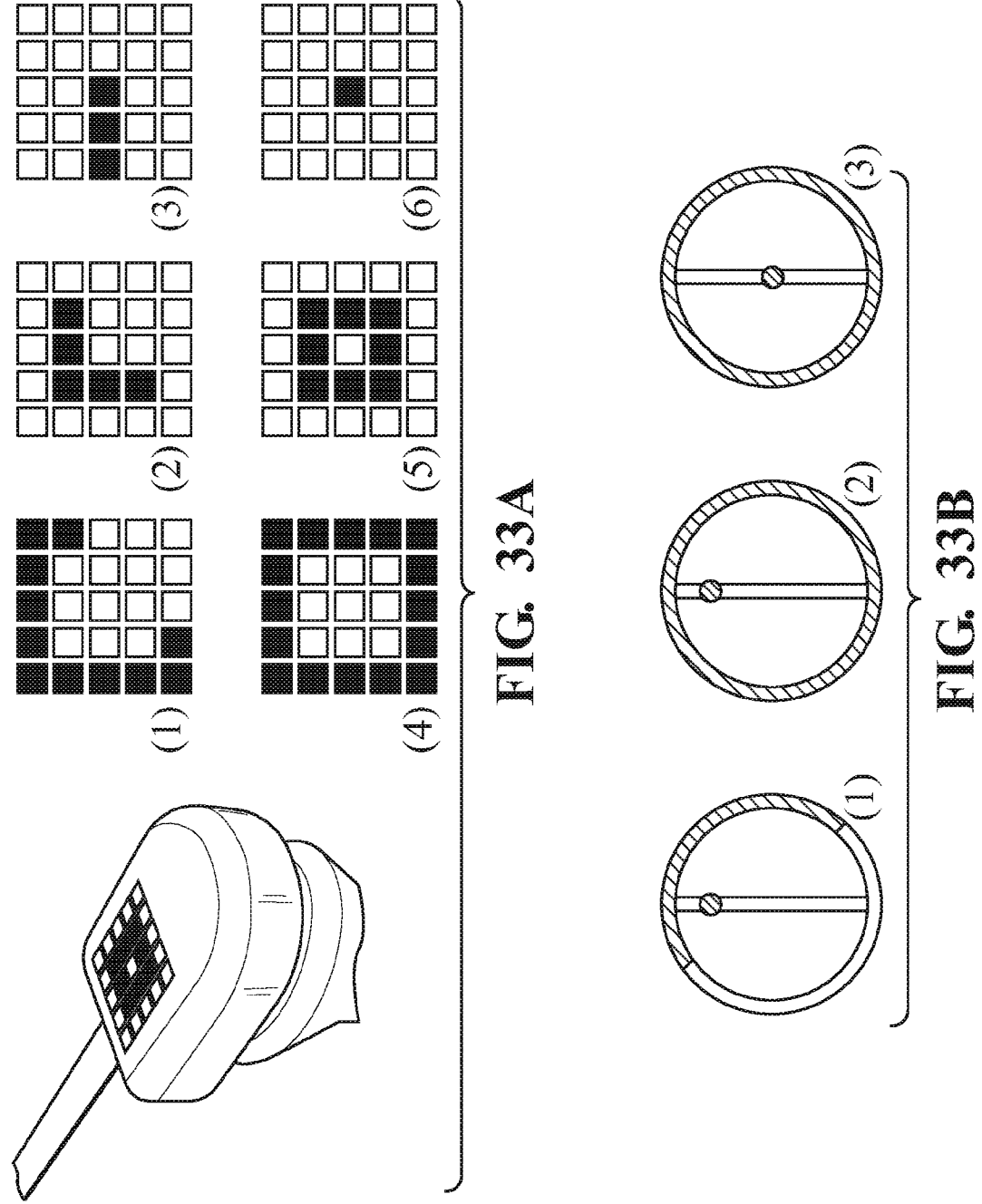

FIG. 33A show another exemplary visual indicator with a plurality of light sources.

FIG. 33B show another exemplary visual indicator on a display screen.

Figure 34:
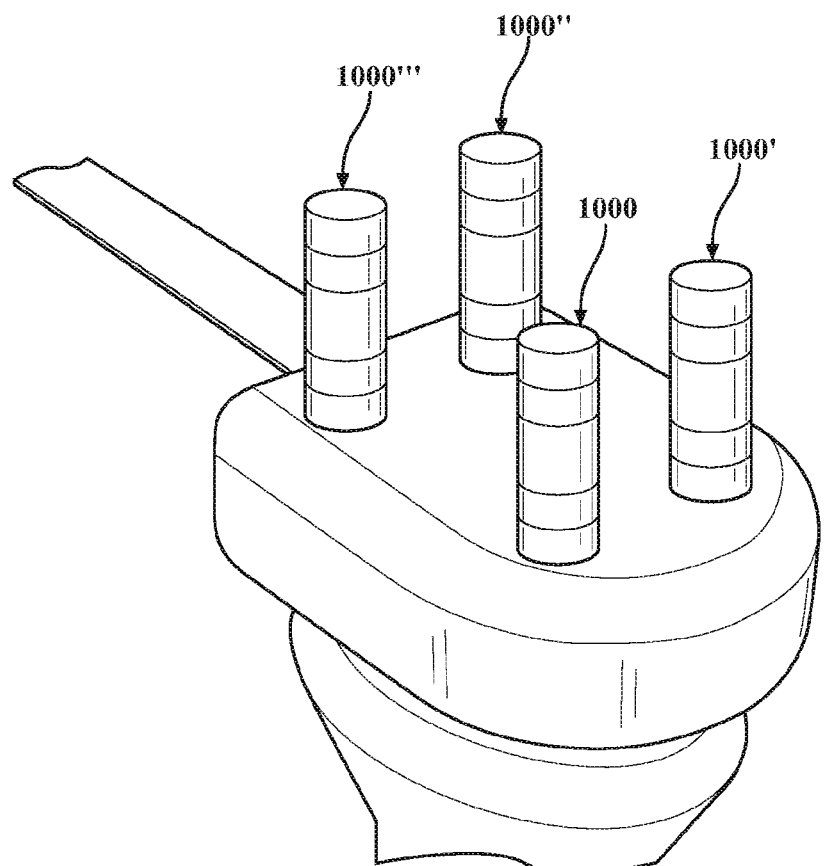

FIG. 34 shows another exemplary visual indicator with a plurality of light sources arranged in posts.

FIG. 35A-C show yet another visual indicator on a display screen corresponding to three different spatial configurations of the hand-held surgical instrument.

Figures 36A, 36B, 36C:
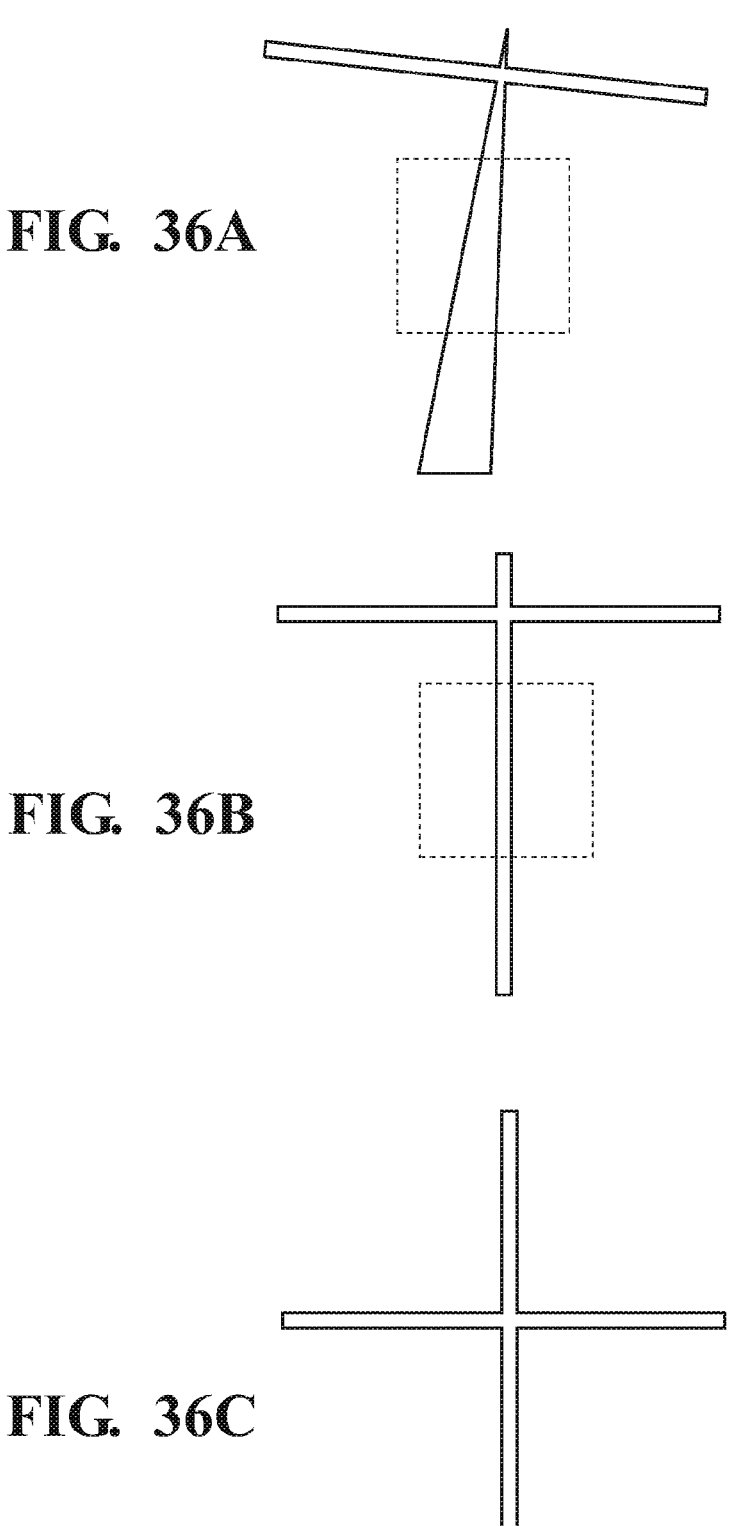

FIG. 36A-C show another visual indicator in three different configurations.

Figure 37:
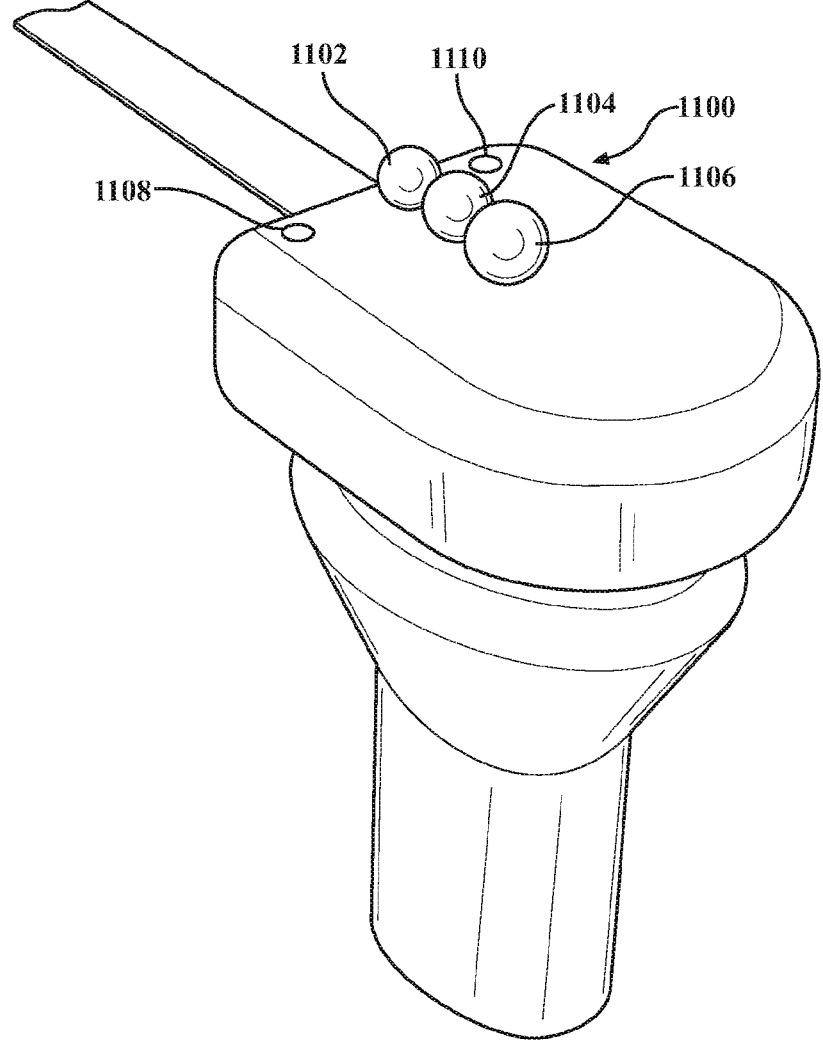

FIG. 37 show another visual indicator including a plurality of light sources.

Figure 38:
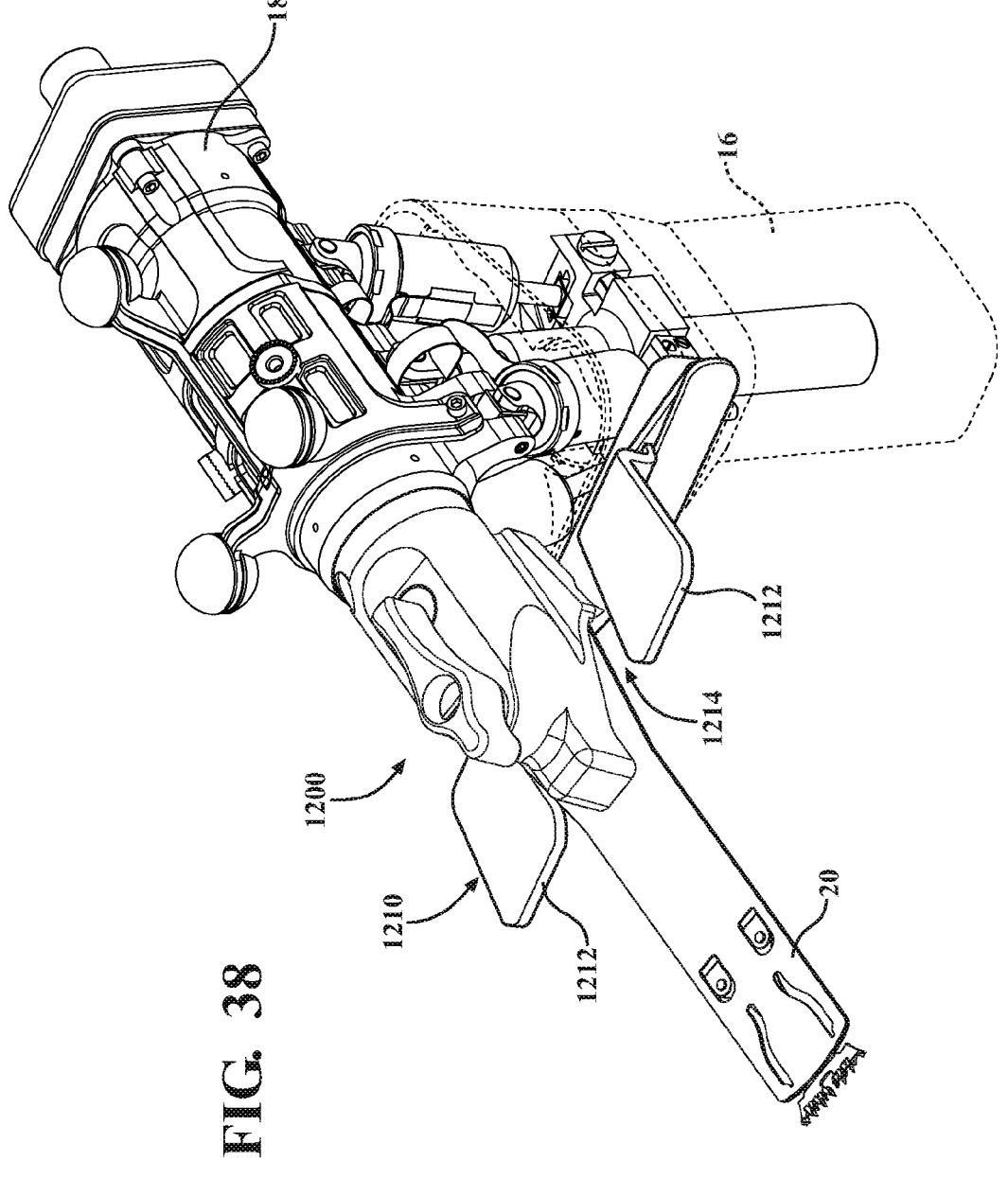

FIG. 38 show a visual indicator that is implemented mechanically.

Figure 39:
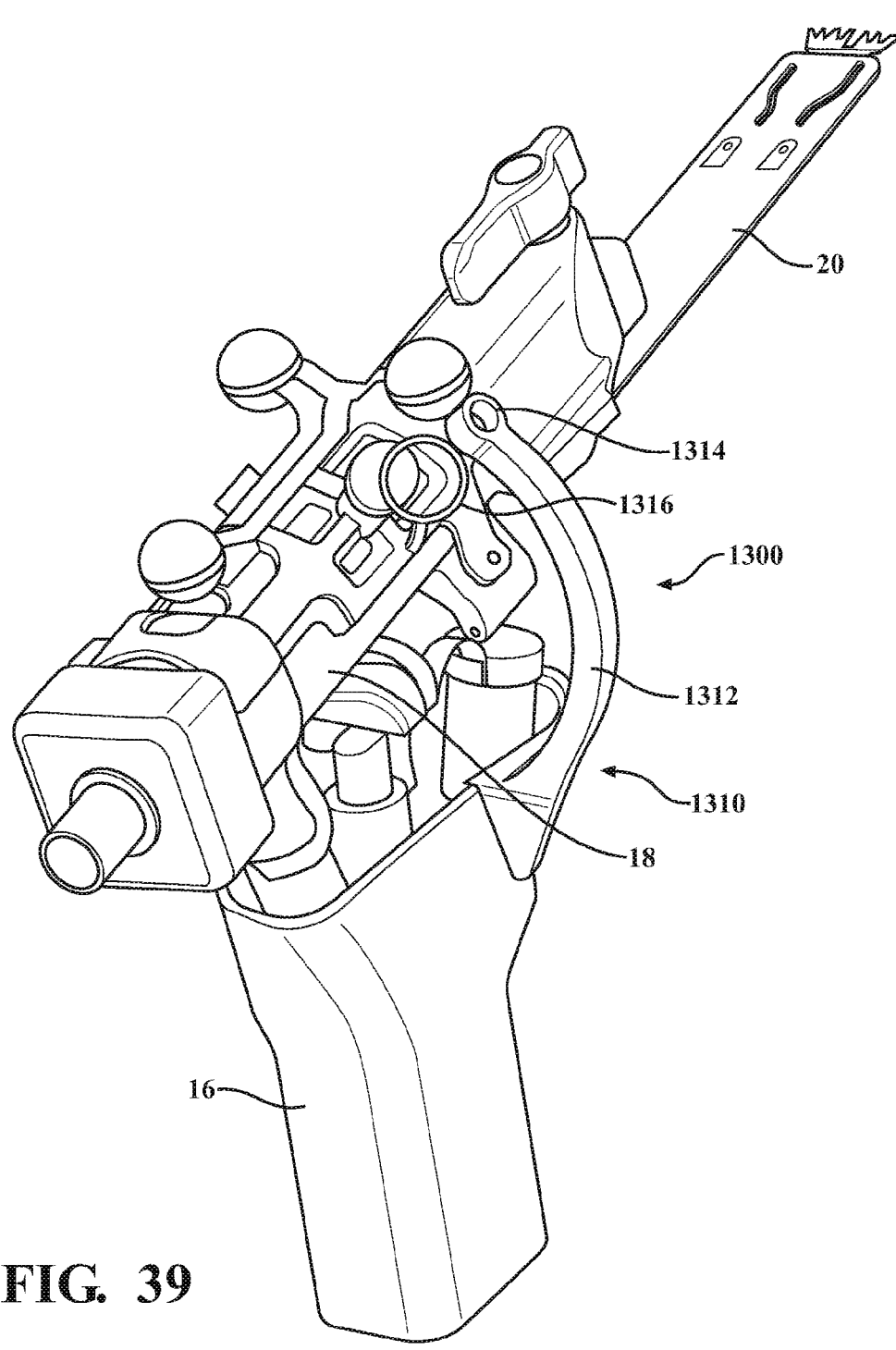

FIG. 39 show another visual indicator that is implemented mechanically.

Figure 40:
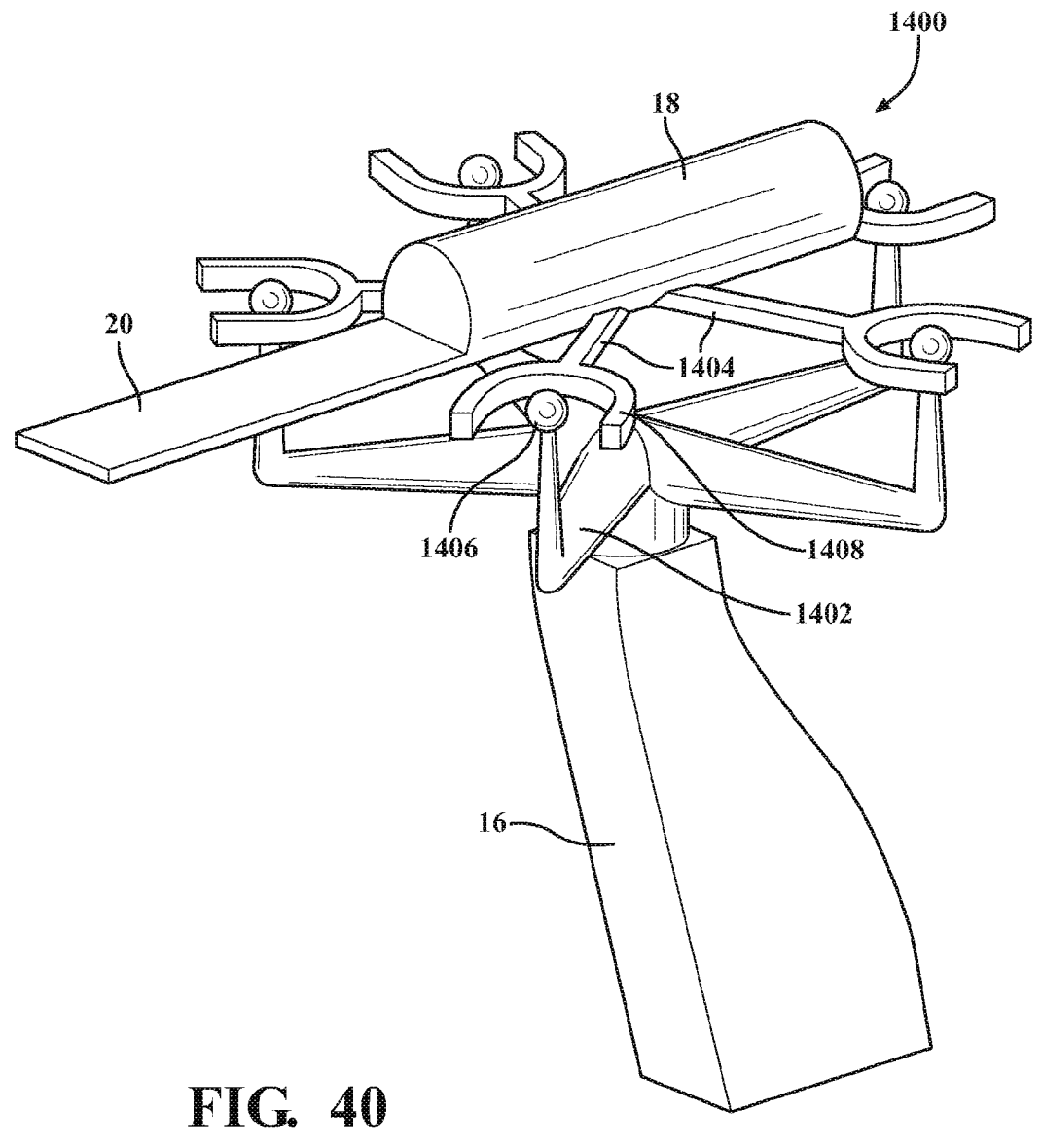

FIG. 40 shows yet another visual indicator that is implemented mechanically.

Figure 41:
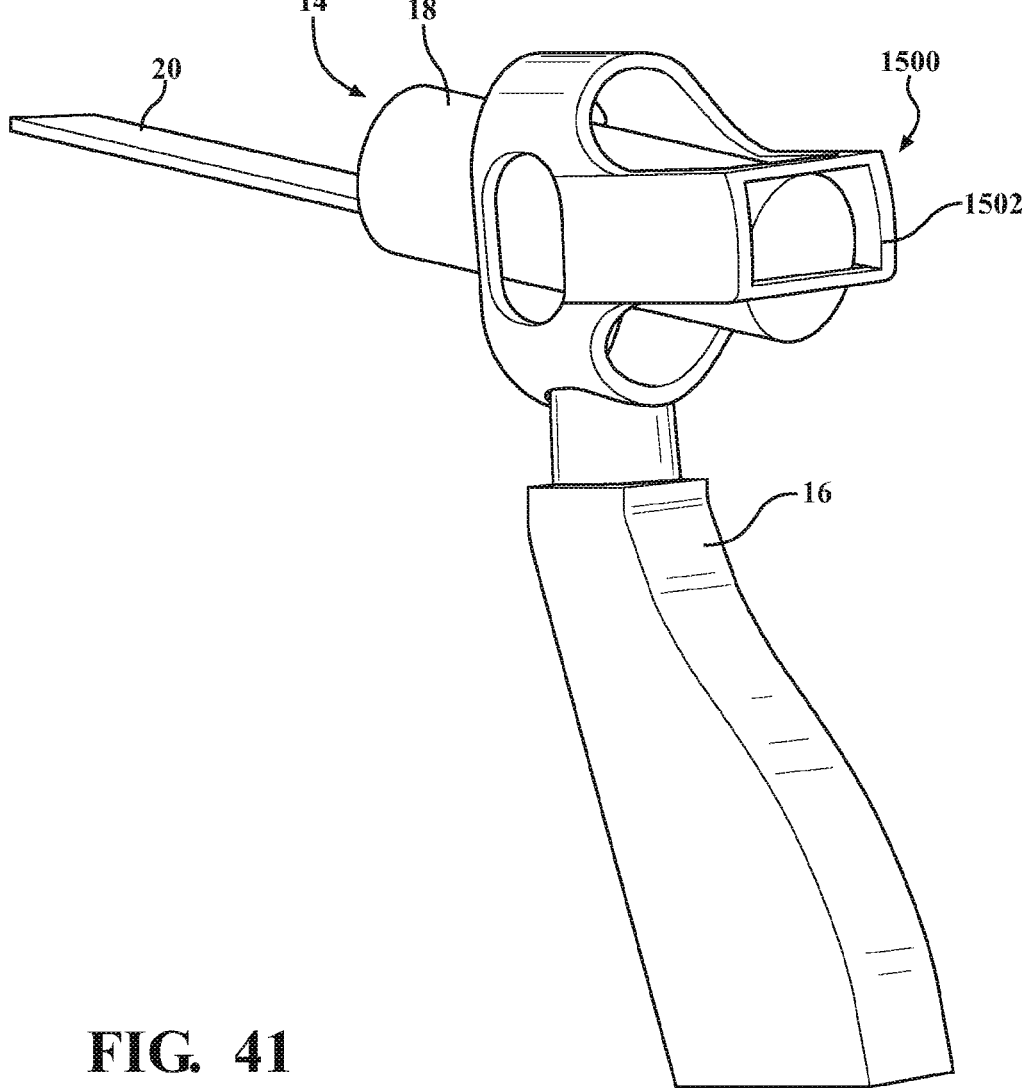

FIG. 41 shows yet another visual indicator that is implemented mechanically.

Figure 42A:
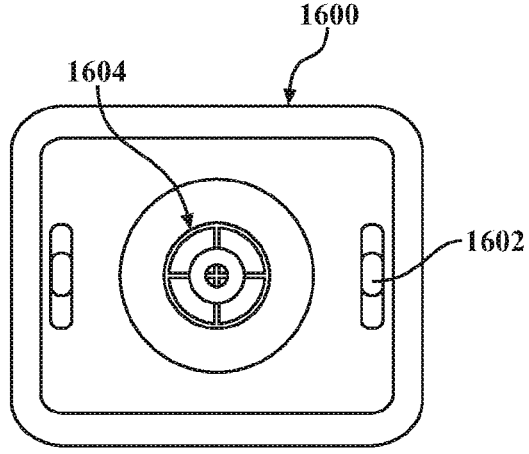
Figure 42B:
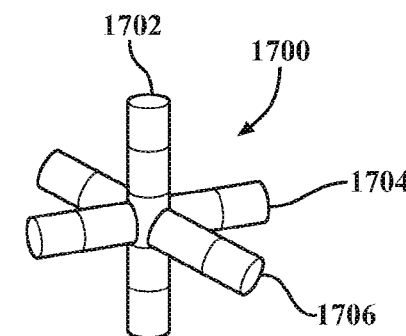
Figure 42C:
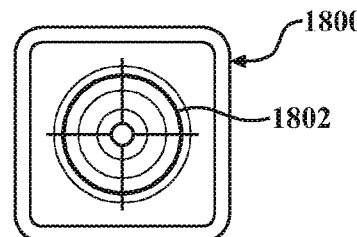

FIGS. 42A-42C shows three more exemplary visual indicators.

DETAILED DESCRIPTION

Overview

Figure 1:
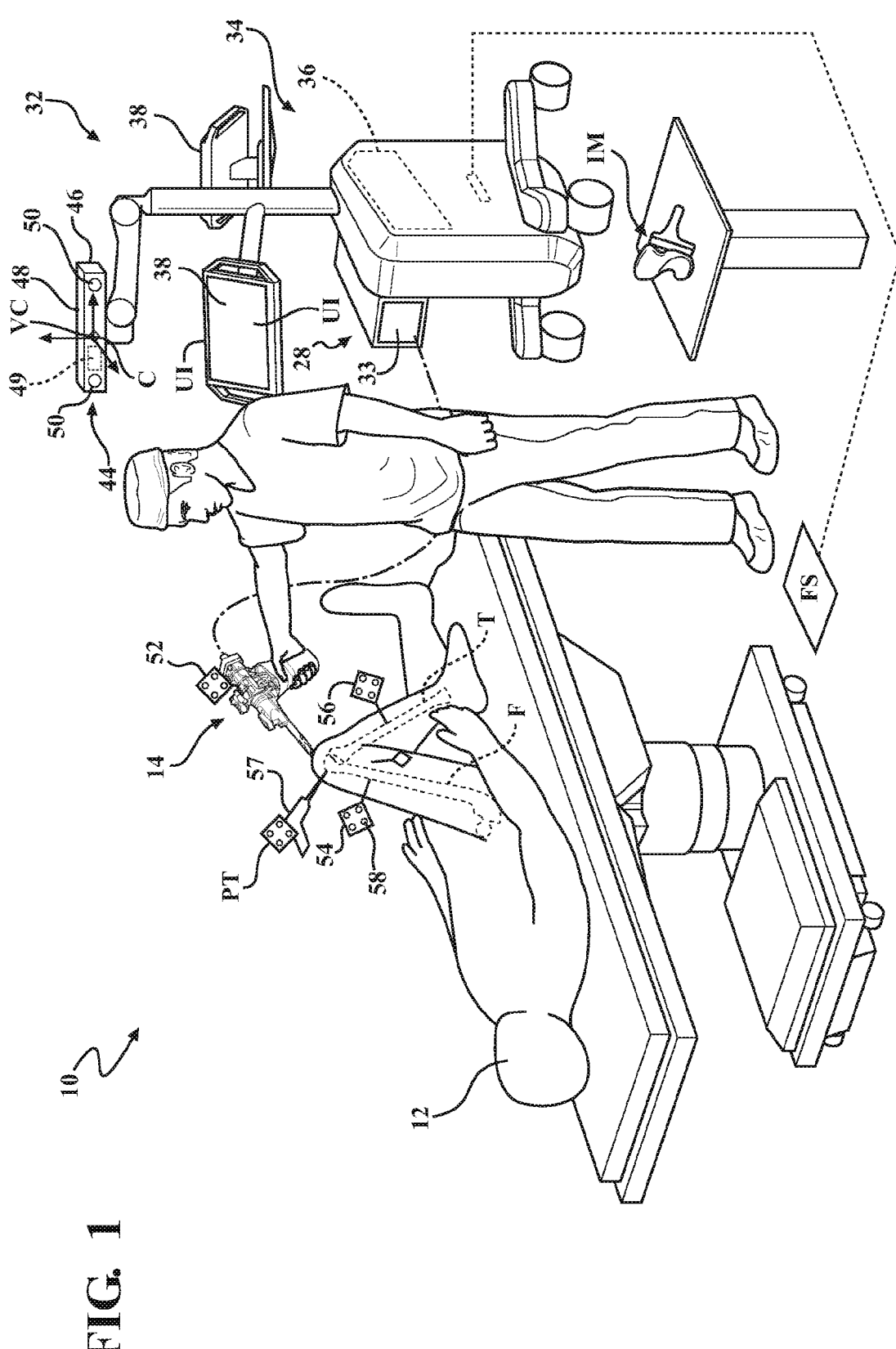
FIG. 1 is a perspective view of a robotic system.

Referring to FIG. 1, a robotic system 10 is illustrated. The robotic system 10 is shown performing a total knee procedure on a patient 12 to resect portions of a femur F and tibia T of the patient 12 so that the patient 12 can receive a total knee implant IM. The robotic system 10 may be used to perform other types of surgical procedures, including procedures that involve hard/soft tissue removal, or other forms of treatment. For example, treatment may include cutting tissue, coagulating tissue, ablating tissue, stapling tissue, suturing tissue, or the like. In some examples, the surgical procedure involves knee surgery, hip surgery, shoulder surgery, spine surgery, or ankle surgery, and may involve removing tissue to be replaced by surgical implants, such as knee implants, hip implants, shoulder implants, spine implants, or ankle implants. The robotic system 10 and techniques disclosed herein may be used to perform other procedures, surgical or non-surgical, and may be used in industrial applications or other applications where robotic systems are utilized.

Figure 2:
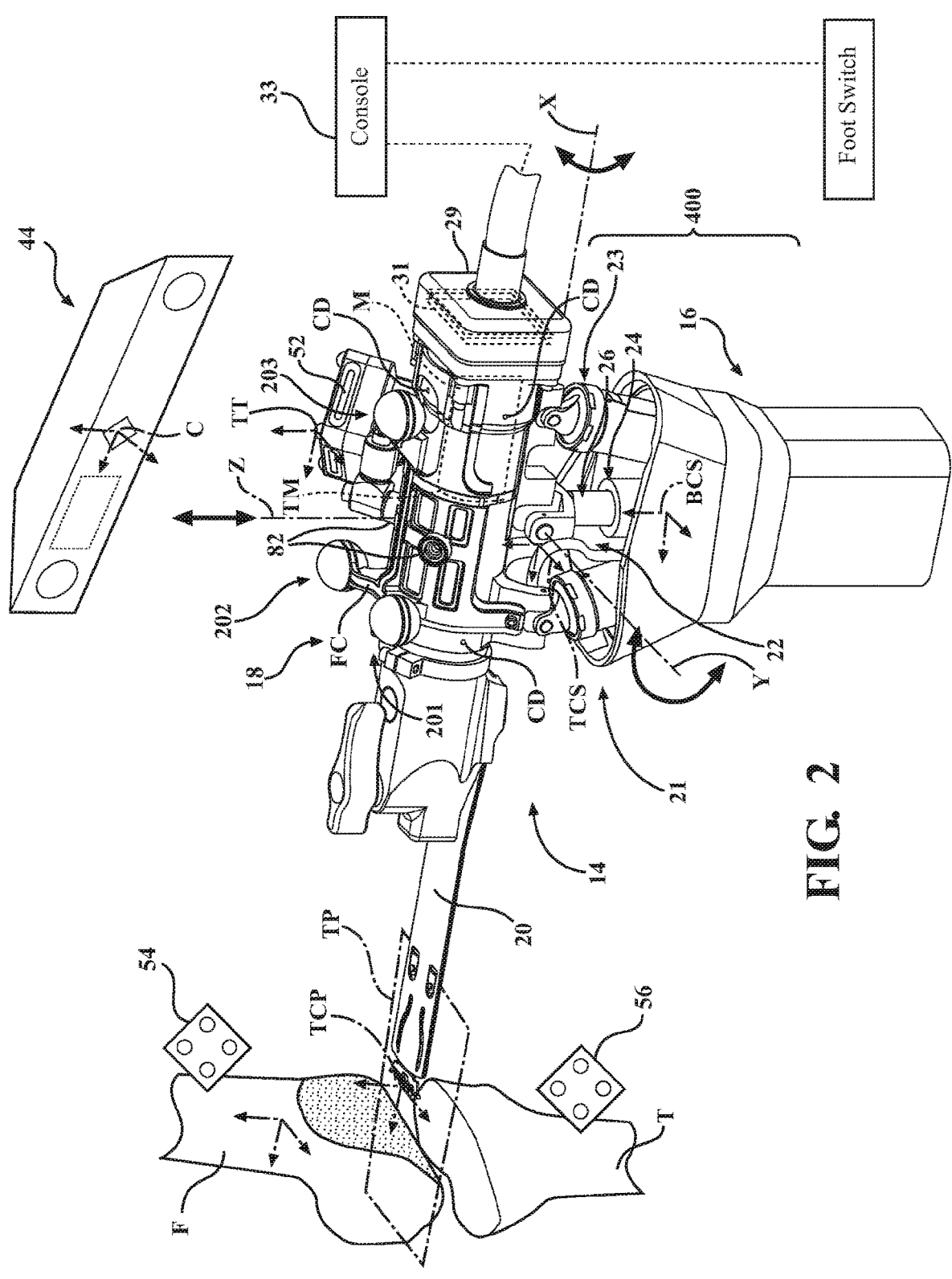
FIG. 2 is a perspective view of a robotic instrument being used to cut five planes on a femur to receive a total knee implant.
Figures 3A, 3B, 3C:
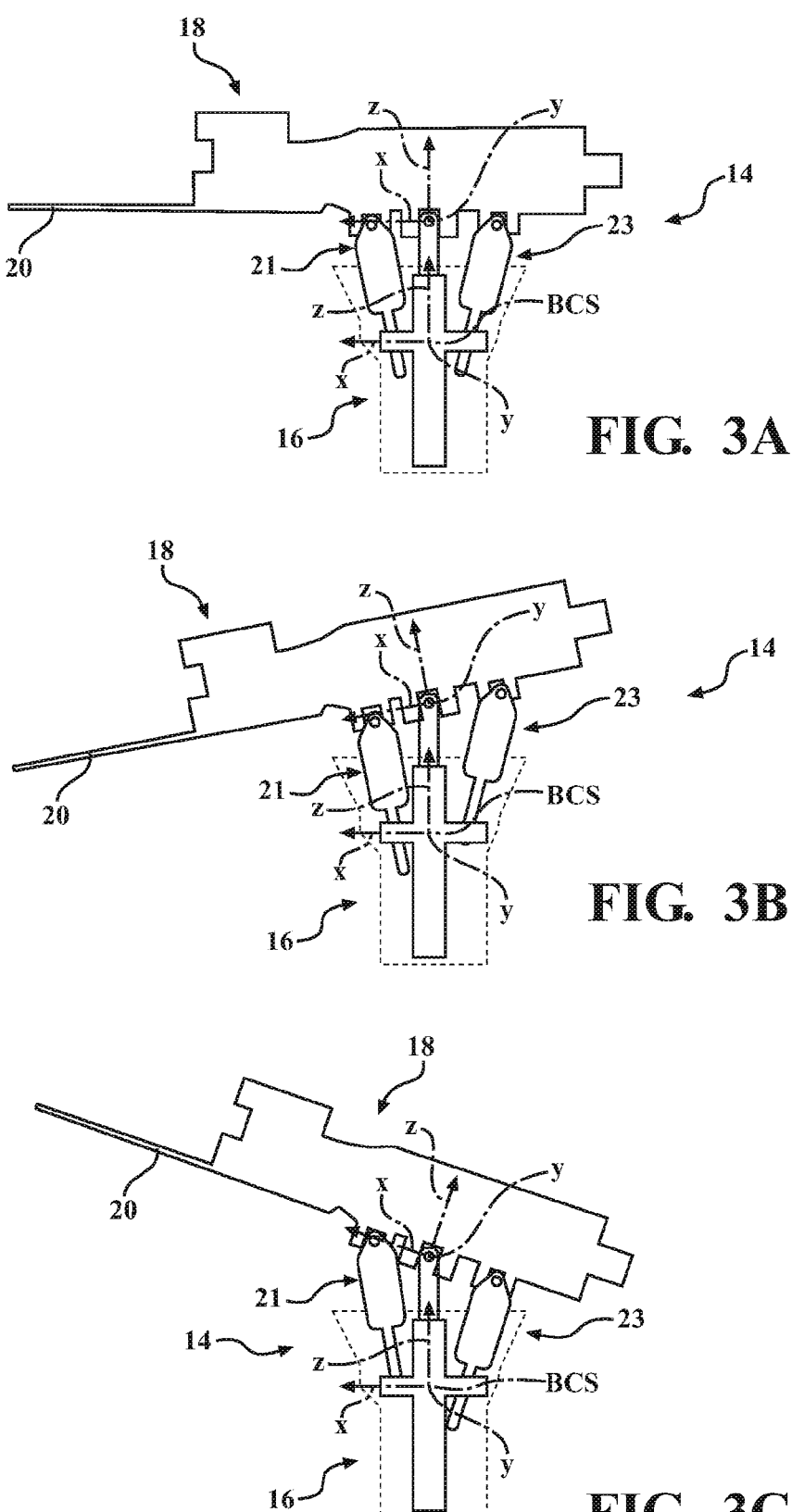
FIGS. 3A-3C are illustrations of various pitch orientations of the robotic instrument.
Figures 4A, 4B, 4C:
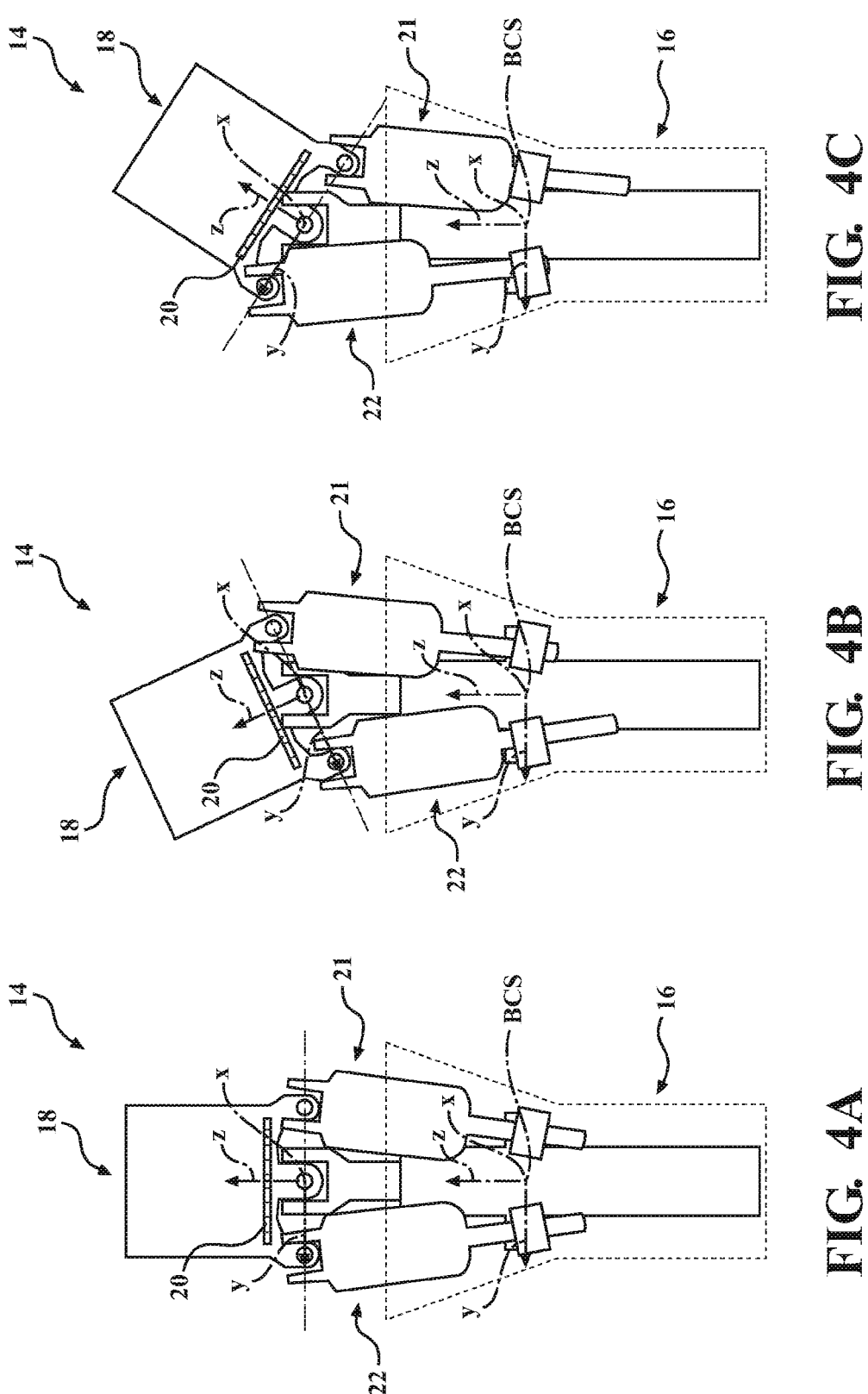
FIGS. 4A-4C are illustrations of various roll orientations of the robotic instrument.
Figures 5A, 5B, 5C:
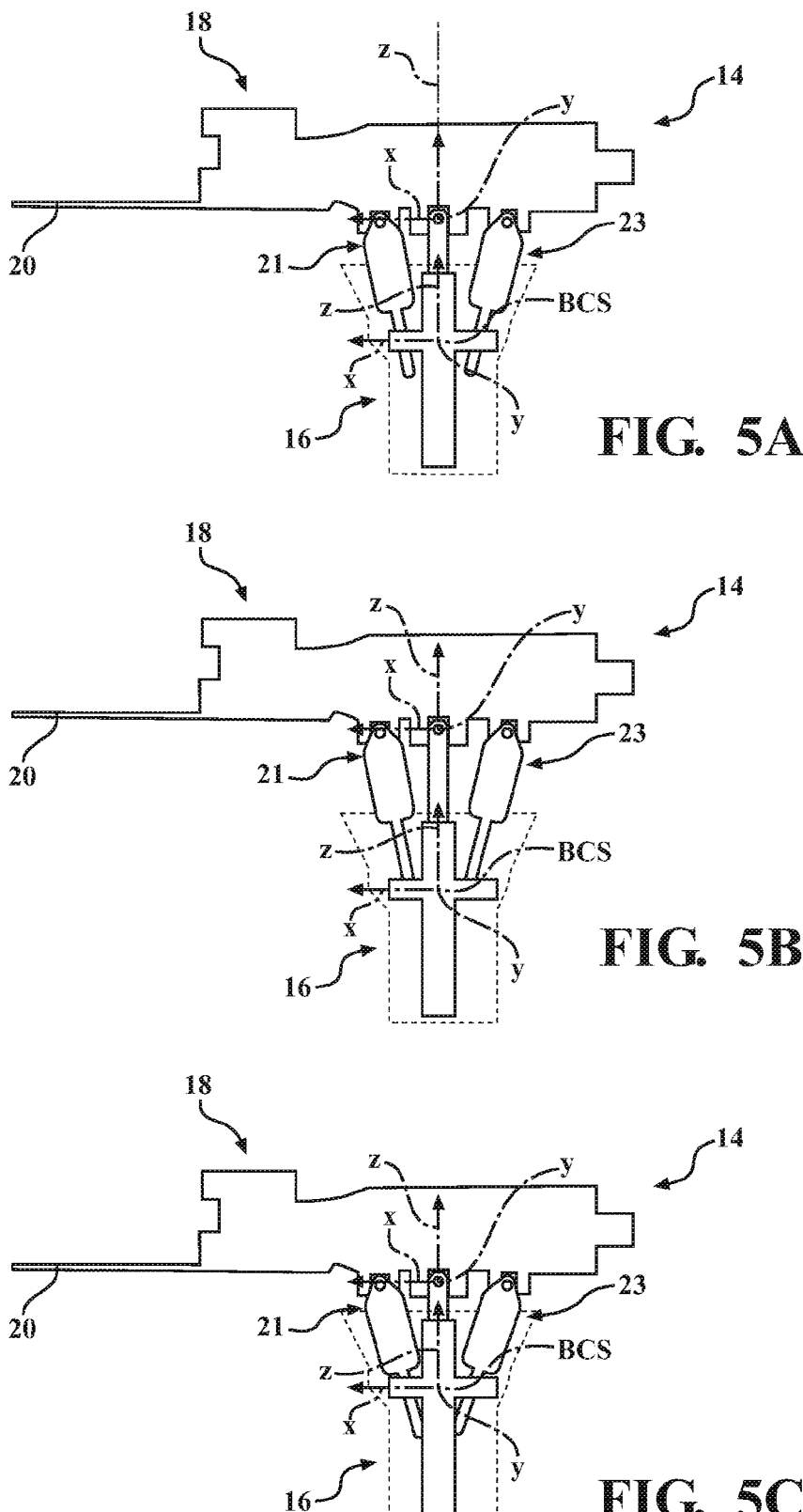
FIGS. 5A-5C are illustrations of various z-axis translation positions of the robotic instrument.

Referring to FIGS. 1 and 2, the robotic system 10 includes an instrument 14. In some examples, a user manually holds and supports the instrument 14 (as shown in FIG. 1). In some examples, the user may manually hold the instrument 14 while the instrument is being at least partially, or fully, supported by an assistive device, such as a passive arm (e.g., linkage arm with locking joints, weight-balancing arm), an active arm, or the like. As best shown in FIGS. 1 and 2, the instrument 14 comprises a hand-held portion 16 for being manually grasped, or supported by the user, the assistive device, or both.

The instrument 14 may be freely moved and supported by a user without the aid of a guide arm, e.g., configured to be held by a human user while effecting physical removal of material such that the weight of the tool is supported solely by a hand of the user during the procedure. Put another way, the instrument 14 may be configured to be held such that the user's hand is supporting the instrument 14 against the force of gravity. The instrument 14 may weigh 8 lbs. or less, 6 lbs. or less, 5 lbs. or less, or even 3 lbs. or less. The instrument 14 may have a weight corresponding to ANSI/AAMI HE75: 2009. The instrument 14 also comprises a tool support 18 for receiving a tool 20. In some examples, when the tool 20 is a saw blade 380, the tool support 18 may be referred to as a blade support. The method for operating the instrument 14 may include a user suspending the weight of the instrument 14 without any assistance from a passive arm or robotic arm. Alternately, the weight of the instrument 14 may be supported through use of a counter-balanced passive arm, assistive device, or active robotic arm, such that the user does not have to support the entire weight of the instrument. In such cases, the user may still grasp the hand-held portion 16 in order to interact with or guide the instrument 14. The passive arm and the contents of U.S. Pat. No. 9,060,794 to Kang et al. are incorporated herein by reference. Furthermore, the robotic system 10, in some examples, may be free from a robot arm having more than one joint in series.

The tool 20 couples to the tool support 18 to interact with the anatomy in certain operations of the robotic system 10 described further below. The tool 20 may also be referred to as an end effector. The tool 20 may be removable from the tool support 18 such that new tools or different tools 20 can be attached when needed. The tool 20 may also be permanently fixed to the tool support 18. The tool 20 may comprise an energy applicator designed to contact the tissue of the patient 12. In some examples, the tool 20 may be a saw blade, as shown in FIGS. 1 and 2, or other type of cutting accessory. In such instances, the tool support may be referred to as a blade support. It should be appreciated that in any instance where blade support is referred to, it may be substituted for the term 'tool support' and vice-versa. However, other tools may be contemplated, such as the contents of U.S. Pat. No. 9,707,043 to Bozung, which is hereby incorporated herein by reference. In some examples, the tool 20 may be a drill bit, an ultrasonic vibrating tip, a bur, a stapler, or the like. The tool 20 may comprise the blade assembly and drive motor to cause oscillatory motion of the blade as shown in U.S. Pat. No. 9,820,753 to Walen et al. or U.S. Pat. No. 10,687,823, hereby incorporated herein by reference. Such driving components may comprise a transmission TM coupled to the drive motor M to convert rotary motion from the drive motor M into oscillating motion of the tool 20.

The system and methods described in PCT/US2020/042128, entitled "Robotic Handheld Surgical Instrument Systems and Methods", filed on Jul. 15, 2020, are also hereby incorporated by reference.

Figure 6:
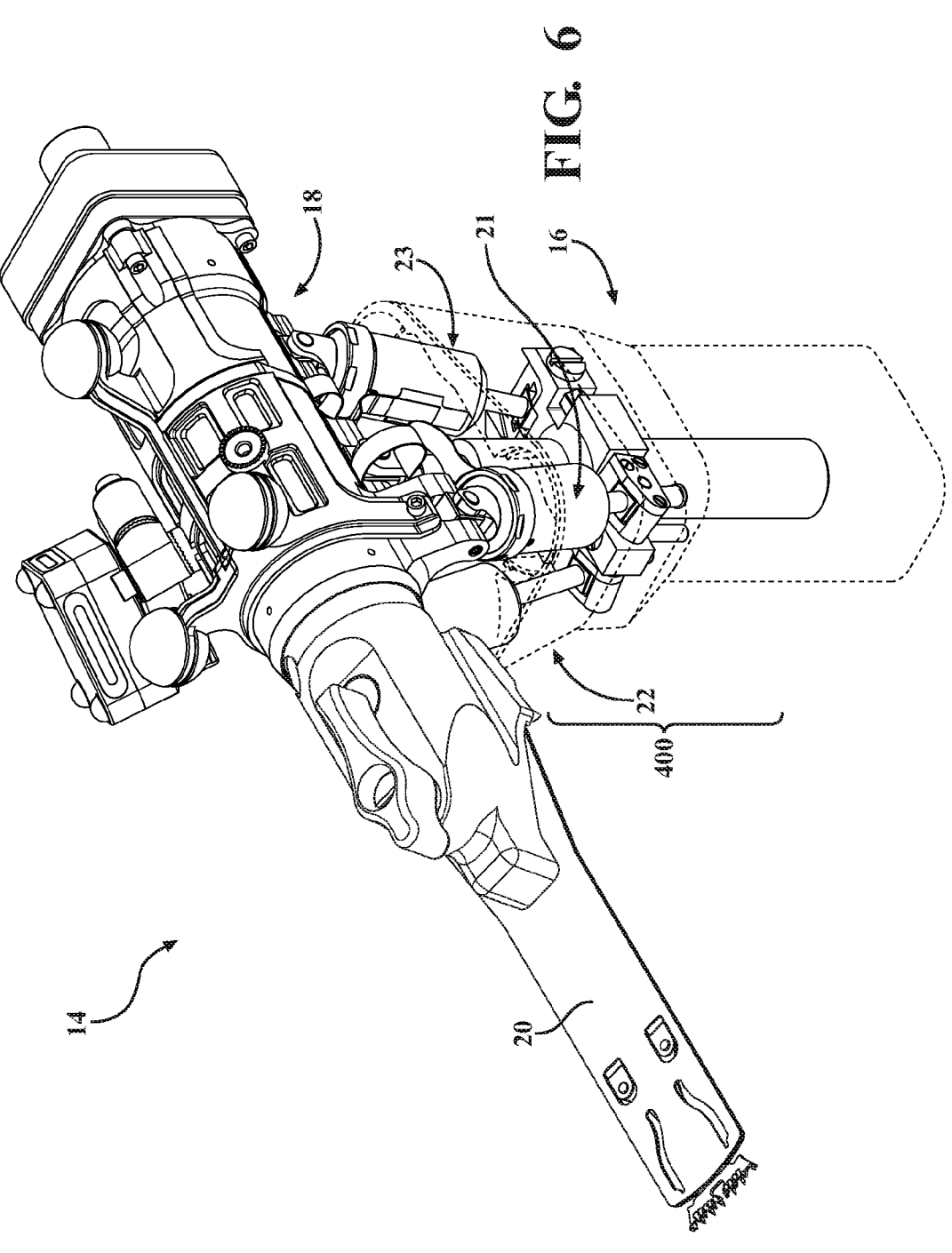
FIG. 6 is a front perspective view of the robotic instrument illustrating one particular pose of a tool support relative to a hand-held portion.

An actuator assembly 400 comprising one or more actuators 21, 22, 23 move the tool support 18 in three degrees of freedom relative to the hand-held portion 16 to provide robotic motion that assists in placing the tool 20 at a desired position or orientation (e.g., at a desired pose relative to the femur F, tibia T, or both during resection), while the user holds the hand-held portion 16. The actuator assembly 400 may comprise actuators 21, 22, 23 that are arranged in parallel, in series, or a combination thereof. In some examples, the actuators 21, 22, 23 move the tool support 18 in three or more degrees of freedom relative to the hand-held portion 16. In some examples, the actuator assembly 400 is configured to move the tool support 18 relative to the hand-held portion 16 in at least two degrees of freedom, such as pitch and z-axis translation. In some examples, such as shown herein, the actuators 21, 22, 23 move the tool support 18 and its associated tool support coordinate system TCS in only three degrees of freedom relative to the hand-held portion 16 and its associated base coordinate system BCS. For example, the tool support 18 and its tool support coordinate system TCS may: rotate about its y-axis to provide pitch motion; rotate about its x-axis to provide roll motion; and translate along an axis Z coincident with a z-axis of the base coordinate system BCS to provide z-axis translation motion. The allowed motions in pitch, roll, and z-axis translation are shown by arrows in FIG. 2 and in the schematic illustrations of FIGS. 3A-3C, 4A-4C, and 5A-5C, respectively. FIG. 6 provides one example of a pose of the tool support 18 and a pose of the hand-held portion 16 within the range of motion of the instrument 14. In some examples, not shown in the figures, actuators may move the tool support 18 in four or more degrees of freedom relative to the hand-held portion 16.

Referring back to FIG. 2, a constraint assembly 24 having a passive linkage 26 may be used to constrain movement of the tool support 18 relative to the hand-held portion 16 in the remaining three degrees of freedom. The constraint assembly 24 may comprise any suitable linkage (e.g., one or more links having any suitable shape or configuration) to constrain motion as described herein. In the example shown in FIG. 2, the constraint assembly 24 operates to limit motion of the tool support coordinate system TCS by: constraining rotation about the z-axis of the base coordinate system BCS to constrain yaw motion; constraining translation in the x-axis direction of the base coordinate system BCS to constrain x-axis translation; and constraining translation in the y-axis direction of the base coordinate system BCS to constrain y-axis translation. The actuators 21, 22, 23 and constraint assembly 24, in certain situations described further below, are controlled to effectively mimic the function of a physical cutting guide, such as a physical saw cutting guide.

Figure 7:
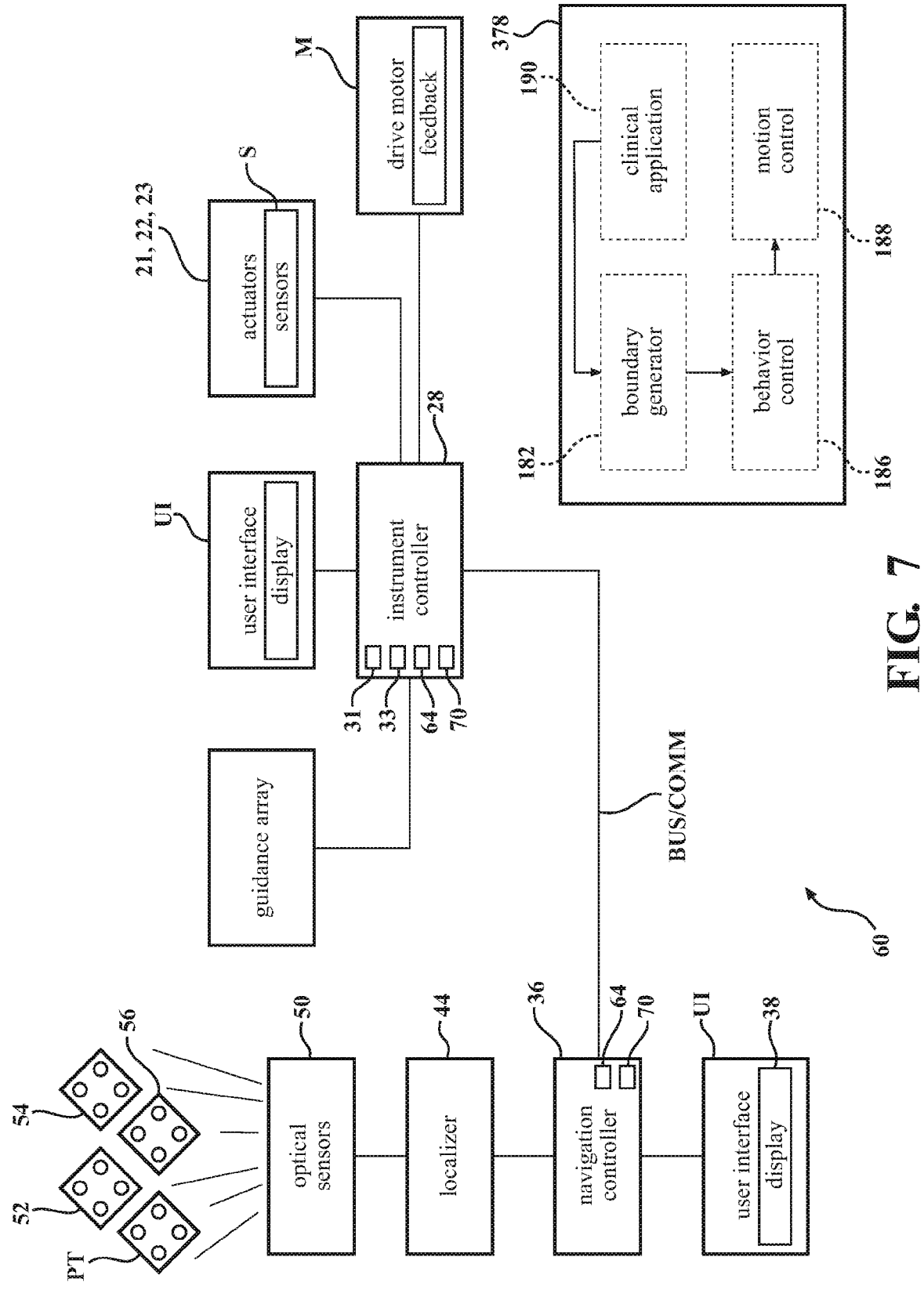
FIG. 7 is a block diagram of a control system, and also illustrates various software modules.

Referring to FIG. 7, the control system may include an instrument controller 28, or other type of control unit, is provided to control the instrument 14. The instrument controller 28 may comprise one or more computers, or any other suitable form of controller that directs operation of the instrument 14 and motion of the tool support 18 (and tool 20) relative to the hand-held portion 16. The instrument controller 28 may have a central processing unit (CPU) or other processors, memory, and storage (not shown). The instrument controller 28 is loaded with software as described below. The processors could include one or more processors to control operation of the instrument 14. The processors can be any type of microprocessor, multi-processor, or multi-core processing system. The instrument controller 28 may additionally, or alternatively, comprise one or more micro-controllers, field programmable gate arrays, systems on a chip, discrete circuitry, or other suitable hardware, software, or firmware that is capable of carrying out the functions described herein. The term processor is not intended to limit any embodiment to a single processor. The instrument 14 may also comprise a user interface UI with one or more displays or input devices (e.g., triggers, push buttons, foot switches, keyboard, mouse, microphone (voice-activation), gesture control devices, touchscreens, etc.).

The control system 60 further includes one or more software programs and software modules. The software modules may be part of the program or programs that operate on the navigation controller 36, instrument controller 28, or both, to process data to assist with control of the robotic system 10. The software programs or modules include computer readable instructions stored in non-transitory memory 64 on the navigation controller 36, instrument controller 28, or both, to be executed by one or more processors 70 of the instrument controller or navigation controller 28, 36. The memory 64 may be any suitable configuration of memory, such as RAM, non-volatile memory, etc., and may be implemented locally or from a remote server. Additionally, software modules for prompting or communicating with the user may form part of the program or programs and may include instructions stored in memory 64 on the navigation controller 36, instrument controller 28, or both. The user may interact with any of the input devices of the navigation user interface UI or other user interface UI to communicate with the software modules. The user interface software may run on a separate device from the navigation controller 36, or instrument controller 28.

The instrument controller 28 controls operation of the tool 20, such as by controlling power to the tool 20 (e.g., to the drive motor M of the tool 20 that controls cutting motion) and controlling movement of the tool support 18 relative to the hand-held portion 16 (e.g., by controlling the actuators 21, 22, 23). The instrument controller 28 controls a state (e.g., position or orientation) of the tool support 18 and the tool 20 with respect to the hand-held portion 16. The instrument controller 28 can control velocity (linear or angular), acceleration, or other derivatives of motion of the tool 20 relative to the hand-held portion 16 or relative to the anatomy that is caused by the actuators 21, 22, 23. For implementations of the visual indicator where the visual indicator is coupled to the tool support or the hand-held portion, the instrument controller may control the visual indicator. However, in some alternatives, a different processor within the control system may control the visual indicator.

As shown in FIG. 2, the instrument controller 28 may comprise a control housing 29 mounted to the tool support 18, or the hand-held portion 16 or a combination thereof with one or more control boards 31 (e.g., one or more printed circuit boards and associated electronic components) located inside the control housing 29. The control boards 31 may comprise microcontrollers, field programmable gate arrays (FPGA), drivers, memory, sensors, or other electronic components for controlling the actuators 21, 22, 23 and the drive motor M (e.g., via motor controllers). The instrument controller 28 may also comprise the control console 33, which may be separate from the instrument, but in data and power communication with the control boards 31. The sensors S, actuators 21, 22, 23, or drive motor M described herein may feed signals to the control boards 31, which transmit data signals out to the console 33 for processing, and the console 33 may feed control commands (e.g. current commands, torque commands, velocity commands, angle commands, position commands, or a combination thereof, as well as various control and configuration parameters) back to the control boards 31 in order to power and control the actuators 21, 22, 23 or the drive motor M. It is contemplated that the processing may also be performed on the control board(s) of the control housing. In some examples, the processing of the control algorithms may be distributed between the console and the control housing. In one example, the position control and velocity control calculations may be in the console and current control may be in the field programmable gate arrays located in the control house. Of course, it is contemplated that no separate control housing is necessary, or the processing can be performed in any number of different locations.

In some versions, the console 33 may comprise a single console for powering and controlling the actuators 21, 22, 23, and the drive motor M. In some versions, the console 33 may comprise one console for powering and controlling the actuators 21, 22, 23 and a separate console for powering and controlling the drive motor M. One such console for powering and controlling the drive motor M may be like that described in U.S. Pat. No. 7,422,582, filed on Sep. 30, 2004, entitled, "Control Console to which Powered Surgical Handpieces are Connected, the Console Configured to Simultaneously Energize more than one and less than all of the Handpieces," hereby incorporated herein by reference. Flexible circuits FC, also known as flex circuits, may interconnect the actuators 21, 22, 23 or other components with the instrument controller 28. For example, flexible circuits FC may be provided between the actuators 21, 22, 23, and the control boards 31. Other forms of connections, wired or wireless, may additionally, or alternatively, be present between components.

Referring briefly back to FIG. 1, the robotic system 10 further includes a navigation system 32. One example of the navigation system 32 is described in U.S. Pat. No. 9,008,757, filed on Sep. 24, 2013, entitled, "Navigation System Including Optical and Non-Optical Sensors," hereby incorporated herein by reference. The navigation system 32 tracks movement of various objects. Such objects include, for example, the instrument 14, the tool 20 and the anatomy, e.g., the femur F and tibia T. The navigation system 32 tracks these objects to gather state information of each object with respect to a (navigation) localizer coordinate system LCLZ. As used herein, the state of an object includes, but is not limited to, data that defines the position, orientation, or both, of the tracked object (e.g., coordinate systems thereof) or equivalents/derivatives of the position, orientation, or both. For example, the state may be a pose of the object, or may include linear velocity data, angular velocity data, and the like.

The navigation system 32 may include a cart assembly 34 that houses a navigation controller 36 or other types of control units. A navigation user interface UI is in operative communication with the navigation controller 36. The navigation user interface UI includes one or more displays 38. The navigation system 32 is capable of displaying graphical representations of the relative states of the tracked objects to the user using the one or more displays 38. The navigation user interface UI further comprises one or more input devices to input information into the navigation controller 36 or otherwise to select/control certain aspects of the navigation controller 36. Such input devices include interactive touchscreen displays. However, the input devices may include any one or more of push buttons, pointer, foot switches, a keyboard, a mouse, a microphone (voice-activation), gesture control devices, and the like. In some examples, the user may use buttons located on the pointer to navigate through icons and menus of the user interfaces UI to make selections, configuring the robotic system 10 or advancing through the workflow. As mentioned below, any of the visual indicators that include display screens may be displayed on the navigation user interface UI, such as on one or more of the displays 38.

The navigation system 32 also includes a localizer 44 coupled to the navigation controller 36. In one example, the localizer 44 is an optical localizer and includes a camera unit 46. The camera unit 46 has an outer casing 48 that houses one or more optical sensors 50. The localizer 44 may comprise its own localizer controller 49 and may further comprise a video camera VC.

The navigation system 32 includes one or more trackers. In some examples, the trackers include a pointer tracker PT, a tool tracker 52, a first patient tracker 54, and a second patient tracker 56. In the illustrated example of FIG. 1, the tool tracker 52 is firmly attached to the instrument 14, the first patient tracker 54 is firmly affixed to the femur F of the patient 12, and the second patient tracker 56 is firmly affixed to the tibia T of the patient 12. In this example, the patient trackers 54, 56 are firmly affixed to sections of bone. The trackers 52, 54, 56 and pointer tracker are registered to their respective objects (e.g. bone, tool) and the navigation system 32 manually, automatically, or a combination thereof. In some examples, the pointer tracker PT is firmly affixed to a pointer 57 and used for registering the anatomy to one or more coordinate systems, including the localizer coordinate system LCLZ or used for other calibration and registration functions. In one example, the pointer 57 may be used to register the patient trackers 54, 56 to the bone which the tracker 54, 56 is attached, respectively, and the tool tracker 52 (and optionally 53) to the tool support 18, the tool 20, the hand-held portion 16, or a combination thereof. In some examples, the pointer tracker PT may be used to register the TCP of the instrument 14 to the tool tracker 52 relative to a tracker coordinate system. This way, if the localizer 44 is moved from position to position, the registration of the instrument 14 is located relative to the tool tracker 52. However, other means of registration of the trackers 52, 54, 56 are contemplated and may be implemented together or separately with the pointer tracker PT. Other tracker locations are also contemplated.

Throughout this description, various transforms are described, such as 'bone to tracker' or 'instrument TCP to tracker', i.e., relative to the 'tracker coordinate system' rather than to the camera coordinate system (C). The localizer coordinate system may be used as an intermediate coordinate system during registration and bone prep, since all tracked objects are measured with respect to C. During registration, ultimately the various localizer-referred poses are combined mathematically, and registration results are stored 'with respect to a tracker', such that if the camera (i.e., C) moves, the registration is still valid.

The tool tracker 52 may be affixed to any suitable component of the instrument 14, and in some versions may be attached to the hand-held portion 16, the tool support 18, directly to the tool 20, or a combination thereof. The trackers 52, 54, 56, PT may be fixed to their respective components in any suitable manner, such as by fasteners, clamps, or the like. For example, the trackers 52, 54, 56, PT may be rigidly fixed, flexibly connected (optical fiber), or not physically connected at all (ultrasound), as long as there is a suitable (supplemental) way to determine the relationship (measurement) of that respective tracker to the associated object. Any one or more of the trackers 52, 54, 56, PT may include active markers 58. The active markers 58 may include light emitting diodes (LEDs). Alternatively, the trackers 52, 54, 56, PT may have passive markers, such as reflectors, which reflect light emitted from the camera unit 46. Printed markers, or other suitable markers not specifically described herein, may also be utilized.

Various coordinate systems may be employed for purposes of tracking the objects. For instance, the coordinate systems may comprise the localizer coordinate system C, the tool support coordinate system TCS, the base coordinate system BCS, coordinate systems associated with each of the trackers 52, 54, 56, PT, one or more coordinate systems associated with the anatomy, one or more coordinate systems associated with pre-operative or intra-operative images (e.g., CT images, MRI images, etc.) or models (e.g., 2D or 3D models) of the anatomy—such as the implant coordinate system, and a TCP (tool center point) coordinate system. In some examples, the robotic system 10 does not rely on pre-operative or intraoperative imaging to create the 2D or 3D models of the target bone. Rather, the robotic system may be used in an imageless system using the pointer tracker PT to register the target anatomy, capturing various anatomical landmarks, which is then processed by the control system 60 to morph a nominal bone model to match the captured data. In other examples, pre-operative and intra-operative imaging is used to image the target area of the patient and then transform the 2D or 3D images into a 3D model of the target bone. It is also contemplated that the robotic system 10 may use a combination of imaged and imageless procedures in creating a 3D model of the target surgical area. One exemplary system is described in U.S. Pat. No. 8,617,174, which is hereby incorporated by reference. Coordinates in the various coordinate systems may be transformed to other coordinate systems using transformations upon establishing relationships between the coordinate systems, e.g., via registration, calibration, geometric relationships, measuring, etc.

As shown in FIG. 2, in some examples, the TCP is a predetermined reference point or origin of the TCP coordinate system defined at the distal end of the tool 20. The geometry of the tool 20 may be defined relative to the TCP coordinate system or relative to the tool support coordinate system TCS. The tool 20 may comprise one or more geometric features, e.g., perimeter, circumference, radius, diameter, width, length, height, volume, area, surface/plane, range of motion envelope (along any one or more axes), etc. defined relative to the TCP coordinate system or relative to the tool support coordinate system TCS and stored in the non-volatile memory of the control boards 31 in the control housing 29 of the instrument 14, the navigation system 32, the instrument controller 28, or a combination thereof. The tool center point (TCP), in one example, is a predetermined reference point and corresponding coordinate system defined at the tool 20. The TCP has a known, or able to be calculated (i.e., not necessarily static), pose relative to other coordinate systems. The TCP coordinate system includes an origin point and a set of axes (e.g. x axis, y axis, z axis) which define the pose of the TCP. By tracking the TCP (or knowing the pose of the TCP), the robotic system 10 may calculate the position and orientation of the instrument 14 based on the pose of the TCP and the known positional relationship between the TCP and the features of the instrument 14. In some examples, the tool 20 has a blade plane (e.g., for saw blades) that will be described for convenience and ease of illustration but is not intended to limit the tool 20 to any particular form. Points, other primitives, meshes, other 3D models, etc., can be used to virtually represent the tool 20. The origin point of the TCP coordinate system may be located at the spherical center of the bur of the tool 20 or at the distal end of the saw blade 27 such that the TCP coordinate system is tracked relative to the origin point on the distal tip of the tool 20. Alternatively, the TCP may be tracked using a plurality of tracked points. The TCP may be defined in various ways depending on the configuration of the tool 20. The instrument may employ the joint/motor encoders, or any other non-encoder position sensing method, so the control system 60 may determine a pose or position of the TCP relative to the hand-held portion 16 and BCS. The tool support 18 may use joint measurements to determine TCP pose or could employ techniques to measure TCP pose directly. The control of the tool 20 is not limited to a center point. For example, any suitable primitives, meshes, etc., can be used to represent the tool 20. It should be appreciated that the TCP may alternatively be defined as a point, as opposed to a coordinate system. The TCP coordinate system allows calculate any required reference points or geometry aspects of the tool once you have determined the pose of the saw blade or other tool.

The TCP coordinate system, the tool support coordinate system TCS, and the coordinate system of the tool tracker 52 may be defined in various ways depending on the configuration of the tool 20. For example, the pointer 57 may be used with calibration divots CD in the tool support 18 or in the tool 20 for: registering (calibrating) a pose of the tool support coordinate system TCS relative to the coordinate system of the tool tracker 52; determining a pose of the TCP coordinate system relative to the coordinate system of the tool tracker 52; or determining a pose of the TCP coordinate system relative to the tool support coordinate system TCS. Other techniques could be used to measure the pose of the TCP coordinate system directly, such as by attaching and fixing one or more additional trackers/markers directly to the tool 20. In some versions, trackers/markers may also be attached and fixed to the hand-held portion 16, the tool support 18, or both. In instances where the hand-held portion includes a tracker, the pose of the hand-held portion relative to the localizer/camera coordinate system LCTZ may be measured directly. In still other alternatives, the TCP may be defined relative to the tool tracker, using the intermediate tool support coordinate system TCS.

Since the tool support 18 is movable in multiple degrees of freedom relative to the hand-held portion 16 via the actuators 21, 22, 23, the instrument 14 may employ encoders, hall-effect sensors (with analog or digital output), or any other position sensing method, to measure a pose of the TCP coordinate system or tool support coordinate system TCS relative to the base coordinate system BCS. In one example, the instrument 14 may use measurements from sensors that measure actuation of the actuators 21, 22, 23 to determine a pose of the TCP coordinate system or tool support coordinate system TCS relative to the base coordinate system BCS, as described further below.

The localizer 44 monitors the trackers 52, 54, 56, PT (e.g., coordinate systems thereof) to determine a state of each of the trackers 52, 54, 56, PT, which correspond respectively to the state of the object respectively attached thereto. The localizer 44 may perform known techniques to determine the states of the trackers 52, 54, 56, PT, and associated objects (such as the tool, the patient, the tool support, and the hand-held portion). The localizer 44 provides the states of the trackers 52, 54, 56, PT to the navigation controller 36. In some examples, the navigation controller 36 determines and communicates the states of the trackers 52, 54, 56, PT to the instrument controller 28.

The navigation controller 36 may comprise one or more computers, or any other suitable form of controller. Navigation controller 36 has a central processing unit (CPU) or other processors, memory, and storage (not shown). The processors can be any type of processor, microprocessor, or multi-processor system. The navigation controller 36 is loaded with software. The software, for example, converts the signals received from the localizer 44 into data representative of the position or orientation of the objects being tracked. The navigation controller 36 may additionally, or alternatively, comprise one or more microcontrollers, field programmable gate arrays, systems on a chip, discrete circuitry, or other suitable hardware, software, or firmware that is capable of carrying out the functions described herein. The term processor is not intended to limit any embodiment to a single processor.

Although one example of the navigation system 32 is shown to determine object states, the navigation system 32 may have any other suitable configuration for tracking the instrument 14, tool 20, or the patient 12. In another example, the navigation system 32 or localizer 44 are ultrasound-based. For example, the navigation system 32 may comprise an ultrasound imaging device coupled to the navigation controller 36. The ultrasound imaging device images any of the aforementioned objects, e.g., the instrument 14, the tool 20, or the patient 12, and generates state signals to the navigation controller 36 based on the ultrasound images. The ultrasound images may be 2D, 3D, or a combination of both. The navigation controller 36 may process the images in near real-time to determine states of the objects. The ultrasound imaging device may have any suitable configuration and may be different than the camera unit 46 as shown in FIG. 1.

In another example, the navigation system 32 or localizer 44 are radio frequency (RF)-based. For example, the navigation system 32 may comprise an RF transceiver coupled to the navigation controller 36. The instrument 14, the tool 20, or the patient 12 may comprise RF emitters or transponders attached thereto. The RF emitters or transponders may be passive or actively energized. The RF transceiver transmits an RF tracking signal and generates state signals to the navigation controller 36 based on RF signals received from the RF emitters. The navigation controller 36 may analyze the received RF signals to associate relative states thereto. The RF signals may be of any suitable frequency. The RF transceiver may be positioned at any suitable location to track the objects using RF signals effectively. Furthermore, the RF emitters or transponders may have any suitable structural configuration that may be much different than the trackers 52, 54, 56, PT shown in FIG. 1.

In yet another example, the navigation system 32 or localizer 44 are electromagnetically based. For example, the navigation system 32 may comprise an EM transceiver coupled to the navigation controller 36. The instrument 14, the tool 20, or the patient 12 may comprise EM components attached thereto, such as any suitable magnetic tracker, electromagnetic tracker, inductive tracker, or the like. The trackers may be passive or actively energized. The EM transceiver generates an EM field and generates state signals to the navigation controller 36 based upon EM signals received from the trackers. The navigation controller 36 may analyze the received EM signals to associate relative states thereto. Again, the navigation system 32 examples may have structural configurations that are different than the navigation system 32 configuration shown in FIG. 1.

The navigation system 32 may have any other suitable components or structure not specifically recited herein. Furthermore, any of the techniques, methods, or components described above with respect to the navigation system 32 shown may be implemented or provided for any of the other examples of the navigation system 32 described herein. For example, the navigation system 32 may utilize solely inertial tracking or any combination of tracking techniques, and may additionally or alternatively comprise, fiber optic-based tracking, machine-vision tracking, and the like.

Referring to FIG. 7, the robotic system 10 includes a control system 60 that comprises, among other components, the instrument controller 28 and the navigation controller 36. The control system 60 further includes one or more software programs and software modules. The software modules may be part of the program or programs that operate on the instrument controller 28, navigation controller 36, or a combination thereof, to process data to assist with control of the robotic system 10. The software programs or modules include computer readable instructions stored in memory 64 on the instrument controller 28, navigation controller 36, or a combination thereof, to be executed by one or more processors 70 of the instrument controllers 28. The memory 64 may be any suitable configuration of memory, such as non-transitory memory, RAM, non-volatile memory, etc., and may be implemented locally or from a remote database. Additionally, software modules for prompting or communicating with the user may form part of the program or programs and may include instructions stored in memory 64 on the instrument controller 28, navigation controller 36, or a combination thereof. The user may interact with any of the input devices of the navigation user interface UI or other user interface UI to communicate with the software modules. The user interface software may run on a separate device from the instrument controller 28 or navigation controller 36. The instrument 14 may communicate with the instrument controller 28 via a power, data connection, or both. The power connection, data connection, or both may provide a path for the input and output used to control the instrument 14 based on the position and orientation data generated by the navigation system 32 and transmitted to the instrument controller 28, as shown as the BUS/COMM connection 37 in FIG. 7.

The control system 60 may comprise any suitable configuration of input, output, and processing devices suitable for carrying out the functions and methods described herein. The control system 60 may comprise the instrument controller 28, the navigation controller 36, or a combination thereof, or may comprise only one of these controllers, or additional controllers. The controllers may communicate via a wired bus or communication network as shown in one example as the BUS/COMM connection 37 in FIG. 7, via wireless communication, or otherwise. The control system 60 may also be referred to as a controller. The control system 60 may comprise one or more microcontrollers, field programmable gate arrays, systems on a chip, discrete circuitry, sensors, displays, user interfaces, indicators, or other suitable hardware, software, or firmware that is capable of carrying out the functions described herein.

Instrument

Figure 8:
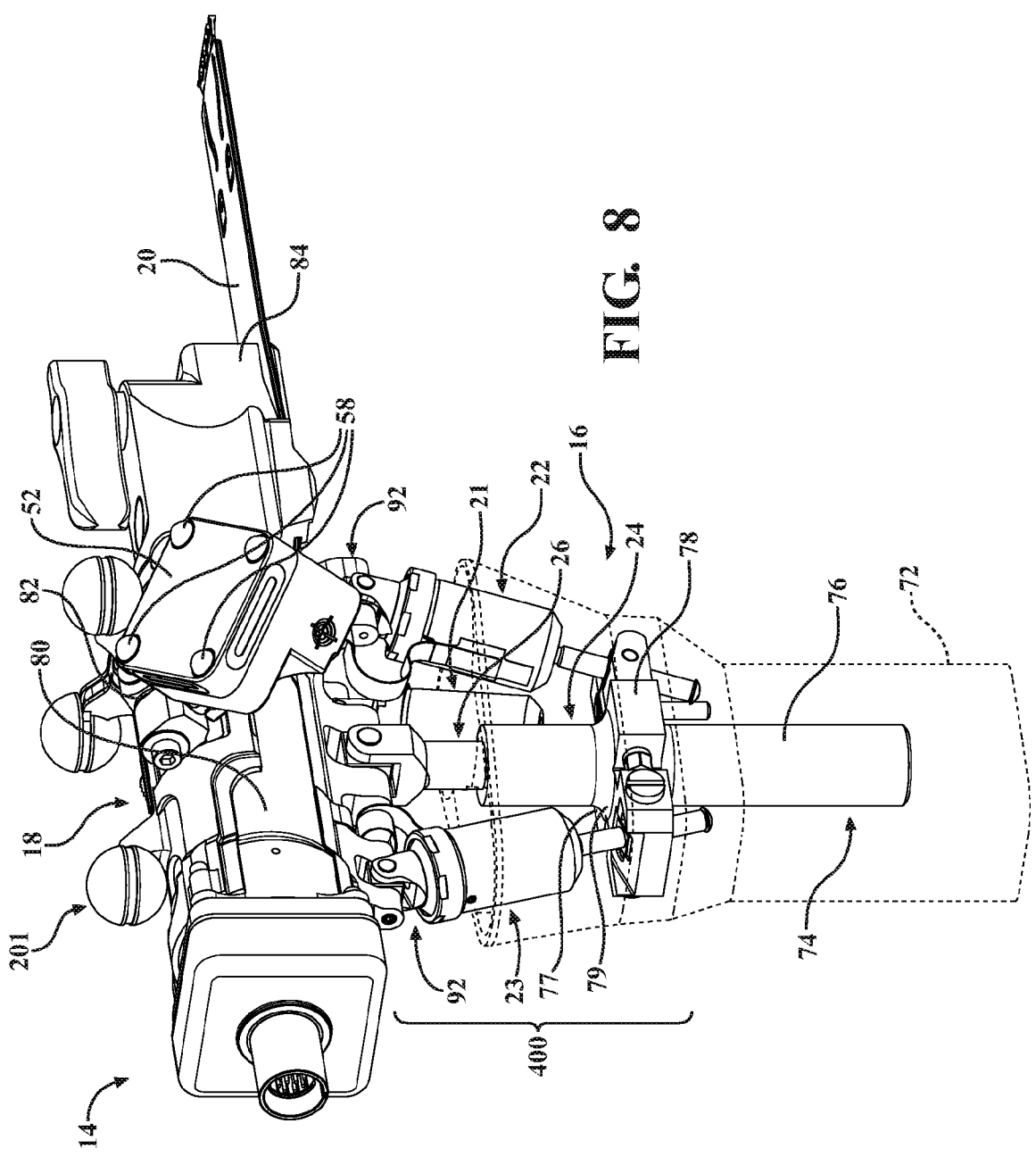
FIG. 8 is a rear perspective view of the robotic instrument.
Figure 9:
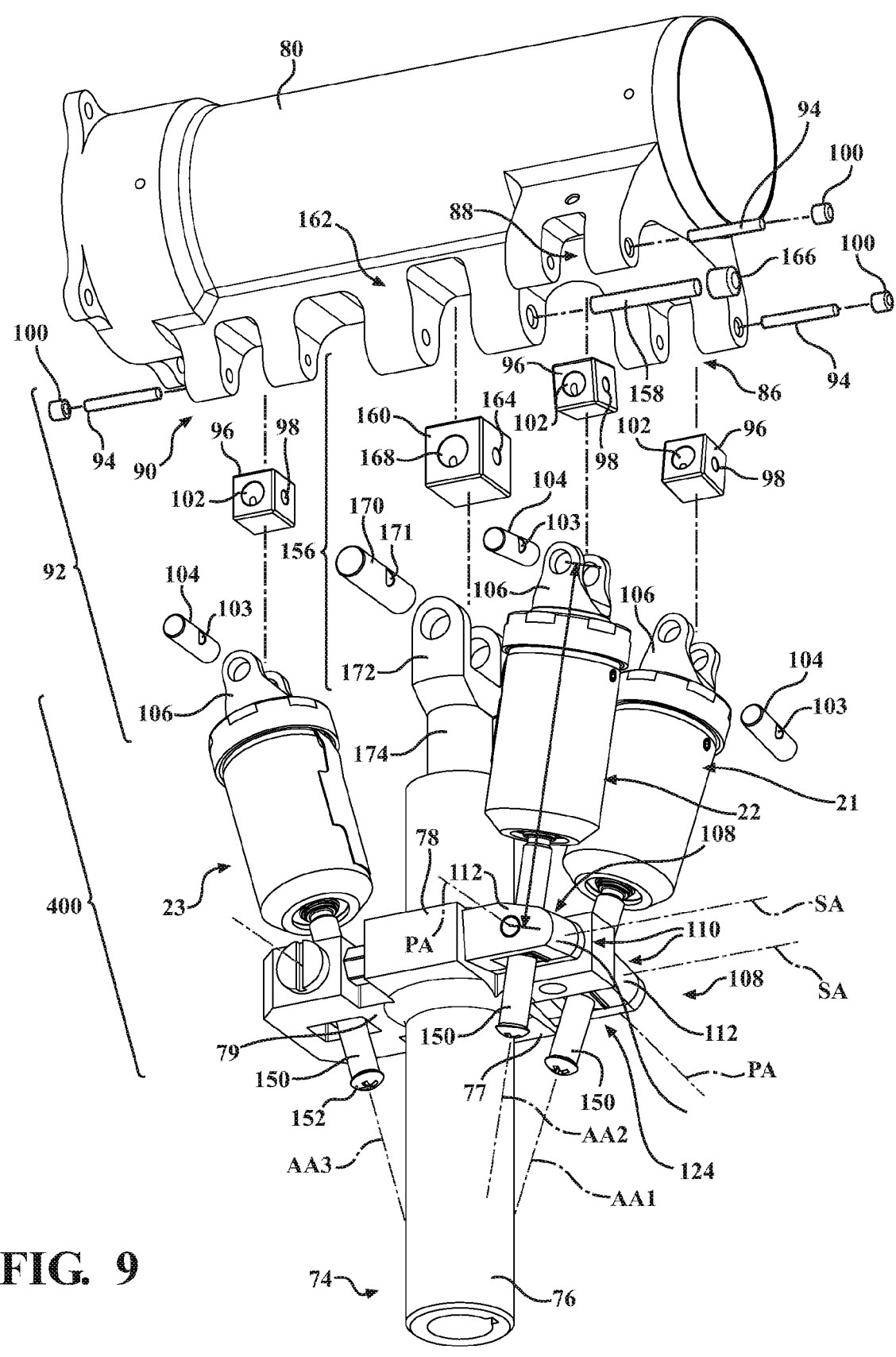
FIG. 9 is a side exploded view of the robotic instrument.

In one exemplary configuration, one exemplary instrument 14 is best shown in FIGS. 8 and 9. The instrument 14 includes the hand-held portion 16 to be held by the user, the tool support 18 movably coupled to the hand-held portion 16 to support the tool 20, the actuator assembly 400 with the plurality of actuators 21, 22, 23 operatively interconnecting the tool support 18 and the hand-held portion 16 to move the tool support 18 in at least three degrees of freedom relative to the hand-held portion 16, and the constraint assembly 24 having the passive linkage 26 operatively interconnecting the tool support 18 and the hand-held portion 16. While a particular robotic instrument is described throughout the figures, the visual indicators described herein may be used within any multiple degree of freedom robotic surgical instrument, including those that have different degrees of freedom that the instrument 14.

The hand-held portion 16 often comprises a grip 72 for being grasped by the user so that the user is able to manipulate, guide, or grasp the instrument 14. The hand-held portion 16 may be configured with ergonomic features such as a grip for a hand of a user to hold, a textured or mixed material coating for preventing a user's hand from slipping when wet or bloody. The hand-held portion 16 may include a taper to accommodate users with different hand sizes and contoured to mate with the contours of a user's hand or fingers. The hand-held portion 16 also comprises a base 74 to which the grip 72 is attached by one or more fasteners, adhesive, welding, or the like. In the version shown, the base 74 comprises a sleeve 76 having a generally hollow cylindrical shape. Joint supports 77, 78, 79 extend from the sleeve 76. The actuators 21, 22, 23 may be movably coupled to the base 74 at the joint supports 77, 78, 79 via joints described further below.

The tool support 18 comprises a tool support body 80 to which the tool tracker 52 can be fixed to or removably mounted via one or more tracker mounts fixed to the tool support 18 at one or more mounting locations 82. In one example, the tool tracker 52 is integrated with the tool support 18. In another example, the tool tracker 52 is removably mounted at the one or more mounting locations 82. The tool 20 is removably coupled to the tool support 18 in the version shown. In particular, the tool support 18 comprises a tool coupler, such as head 84 to which the tool 20 is mounted, as described in U.S. Pat. No. 9,820,753 to Walen et al., incorporated herein by reference. The head 84 may be configured to utilize an oscillating-style of saw blade, as well as a sagittal-style saw blade or saw blade cartridge. The drive motor M that drives operation of the tool 20 is disposed in the tool support body 80 (e.g., to drive oscillation of the saw blade in some versions). The tool 20 may be attached to and released from the head 84 in the manner disclosed in U.S. Pat. No. 9,820,753 to Walen et al., incorporated herein by reference. As best shown in FIG. 9, the tool support 18 also comprises a plurality of actuator mounts 86, 88, 90 at which the actuators 21, 22, 23 are to be movably coupled to the tool support 18 via joints, as described further below. The actuator mounts 86, 88, 90 may comprise brackets, or the like, suitable to mount the actuators 21, 22, 23 such that the tool support 18 is able to move in at least three degrees of freedom relative to the hand-held portion 16.

The actuators 21, 22, 23, in the version shown, comprise electric, linear actuators that extend between the base 74 and the tool support body 80. When actuated, an effective length of the actuator 21, 22, 23 changes to vary a distance between the tool support body 80 and the base 74 along a corresponding axis of the actuator 21, 22, 23. Accordingly, the control system 60 commands the actuators 21, 22, 23 to work in a coordinated fashion, responding to individual inputs given to each actuator 21, 22, 23, respectively, by the control system 60 to change their effective lengths and move the tool support 18 in at least three degrees of freedom relative to the hand-held portion 16 into the target pose. In the version shown, three actuators 21, 22, 23 are provided, and may be referred to as first, second, and third actuators 21, 22, 23 or front actuators 21, 22, and rear actuator 23. The first, second, and third actuators 21, 22, 23 are adjustable in effective length along a first active axis AA1, a second active axis AA2, and a third active axis AA3 (see FIG. 9). The first, second, and third actuators 21, 22, 23 are independently adjustable in effective length to adjust one or more of a pitch orientation, a roll orientation, and a z-axis translation position of the tool support 18 relative to the hand-held portion 16, as previously described. More actuators may be provided in some examples. The actuators may comprise rotary actuators in some examples. The actuators 21, 22, 23 may comprise linkages having one or more links of any suitable size or shape. The actuators 21, 22, 23 may have any configuration suitable to enable movement of the tool support 18 relative to the hand-held portion 16 in at least three degrees of freedom. For example, in some versions, there may be one front actuator and two rear actuators, or some other arrangement of actuators.

In this version, the actuators 21, 22, 23 are coupled to the base 74 and the tool support body 80 via a plurality of active joints. The active joints include a set of first active joints 92 that couple the actuators 21, 22, 23 to the tool support body 80 at the actuator mounts 86, 88, 90. In one version, as shown in FIG. 9, the first active joints 92 comprises active U-joints. The U-joints comprise first pivot pins 94 and joint blocks 96. The first pivot pins 94 pivotally connect the joint blocks 96 to the actuator mounts 86, 88, 90 via throughbores 98 in the joint blocks 96. Set screws 100 may secure the first pivot pins 94 to the actuator mounts 86, 88, 90. The U-joints may also comprise second pivot pins 104. The joint blocks 96 have crossbores 102 to receive the second pivot pins 104. The second pivot pins 104 have throughbores 103 to receive the first pivot pins 94, such that the first pivot pins 94, the joint blocks 96, and the second pivot pins 104 form a cross of the U-joint. The first pivot pin 94 and the second pivot pin 104 of each U-joint define pivot axes PA that intersect. The second pivot pins 104 pivotally connect a pivot yoke 106 of the actuators 21, 22, 23 to the joint blocks 96. As a result, the actuators 21, 22, 23 are able to move in two degrees of freedom relative to the tool support body 80. Other types of active joints are also contemplated, such as active spherical joints comprising balls with slots that receive pins.

Referring to FIG. 9, the active joints also comprise a set of second active joints 108 coupling the front two actuators 21, 22 to the base 74 of the hand-held portion 16. In the version shown, the second active joints 108 are supported at the joint supports 77, 78. Each of the second active joints 108 comprises a swivel yoke 110 arranged to swivel relative to the base 74 of the hand-held portion 16 about a swivel axis SA. Each swivel yoke 110 has a swivel head 112 and a post 114 extending from the swivel head 112 to pivotally engage the base 74 at one of the joint supports 77, 78. Nuts 115 threadably connect to one end of the posts 114 to trap the posts 114 in the base 74 while allowing the respective swivel yoke 110 to freely rotate within its respective joint support 77, 78.

Each of the second active joints 108 comprises a carrier 116 pivotally coupled to one of the swivel yokes 110. The carriers 116 have internally threaded throughbores 117 to receive lead screws 150 of the front two actuators 21, 22, as described further below. Each of the carriers 116 also comprises opposed trunnions 118 that allow the carriers 116 to pivot relative to the swivel yokes 110 about pivot axes PA (see FIG. 9) by being seated in pockets in the swivel yokes 110. In some versions, for each of the second active joints 108, the swivel axis SA intersects the pivot axis PA to define a single vertex about which the actuators 21, 22 move in two degrees of freedom.

Covers are fastened to the swivel heads 112 and define one of the pockets, while the swivel head 112 defines the other pocket. During assembly, the carriers are first positioned with one of the trunnions placed in the pocket in the swivel head 112, and the cover is then fastened over the other trunnion such that the carrier is captured between the cover and the swivel head 112 and is able to pivot relative to the swivel yoke 110 via the trunnions and pockets. Owing to the configuration of the swivel yokes 110 and the associated carriers, i.e., the carriers ability to swivel about the swivel axes SA and pivot about the pivot axes PA, the second active joints 108 allow two degrees of freedom of movement of the front two actuators 21, 22 relative to the base 74. Other joint arrangements between the front two actuators 21, 22 and the base 74 are also possible.

The active joints also comprise a third active joint 124 coupling the rear (third) actuator 23 to the base 74 of the hand-held portion 16. In the version shown, the third active joint 124 is supported at the joint support 79. The third active joint 124 comprises a pivot housing 126 fixed to the joint support 79 of the base 74.

The third active joint 124 comprises a carrier pivotally coupled to the pivot housing 126 via trunnions. Fasteners having pockets attach to either side of the pivot housing 126 via throughbores to engage the trunnions. The fasteners are arranged such that the carrier is able to pivot via the trunnions being located in the pockets after assembly. The carrier has an internally threaded throughbore to receive a lead screw 150 of the rear actuator 23, as described further below. Owing to the configuration of the pivot housing 126 and associated carrier, i.e., the ability of the associated carrier to only pivot about the pivot axis PA (e.g., and not swivel), the third active joint 124 allows only one degree of freedom of movement of the rear actuator 23 relative to the base 74. Other joint arrangements between the rear actuator 23 and the base 74 are also possible.

Each of the actuators 21, 22, 23 comprises a housing. The housing comprises a canister and a cap threadably connected to the canister. The pivot yokes 106 that form part of the first active joints 92 are fixed to the housings such that the housings and pivot yokes 106 are able to move together relative to the tool support 18 via the first active joints 92. The caps capture annular shoulders of the pivot yokes 106 to secure the pivot yokes 106 to the canisters.

In some versions, the pivot yokes 106 and canisters comprise one or more alignment features to align each pivot yoke 106 to its respective canister in a predefined, relative orientation. Such alignment features may comprise mating portions, keys/keyways, or the like. During assembly, the pivot yoke 106 may first be secured to the canister in its predefined, relative orientation, and the cap may then be threaded onto the canister (e.g., via mating outer and inner threads) to trap the pivot yoke 106 to the canister at the predefined, relative orientation. This predefined relationship may be helpful in routing or aligning the flex circuits FC, preventing rolling of the pivot yoke 106 relative to the canister, or for other purposes.

Each of the actuators 21, 22, 23 also comprises a motor disposed in each housing. The motor has a casing disposed in the housing and a motor winding assembly disposed within the casing. The motor winding assembly may also be aligned in a predefined, relative orientation to the canister, such as via a set screw or other alignment feature, such as those described above. Each motor also has a rotor fixed to the lead screw 150. The lead screw 150 is supported for rotation in the housing by one or more bushings or bearings. The rotor and associated lead screw 150 are configured to rotate relative to the housing upon selective energization of the motor. The lead screws 150 have fine pitch and lead angles to prevent backdriving (i.e., they are self-locking). As a result, a load placed on the tool 20 does not easily back drive the motor. In some examples, the lead screws 150 have an 8-36 class 3 thread that results in a lead of from 0.02 to 0.03 inches/revolution. Other thread types or sizes may also be employed.

Each of the actuators 21, 22, 23 may be controlled by a separate motor controller. Motor controllers may be wired separately to the actuators 21, 22, 23, respectively, to individually direct each actuator 21, 22, 23 to a given target position. In some examples, the motor controllers are proportional integral derivative (PID) controllers. In some examples, the motor controllers may include cascaded control loops relating to position, velocity, and torque (current). Additionally, or alternatively, the motor controller may only include of a torque (current) control loop. In another example, the position control loop may directly feed the torque (current) control loop. Each of these control stages may be implemented as a PID controller, state space controller, or utilize alternate or additional control techniques (e.g., velocity feedforward, torque feedforward, etc.). In some cases, the torque (current) control loop is implemented using field-oriented control and space vector modulation. The stages of the control loop could be distributed between various components of the system. In some examples, the position loop and velocity loop are implemented in the instrument controller and the torque control loop is implemented directly in the control boards 31 as part of the control housing 29 on the instrument 14, mitigating the impact of data communication latency from the instrument 14 through the connection to the console 33, since the current control loop does not require any data feedback via the console 33. The position control loop and velocity control loop are not as sensitive to the communication latency and can be implemented in the console 33. In some examples, the motor controllers can be integrated with or form part of the instrument controller 28. For ease of illustration, the motor controllers shall be described herein as being part of the instrument controller 28.

A power source provides, for example, 32 VDC power signals to the motors via the console 33. The 32 VDC signal is applied to the motors through the instrument controller 28. The instrument controller 28 selectively provides the power signal to each motor to selectively activate the motors. This selective activation of the motors is what positions the tool 20. The motors may be any suitable type of motor, including brushless DC servomotors, permanent magnet synchronous motors, other forms of DC motors, or the like. The power source also supplies power to the instrument controller 28 to energize the components internal to the pinstrument controller 28. In some examples, the actuator motor may be a 3-phase, brushless motor. The actuator motor may be a DC motor. The actuator motor may be a permanent magnet synchronous motor. Each of the actuator motors may be configured with a sinusoidal back-EMF, configured to achieve limited mechanical cogging, allowing smooth and particular motion, limiting torque ripple. However, other motor types are contemplated. It should be appreciated that the power source can provide other types of power signals such as, for example, 12 VDC, 24 VDC, 40 VDC, etc. The instrument may use electronic switches, e.g., MOSFETs or GaN FETs to PWM the voltage signals to the 3-phase motor on/off at a high frequency, e.g., typically at a rate of at least 16 kHz, up to 256 kHz or higher.

In one possible implementation, one or more sensors S (see also FIG. 7) transmit signals back to the instrument controller 28 so that the instrument controller 28 can determine a current position or angle of the associated actuator 21, 22, 23 (i.e., a measured position). The levels of these signals may vary as a function of the rotational position of the associated rotor. In one implementation, the sensor(s) S may resolve the rotational position of the rotor within a given turn at a high resolution. These sensors S may be Hall-effect sensors that output analog or digital signals based on the sensed magnetic fields from the rotor, or from other magnets placed on the lead screw 150 (e.g., the 2-pole magnet A low voltage signal, e.g., 5 VDC, for energizing the Hall-effect sensors may be supplied from the motor controller associated with the motor with which the Hall-effect sensors are associated. In some examples, two Hall-effect sensors are disposed in the housing and spaced 90 degrees apart from each other around the rotor to sense joint position so that the instrument controller 28 is able to determine the position and count incremental turns of the rotor). In some versions, the Hall-effect sensors output digital signals represents incremental counts. Various types of motors and sensor arrangements are possible. In some examples, the motors are brushless DC servomotors and two or more internal Hall-effect sensors may be spaced 90 degrees, 120 degrees, or any other suitable spacing from each other around the rotor. The sensors S may also comprise absolute or incremental encoders, which may be used to detect a rotational position of the rotor and to count turns of the rotor. Other type of encoders may be also used as the one or more sensors. The sensors may be placed at any suitable location on the actuator and its surrounding components suitable to determine the position of each actuator as it is adjusted, such as on the housing, nut, screw, etc. In yet another configuration, sensorless motor control may be utilized. In such an implementation, the position of each rotor may be determined by measuring the motor's back-emf or inductance. One suitable example may be found in U.S. Pat. No. 7,422,582, which is hereby incorporated by reference in its entirety.

In some examples, the sensors or encoders may measure position feedback for joint position control or to determine the position of the tool support 18 relative to the hand-held portion 16 when used in conjunction with a kinematic model of the instrument 14. In some examples, the sensors or encoders rely on a multi-turn measurement, which accumulates from revolution to the next, used to determine an absolute position of the actuator 21, 22, 23 along its axis and is used in conjunction with the known pitch (i.e. revolutions per inch of the leadscrew). Additionally, or alternatively, the sensors or encoders may be used to determine the "electrical angle of the rotor" for use in electronic commutation of the motor. For example, the sensors or encoders may be used to determine a rotor position and apply appropriate energization signals to achieve optimal (efficient) torque generation. In this example, the sensors or encoders may utilize a single turn or sub-turn (within one electrical revolution) measurement that rolls over each electrical revolution. The number of electrical revolutions is equal to the number of mechanical revolutions divided by the number of magnetic poles of the motor (e.g. number of pole pairs). However, it is contemplated that a sensor-less method be implemented.

In some examples, output signals from the Hall-effect sensors are sent to the instrument controller 28. The instrument controller 28 monitors the received signals for changes in their levels. Based on these signals the instrument controller 28 determines joint position. Joint position may be considered the degrees of rotation of the rotor from an initial or home position. The rotor can undergo plural 360° rotations. The joint position can therefore exceed 360°. A scalar value referred to as a count is representative of joint position from the home position. The rotors rotate in both clockwise and counterclockwise directions. Each time the signal levels of the plural signals (analog or digital) undergo a defined state change, the instrument controller 28 increments or decrements the count to indicate a change in joint position. For every complete 360° rotation of the rotor, the instrument controller 28 increments or decrements the value of the count by a fixed number of counts. In some examples, the count is incremented or decremented between 100 and 3,000 per 360-degree revolution of the rotor. In some examples, there are 1,024 positions (counts) per 360-degree revolution of the rotor, such as when an incremental encoder is used to monitor joint position. Internal to the instrument controller 28 is a counter associated with each actuator 21, 22, 23. The counter stores a value equal to the cumulative number of counts incremented or decremented. The count value can be positive, zero or negative. In some versions, the count value defines incremental movement of the rotor. Accordingly, the rotors of the actuators 21, 22, 23 may first be moved to known positions, referred to as their home positions (described further below), with the count values being used thereafter to define the current positions of the rotors.

As previously described, the carriers have the internally threaded throughbores to threadably receive the lead screws 150 so that each of the lead screws 150 can rotate relative to a corresponding one of the carriers to adjust the effective length of a corresponding one of the plurality of actuators 21, 22, 23 and thereby vary the counts measured by the instrument controller 28. Each of the housings and corresponding carriers are constrained from relative movement in at least one degree of freedom to allow the lead screws 150 to rotate relative to the carriers. More specifically, the lead screws 150 are able to rotate relative to the carriers owing to: the pivot yokes 106 being unable to rotate about the associated active axes AA1, AA2, AA3 (i.e., the pivot yokes 106 are limited from such rotational movement by virtue of the configuration of the first active joints 92); and the carriers being unable to rotate about the associated active axes AA1, AA2, AA3 (i.e., the carriers are limited from such rotational movement by virtue of the configuration of the second active joints 108 and the third active joint 124).

Stops 152, such as threaded fasteners and shoulders formed on the lead screws 150, are fixed to the lead screws 150. The stops 152 are sized to abut the carriers 116 at ends of travel of each lead screw 150.

As previously described, the actuators 21, 22, 23 are actively adjustable in effective length to enable movement of the tool support 18 relative to the hand-held portion 16. One example of this effective length is labeled "EL" on the third actuator 23. Here, the effective length EL is measured from the pivot axis PA to a center of the associated first active joint 92. As each actuator 21, 22, 23 is adjusted, the effective length EL changes, by varying how far the lead screw 150 has been threaded into or out of its associated carrier and thereby changing the distance from the center of the associated carrier to the center of the associated first active joint 92. The actuators 21, 22, 23 are adjustable between minimum and maximum values of the effective length EL. The effective length EL of each actuator 21, 22, 23 can be represented or measured in any suitable manner to denote the distance between the tool support 18 and the hand-held portion 16 along the active axes AA1, AA2, AA3 that changes to cause various movements of the tool support 18 relative to the hand-held portion 16.

The constraint assembly 24 works in concert with the actuators 21, 22, 23 to constrain the movement provided by the actuators 21, 22, 23. The actuators 21, 22, 23 provide movement in three degrees of freedom, while the constraint assembly 24 constrains movement in three degrees of freedom. In the version shown, the constraint assembly 24 comprises the passive linkage 26, as well as a passive linkage joint 156 that couples the passive linkage 26 to the tool support 18.

In one version, as shown in FIG. 9, the passive linkage joint 156 comprises a passive linkage U-joint. The U-joint comprises a first pivot pin 158 and a joint block 160. The first pivot pin 158 pivotally connects the joint block 160 to a passive linkage mount 162 of the tool support body 80 via a throughbore 164 in the joint block 160. A set screw 166 may secure the first pivot pin 158 to the passive linkage mount 162. The U-joint also comprises a second pivot pin 170. The joint block 160 has a crossbore 168 to receive the second pivot pin 170. The second pivot pin 170 pivotally connects a passive linkage pivot yoke 172 of the passive linkage 26 to the joint block 160. The second pivot pin 170 has a throughbore 171 to receive the first pivot pin 158, such that the first pivot pin 158, the joint block 160, and the second pivot pin 170 form a cross of the U-joint. The first pivot pin 158 and the second pivot pin 170 define pivot axes PA that intersect. As a result, the passive linkage 26 is able to move in two degrees of freedom relative to the tool support body 80. Other types of passive linkage joints are also contemplated, such as a passive linkage spherical joint comprising a ball with slot that receives a pin.

The passive linkage 26 comprises a shaft 174 fixed to the passive linkage pivot yoke 172. The passive linkage 26 also comprises the sleeve 76 of the base 74, which is configured to receive the shaft 174 along a constraint axis CA. The passive linkage 26 is configured to allow the shaft 174 to slide axially along the constraint axis CA relative to the sleeve 76 and to constrain movement of the shaft 174 radially relative to the constraint axis CA during actuation of one or more of the actuators 21, 22, 23.

The passive linkage 26 further comprises a key to constrain rotation of the shaft 174 relative to the sleeve 76 about the constraint axis CA. The key fits in an opposing keyway in the shaft 174 and sleeve 76 to rotationally lock the shaft 174 to the sleeve 76. Other arrangements for preventing relative rotation of the shaft 174 and sleeve 76 are also contemplated, such as an integral key/slot arrangement, or the like. The passive linkage 26 operatively interconnects the tool support 18 and the hand-held portion 16 independently of the actuators 21, 22, 23. The passive linkage is passively adjustable in effective length EL along the constraint axis CA during actuation of one or more of the actuators 21, 22, 23. The sleeve 76, shaft 174, and key 176 represent one combination of links for the passive linkage 26. Other sizes, shapes, and numbers of links, connected in any suitable manner, may be employed for the passive linkage 26.

In the version shown, the passive linkage joint 156 is able to pivot about two pivot axes PA relative to the tool support 18. Other configurations are possible.

Also, in the version shown, the first active joints 92 and the passive linkage joint 156 define pivot axes PA disposed on a common plane. Non-parallel pivot axes PA, parallel pivot axes PA disposed on different planes, combinations thereof, or other configurations, are also contemplated.

In some versions, the head 84 of the tool support 18 is arranged so that the tool 20 is located on a blade plane BP (e.g., blade plane) parallel to the common plane when the tool 20 is coupled to the tool support 18. In some examples, the blade plane BP is spaced from the common plane CP by 2.0 inches or less, 1.0 inches or less, 0.8 inches or less, or 0.5 inches or less.

In the version shown, the actuators 21, 22, 23 are arranged such that the active axes AA1, AA2, AA3 are in a canted configuration relative to the constraint axis CA in all positions of the actuators 21, 22, 23, including when in their home positions. Canting the axes AA1, AA2, AA3 generally tapers the actuator arrangement in a manner that allows for a slimmer and more compact base 74 and associated grip 72. Other configurations are contemplated, including those in which the active axes AA1, AA2, AA3 are not in the canted configuration relative to the constraint axis CA. Such configurations may include those in which the actuator axes AA1, AA2, AA3 are parallel to each other in their home positions.

Further configurations of the actuators, active joints, and constraint assembly are possible. It is contemplated that the control techniques described may be applied to other mechanical configurations not mentioned, in particular those for controlling a tool or saw blade relative to a hand-held portion in one or more degrees of freedom. In some versions, the constraint assembly may be absent and the tool support 18 of the instrument 14 may be able to move in additional degrees of freedom relative to the hand-held portion 16. For example, the instrument may include linear actuators, rotary actuators, or combinations thereof. The instrument may include 2, 3, 4, 5, 6 or more different actuators arranged parallel or in series.

Virtual Boundaries

The software employed by the control system 60 to control operation of the instrument 14 includes a boundary generator 182 (see FIG. 7). The boundary generator 182 may be implemented on the instrument controller 28, the navigation controller 36, or on other components, such as on a separate controller. The boundary generator 182 may also be part of a separate system that operates remotely from the instrument 14. Referring to FIG. 7 the boundary generator 182 is a software program or module that generates one or more virtual boundaries 184 for constraining movement or operation of the instrument 14. In some examples, the boundary generator 182 provides virtual boundaries 184 that define a virtual cutting guide (e.g., a virtual saw cutting guide). Virtual boundaries 184 may also be provided to delineate various control regions as described below. The virtual boundaries 184 may be one-dimensional (1D), two-dimensional (2D), three-dimensional (3D), and may comprise a point, line, axis, trajectory, plane (an infinite plane or plane segment bounded by the anatomy or other boundary), volume or other shapes, including complex geometric shapes. The virtual boundaries 184 may be represented by pixels, point clouds, voxels, triangulated meshes, other 2D or 3D models, combinations thereof, and the like. U.S. Patent Publication No. 2018/0333207 and U.S. Pat. No. 8,898,043 are incorporated by reference, and any of their features may be used to facilitate planning or execution of the surgical procedure.

The virtual boundaries 184 may be used in various ways. For example, the control system 60 may: control certain movements of the tool 20 to stay inside the boundary; control certain movements of the tool 20 to stay outside the boundary; control certain movements of the tool 20 to stay on the boundary (e.g., stay on a point, trajectory, or plane); control certain movements of the tool 20 to approach the boundary (attractive boundary) or to be repelled from the boundary (repulsive boundary); or control certain functions of the instrument 14 based on a relationship of the instrument 14 to the boundary (e.g., spatial, velocity, etc.). Other uses of the virtual boundaries 184 are also contemplated.

In some examples, one of the virtual boundaries 184 is a desired cutting plane, as shown in FIG. 2. The control system 60 will ultimately function to keep the tool 20 on the desired cutting plane in some versions. The virtual boundary 184 that controls positioning of the tool 20 may also be a volumetric boundary, such as one having a thickness slightly larger than a blade thickness to constrain a saw blade to stay within the boundary and on a desired cutting plane, as shown in FIG. 2. Therefore, the desired cutting plane can be defined by a virtual planar boundary, a virtual volumetric boundary, or other forms of virtual boundary. Virtual boundaries 184 may also be referred to as virtual objects. The virtual boundaries 184 may be defined with respect to an anatomical model AM, such as a 3D bone model (see FIG. 2, which illustrates the anatomical model AM being virtually overlaid on the actual femur F due to their registration). In other words, the points, lines, axes, trajectories, planes, volumes, and the like, that are associated with the virtual boundaries 184 may be defined in a coordinate system that is fixed relative to a coordinate system of the anatomical model AM such that tracking of the anatomical model AM (e.g., via tracking the associated anatomy to which it is registered) also enables tracking of the virtual boundary 184.

The anatomical model AM is registered to the first patient tracker 54 such that the virtual boundaries 184 become associated with the anatomical model AM and associated coordinate system. The virtual boundaries 184 may be implant-specific, e.g., defined based on a size, shape, volume, etc. of an implant or patient-specific, e.g., defined based on the patient's anatomy. The virtual boundaries 184 may be boundaries that are created pre-operatively, intra-operatively, or combinations thereof. In other words, the virtual boundaries 184 may be defined before the surgical procedure begins, during the surgical procedure (including during tissue removal), or combinations thereof. The virtual boundaries 184 may be provided in numerous ways, such as by the control system 60 creating them, receiving them from other sources or systems, or the like. The virtual boundaries 184 may be stored in memory for retrieval or updating.

In some cases, such as when preparing the femur F for receiving the total knee implant IM (see FIG. 1), the virtual boundaries 184 comprise multiple planar boundaries that can be used to delineate multiple cutting planes (e.g., five cutting planes) for the total knee implant IM, and are associated with a 3D model of the distal end of the femur F.

These multiple virtual boundaries 184 can be activated, one at a time, by the control system 60 to constrain cutting to one plane at a time.

The instrument controller 28 or the navigation controller 36 track the state of the tool 20 relative to the virtual boundaries 184. In one example, the state of the TCP coordinate system (e.g., pose of the saw blade) is measured relative to the virtual boundaries 184 for purposes of determining target positions for the actuators 21, 22, 23 so that the tool 20 remains in a desired state. In some cases, the control system 60 controls the instrument 14 in a manner that emulates the way a physical handpiece would respond in the presence of physical boundaries.

Referring back to FIG. 7, two additional software programs or modules run on the instrument controller 28 or the navigation controller 36. One software module performs behavior control 186. Behavior control 186 is the process of computing data that indicates the next commanded position or orientation (e.g., desired pose) for the tool 20. In some cases, only the desired position of the TCP is output from the behavior control 186, while in some cases, the commanded pose of the tool 20 is output. Output from the boundary generator 182 (e.g., a current position or orientation of the virtual boundaries 184 in one or more of the coordinate systems) may feed as inputs into the behavior control 186 to determine the next commanded position of the actuators 21, 22, 23 or orientation for the tool 20. The behavior control 186 may process this input, along with one or more other inputs described further below, to determine the commanded pose.

The instrument controller 28 may control the one or more actuators 21, 22, 23 by sending command signals to each actuator 21, 22, 23 to adjust the tool 20 towards a desired pose. The instrument controller 28 may know the entire length that an actuator 21, 22, 23 may adjust the tool support 18 relative to the hand-held portion 16. In some examples, the instrument controller 28 knows the entire length which an actuator 21, 22, 23 is capable of adjusting and may send command signals to the actuators 21, 22, 23 to move a measured distance from position to position. A measured position may be a known position, or a distance between the present location of an actuator 21, 22, 23 and the actuator limits. Each position that the actuator 21, 22, 23 moves to may be a measured distance from a positive limit and a negative limit of actuator travel (i.e. a position between two ends of a lead screw). The instrument controller 28 may command the actuators 21, 22, 23 to and from measured positions as described below.

The instrument controller 28 may send command signals to each actuator 21, 22, 23 to move the actuators 21, 22, 23 from a first position to a commanded position which will place the tool 20 into a desired pose. In some examples, the commanded position may be determined by the instrument controller 28 in conjunction with the navigation system 32 to determine the location of the tool 20 and tool support 18 relative to the hand-held portion 16, patient trackers PT, 54, 56, a virtual object, such as desired cut plane or a combination thereof and send a signal to the actuators 21, 22, 23 to adjust a certain distance or commanded position in order to place the tool 20 into the desired pose. The instrument controller may command the actuator 21, 22, 23 to a position in order to reach the desired adjustment of the tool 20. The instrument controller 28 may control the actuators 21, 22, 23 to linearly move a calculated distance to adjust the tool 20 towards a desired pose. In other examples, such as when absolute encoders are used, the instrument controller may send signals to the actuators 21, 22, 23 to place each actuator

21, 22, 23 into a commanded position based on the known location of the tool support 18 relative to the hand-held portion determined by the absolute encoder.

The instrument controller 28 may know the entire length that an actuator 21, 22, 23 may adjust the tool support 18 relative to the hand-held portion 16. In some examples, the instrument controller 28 knows the entire length which an actuator 21, 22, 23 is capable of adjusting and may send command signals to the actuators 21, 22, 23 to move a measured distance from position to position (e.g., by commanding a desired amount of linear travel via commanded rotation). A measured position may be a known position, or a distance between the present location of an actuator 21, 22, 23 and the actuator limits. Each position that the actuator 21, 22, 23 moves to may be a measured distance from a positive limit and a negative limit of actuator travel (i.e., a position between two ends of a lead screw). The instrument controller 28 may command the actuators 21, 22, 23 to and from positions as described below. The instrument controller may command the actuator 21, 22, 23 to a position in order to reach the desired adjustment of the tool 20. The instrument controller 28 may control the actuators 21, 22, 23 to linearly move a calculated distance to adjust the tool 20 towards a desired pose. In other examples, such as when absolute encoders are used, the instrument controller may send signals to the actuators 21, 22, 23 to place each actuator 21, 22, 23 into a commanded position based on the known location of the actuator 21, 22, 23 between the respective actuator travel limits determined by the absolute encoder. Alternately, in one example, an incremental encoder may be used in conjunction with a homing procedure performed during system setup as described in U.S. Patent Publication No. 2017/0156799, which is hereby incorporated by reference. A homing procedure may be used, placing the actuators 21, 22, 23 and the joints at their centered position, and subsequently determines the absolute offsets of the incremental encoders. By determining the offsets of the incremental encoders, the incremental encoders may perform as absolute encoders going forward.

In some examples, when a homing position is used, the homing process establishes the initial rotor positions (zero position) of the actuators 21, 22, 23. The home position is effectively a position of the rotor 148 that provides the greatest possible travel in each direction along the active axis AA1, AA2, AA3. In some examples, the home position is generally located such that a home point HP of the lead screw 150, centrally disposed halfway between the stops 152, is centrally disposed in the associated carrier 116. Even when the homing procedure is not used, such as with absolute encoders, setting the actuators 21, 22, 23 to the home point HP prior to or after executing other modes (such as approach mode, described further below) may be included. The instrument controller 28 may be configured to control the actuators 21, 22, 23 to their home positions between minimum and maximum values of the effective lengths EL of the actuators 21, 22, 23.

When in the home position, the amount of adjustability of the actuators 21, 22, 23 is maximized to keep the tool 20 at a desired pose. Various levels of adjustment are possible depending on the particular geometry and configuration of the instrument 14. In some examples, when all the actuators 21, 22, 23 are in their home positions, the tool 20 may be adjusted in pitch orientation about +/−18° relative to the home position, assuming zero changes in the roll orientation and no z-axis translation. In some examples, when all the actuators 21, 22, 23 are in their home positions, the tool 20 may be adjusted in roll orientation about +/−33° relative to the home position, assuming zero changes in the pitch orientation and no z-axis translation. In some examples, when all the actuators 21, 22, 23 are in their home positions, the tool 20 may be adjusted in z-axis translation about +/−0.37 inches relative to the home position, assuming zero changes in the pitch orientation and roll orientation. The tool 20, of course, may be adjusted in pitch, roll, and z-axis translation simultaneously, sequentially, or combinations thereof during operation. In certain instances, the home position also refer to the tool support being in the home position. When the tool support is in the home position, each of the actuators in the actuator assembly are also in their home position—the adjustability of each of the actuators being maximized to provide for the greatest movement in all degrees of freedom.

In some examples, when one or more of the actuators 21, 22, 23 have reached their mechanical or software-imposed limit, the instrument controller 28 may require the hand-held portion 16 to be adjusted in order to bring the tool 20 back into a range where the actuators are capable of adjusting the tool 20 towards the desired pose. In such a case, a simulated commanded position may be used to indicate to a user how to move the hand-held portion 16 in order to bring the tool 20 and actuators 21, 22, 23 back into alignment with the desired pose. A simulated commanded position may be a position determined by the instrument controller 28 in conjunction with navigation data from the navigation system 32 in which the hand-held portion 16 must be moved to adjust the tool 20 towards a desired pose without adjusting the actuators 21, 22, 23. The simulated commanded position works with the one or more displays 38 to signal to a user that the hand-held portion 16 needs to be moved in particular way to place the tool 20 at the desired pose. The visual indicators described herein may be used to signal to a user to move the hand-held portion 16 in the same fashion as if the actuators 21, 22, 23 were adjusting the tool 20, but relies on the user to correct the pose of the tool 20 by manipulating the hand-held portion 16 while the actuators remain in position.

The second software module performs motion control 188. One aspect of motion control 188 is the control of the instrument 14. The motion control 188 receives data defining the next commanded pose from the behavior control 186. Based on these data, the motion control 188 determines the next rotor position of the rotors 148 of each actuator 21, 22, 23 (e.g., via inverse kinematics) so that the instrument 14 is able to position the tool 20 as commanded by the behavior controller 186, e.g., at the commanded pose. In other words, the motion control 188 processes the commanded pose, which may be defined in Cartesian space, into actuator positions (such as rotor positions) of the instrument 14, so that the instrument controller 28 can command the motors 142 accordingly, to move the actuators 21, 22, 23 of the instrument 14 to commanded positions, such as commanded rotor positions corresponding to the commanded pose of the tool 20. In one version, the motion control 188 regulates the rotor position of each motor 142 and continually adjusts the torque that each motor 142 outputs to, as closely as possible, ensure that the motor 142 drives the associated actuator 21, 22, 23 to the commanded rotor position. This generated commanded pose, which is defined in Cartesian space, may also be used to control the visual indicators as described below.

In some versions, the instrument controller 28, for each actuator 21, 22, 23, determines the difference between a measured position and a commanded position of the rotor 148. The instrument controller 28 outputs a target current (proportional to a torque of the rotor), changing the voltage to adjust the current at the actuator from an initial current to the target current. The target current effectuates a movement of the actuators 21, 22, 23, moving the tool 20 from the measured pose to the commanded pose. This may occur after the commanded pose is converted to joint positions. In one example, the measured position of each rotor 148 may be derived from the sensor S described above, such as an encoder.

The boundary generator 182, behavior control 186, and motion control 188 may be sub-sets of a software program. Alternatively, each may be software programs that operate separately or independently in any combination thereof. The term "software program" is used herein to describe the computer-executable instructions that are configured to carry out the various capabilities of the technical solutions described. For simplicity, the term "software program" is intended to encompass, at least, any one or more of the boundary generator 182, behavior control 186, or motion control 188. The software program can be implemented on the instrument controller 28, navigation controller 36, or any combination thereof, or may be implemented in any suitable manner by the control system 60.

A clinical application 190 may be provided to handle user interaction. The clinical application 190 handles many aspects of user interaction and coordinates the surgical workflow, including pre-operative planning, implant placement, registration, bone preparation visualization, and post-operative evaluation of implant fit, etc. The clinical application 190 is configured to output to the displays 38. The clinical application 190 may run on its own separate processor or may run alongside the instrument controller 28 or the navigation controller 36. In one example, the clinical application 190 interfaces with the boundary generator 182 after implant placement is set by the user, and then sends the virtual boundaries 184 returned by the boundary generator 182 to the instrument controller 28 for execution.

An initial location of the base coordinate system BCS can be determined based on a known geometric relationship between the tool support coordinate system TCS and the base coordinate system BCS when the actuators 21, 22, 23 are in their home positions or other predetermined position. This relationship changes when the actuators 21, 22, 23 are adjusted and the associated changes can be determined based on the kinematics of the robotic system 10 (e.g., which establishes a dynamic transformation between these coordinate systems). Alternatively, or additionally, another tracker could be attached and fixed with respect to the base coordinate system BCS to directly track a pose of the base coordinate system BCS relative to the tool support coordinate system TCS. Thus, the robotic system 10 knows the position of the tool 20, such as in the home position and its relation to the pose of the hand-held portion 16. Accordingly, when the tool 20 is moved by the user and its pose is tracked using the tool tracker 52, the robotic system 10 also tracks the pose of the hand-held portion 16 and its base coordinate system BCS. In some examples, as a result of prior calibration processes, the position of the tool 20 relative to the tool support 18 is assumed to be known.

In some versions, the home position is determined by first determining a pose of the hand-held portion 16 (e.g., of the base coordinate system BCS) relative to the tool support 18 (e.g., relative to the tool support coordinate system TCS) in a common coordinate system by employing a separate tracker fixed to the hand-held portion 16. This spatial relationship between the hand-held portion 16 and the tool support 18 could also be determined by registration using the pointer 57 and known calibration divots on the hand-held portion 16, or via other navigation methods. The current rotor position of each of the actuators 21, 22, 23 can then be derived from this spatial relationship based on the kinematics of the instrument 14. Knowing the current rotor positions and measuring changes from the current rotor positions using the encoders (and corresponding encoder signals), the instrument controller 28 can thereafter operate each of the actuators 21, 22, 23 until they reach their home positions. The home positions can be stored in the memory of the instrument controller 28.

In essence, the instrument controller 28 uses tracking data obtained by the navigation system 32 from the tracker 52 coupled to tool support 18 and the hand-held portion 16 on the instrument 14 to determine the position of the actuators 21, 22, 23 so that, thereafter, the incremental encoders can operate as absolute encoders.

Instructional data packets are sent, for example, to the motor controllers, such as from the console 33 or another component of the instrument controller 28. These instructional data packets include the target position for the rotors 148 of the motors 142 (or target position of the actuator). Here, each target position may be a positive or negative number representative of a targeted cumulative count for the associated rotor 148. The console 33 or other component of the instrument controller 28 generates and sends these instructional data packets to each motor controller at the rate of one packet every 0.05 to 4 milliseconds. In some examples, each motor controller receives an instructional data packet at least once every 0.125 milliseconds.

During use, when the robotic system 10 determines a pose (a current pose) of the tool 20 with the navigation system 32 by virtue of the tool tracker 52 being located on the tool support 18. The instrument controller 28 may also determine a current position of each of the actuators 21, 22, 23 based on an output encoder signal from the one or more encoders located on each of the actuators 21, 22, 23. Once the current position of each of the actuators 21, 22, 23 is received, the instrument controller 28 may calculate a current pose of the hand-held portion 16 (e.g., a current pose of the base coordinate system BCS with respect to a desired coordinate system, such as the TCP coordinate system using forward kinematics to convert from the actuator positions to the pose (TCP with respect to BCS)). Once the instrument controller 28 has the current relative poses of the tool support 18 and the hand-held portion 16 in the desired coordinate system, the instrument controller 28 may then determine a commanded pose of the tool 20 based on the current pose of the tool 20 as determined by the navigation system 32, the current pose of the hand-held portion 16 calculated by the current position of each of the actuators 21, 22, 23, and based on a position or orientation of a planned virtual object, subject as a desired cutting plane. The instrument computes a pose (a commanded pose) of TCP with respect to BCS that results in the TCP being on the desired plane or aligned with the planned virtual object. The instrument controller 28 may send command instructions to the actuators 21, 22, 23 to move to a commanded position, thereby changing the pose of the tool support 18 and tool 20. In one example, the commanded pose of the tool 20 is further based on a target cut plane so the instrument controller 28 calculates the current pose of the tool support 18 and the current positions of the actuators 21, 22, 23 in order to determine the current pose of the hand-held portion 16. Once the current pose of the tool support 18, current positions of the actuators 21, 22, 23, and the current pose of the hand-held portion 16 are known, the instrument controller 28 can send command signals to the actuators 21, 22, 23 to adjust the tool support 18 and tool 20 based on the desired plane. The controller computes the commanded pose assuming that, momentarily (during a single iteration) the pose of the hand-held portion (BCS) is stationary relative to patient anatomy. By updating the corresponding poses each time, the actual movement of BCS is adjusted for.

Figure 10:
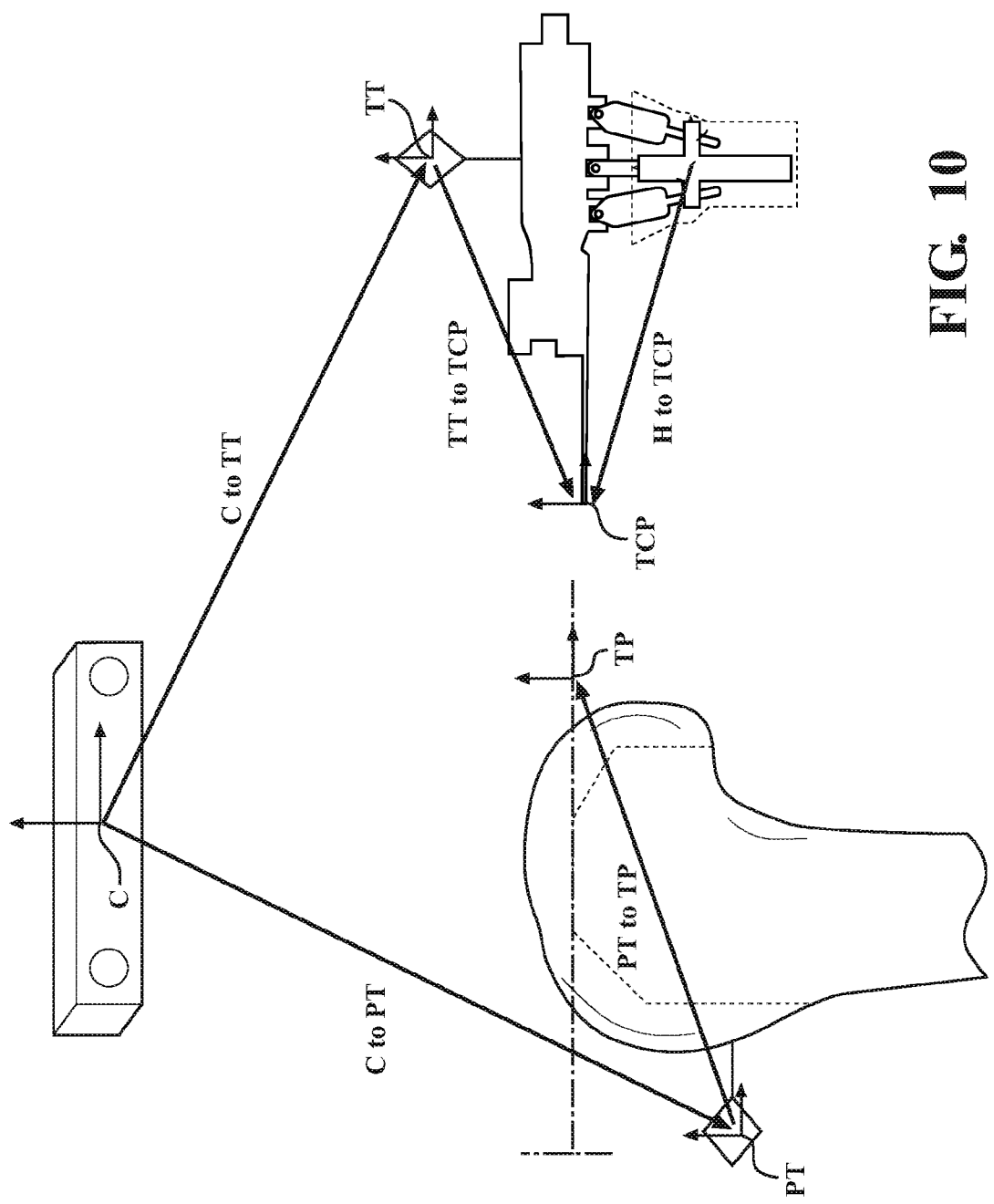
FIG. 10 is a schematic view of various transforms of the hand-held robotic surgical system.

Turning to FIG. 10, the exemplary control is described with respect to the various transforms. The TCP is determined by tracking the tool 20 with the tool tracker 52 in C (C-TT) and determining a transform between tool tracker 52 and the TCP of the tool 20 (TT-TCP), such as the saw, using registration data. Similarly, the patient is tracked using the patient tracker PT (shown as 54) in the C(LCLZ-PT). A transform (PT-TP) is determined between the patient tracker PT and each planned virtual object (TP) using registration data and planning information. As described above, a transform between BCS and TCP (BCS-TCP) is computed based on the current positions of each actuator (described above). The transform between BCS and TCP is utilized to relate the various coordinate systems back to the hand-held portion 16, since the commanded pose may be determined relative to the BCS. Conceptually, the commanded pose, is an update to the BCS to TCP transform which results in the TCP being aligned with the planned virtual object (the target plane TP), which may include one or more virtual boundaries 184, in this example.

It should be appreciated that the phrase 'TCP' of the instrument" has been used interchangeably with the phrase 'position of the saw blade'. Thus, in any instance where the TCP of the instrument/tool is used, it may be substituted with the position of the saw blade and vice-versa. Of course, it is also contemplated that the position of the 'saw blade' may alternatively be a position of a tool of any suitable configuration, such as a drill, bur, guide tube, pin, and the like.

Throughout this description, unless otherwise noted, any instance of pose may be a commanded pose, a current pose, a past pose, or a past commanded pose. While each of these poses may be different from one another, due to the frequency of control, the difference in position or orientation between these poses may be minimal in each control iteration.

It should be understood that the combination of position and orientation of an object is referred to as the pose of the object. Throughout this disclosure, it is contemplated that the term pose may be replaced by position or orientation and vice-versa to achieve suitable alternatives of the concepts described herein. In other words, any use of the term pose can be replaced with position and any use of the term position may be replaced with pose.

Operation

During operation, the robotic system 10 is initially powered up and the software application for operating the system is started. The trackers 52, 54, 56, PT are initialized and the trackers 52, 54, 56 are placed on the instrument 14 and on the target anatomy (e.g., femur F and tibia T). With the patient trackers 54, 56 mounted to the anatomy, the anatomy or associated images/models are registered to the patient trackers 54, 56 using known registration techniques. This may require the user to touch certain surfaces or landmarks on the anatomy with the pointer 57. For example, this may require the user to touch several points on the surface of the anatomy while pressing a select button on the pointer 57 or pressing a foot switch of the navigation system 32. This "paints" the points on the surface in the navigation system 32 for matching with the pre-operative or intra-operative image/model of the anatomy. The pre-operative image or the intra-operative image/model of the anatomy is loaded in the navigation system 32. The tracked portion of the anatomy is registered to the pre-operative or intra-operative image/model. By extension, this allows the robotic system 10 to, as the anatomy moves, present a graphical representation of the actual position and orientation of the anatomy on the displays 38.

In a calibration procedure, the orientation and location of the tool tracker 52 is calibrated relative to the tool support 18 by reference to the fixed and known locations of the calibration divots CD or other reference points. In some examples, one or more tool trackers 52 may be located on the tool support 18, the hand-held portion 16, or both so that the position of the tool support 18 or the hand-held portion 16 are tracked by the navigation system 32. In examples in which the tool tracker 52 is integrated into the instrument 14, then such calibration would be unnecessary since the relative location of the tool tracker 52 to the tool support 18 is known.

The virtual objects (e.g., virtual boundaries 184) being used to control operation of the instrument 14 are also defined. Software running on instrument controller 28 (e.g., the boundary generator 182) generates an initial definition of the virtual objects. The user may have the ability and option to adjust the placement of the virtual objects as may be necessary.

In one exemplary configuration, the control system 60 defines various regions at predefined distances or positions from the target site or anatomy. Each of these regions may be defined in the coordinate system associated with the anatomy or virtual boundaries 184. In some cases, these regions are defined as spheres or other geometric primitives about the target site or the anatomy. In other examples, the regions (and others described below) may be defined with respect to the instrument 14, tool support 18, the hand-held portion 16, the tool 20, the target, or a combination thereof. The control system 60 may control the instrument 14 when the regions defined by the hand-held portion 16, the tool support 18, the tool 20, the target, or a combination thereof approach a specific virtual boundary.

In particular, the instrument controller 28 generates a set of target rotor positions to which the rotors 148 integral to the motors 142 must rotate to maintain the tool 20 at the desired pose. In other words, if the user moves the hand-held portion 16 in a manner that causes the tool 20 to move away from its desired pose, this is detected by the navigation system 32. In response to this movement, the instrument controller 28 determines, based on data from the navigation system 32, how far the tool 20 has moved away from the desired pose and compensates for such movement by driving the actuators 21, 22, 23 as needed to bring the tool 20 back to the desired pose. It should be appreciated that such deviations from the desired pose will usually be small, as the instrument controller 28 will be operating at a high frequency (e.g., frame rate) to continuously account for such deviations in substantially real-time.

The target rotor positions are determined based on the relationships between actuation of the actuators 21, 22, 23 and resulting movement (e.g., kinematics). For example, if the desired pose requires z-axis translation relative to the hand-held portion 16, there is a first order relationship between the extent to which the tool 20 will move in the z-axis and the amount of rotation of each rotor 148 (e.g., how many counts are associated with such z-axis movement). There are also relationships between the extent to which the tool 20 will change its pitch orientation in response to actuation of the third actuator 23 alone, or in combination with one or both of the first and second actuators 21, 22. Lastly, there are relationships between the extent to which the tool 20 will change its roll orientation in response to actuation of one or both of the first and second actuators 21, 22, with or without actuation of the third actuator 23. Based on these relationships, the instrument controller 28 determines the target rotor position for each rotor 148 that is required to maintain the desired pose of the tool 20. The instrument controller 28 operates the motors 142 based on these target rotor positions. For example, the console 33 may transmit packets to the motor controllers containing these target rotor positions, and each motor controller may apply appropriate energization signals to the associated motor 142. These energization signals cause the rotation of the rotor 148 that results in the repositioning of the lead screw 150 that displaces the tool support 18/tool 20 as needed to maintain the tool 20 in the desired pose.

As described previously, the actuators 21, 22, 23 are held at the home position or other predetermined position as the user arranges the hand-held portion 16 toward the desired plane. By keeping the actuators 21, 22, 23 at their home position or other predetermined position, a user may find it easier to adjust and line up the tool 20 with the desired plane and instrument pose relative to the target. However, when the tool is at the desired pose, the visual indicator is intended to guide the user as to how to move the hand-held portion 16 to provide the instrument 14 with sufficient adjustability by keeping the actuators 21, 22, 23 near their home positions or other predetermined position. For example, the user may need to move the hand-held portion 16 upwardly in the z-axis direction to move all the actuators 21, 22, 23 closer to their home positions, while keeping the tool 20 at the desired pose. In other words, the actuators 21, 22, 23 may be nearly fully extended. To accomplish this, the directional indication from the visual indicator is upward. In this case, the visual indicator is actually guiding the user to move the hand-held portion 16 upward so that the actuators 21, 22, 23 operate toward their home positions to maximize adjustability of the actuators 21, 22, 23. As the user moves the hand-held portion 16 upward, the actuators 21, 22, 23 continue to operate to keep the tool 20 at the desired pose (e.g., on the virtual boundary 184). As a result, the actuators 21, 22, 23 retract, such as retracting toward their home positions. Ideally, when the user starts cutting bone, a maximum amount of travel is available in either direction for each actuator 21, 22, 23. Otherwise, if one or more of the actuators 21, 22, 23 have nearly reached their available travel in either direction, then even slight movements of the hand-held portion 16 may result in the instrument controller 28 being unable to keep the tool 20 at the desired pose, and an inaccurate cut could be made.

Additionally or alternatively, in some versions, the tool 20 may move to the desired pose and then the user may adjust the hand-held portion 16 to a more comfortable position within the threshold value of available travel of actuators 21, 22, 23 to perform a cut while the tool 20 is maintained at its desired position. The user may then select, by activating an input device, such as a button or a foot switch, or selecting on a touchscreen, to move into a free-hand mode where the pose of the hand-held portion 16 relative to the pose of the tool 20 is held or frozen in its current spatial relationship. It is contemplated that the held pose of the hand-held portion 16 relative to the pose of the tool 20 changes the virtual threshold value of the actuators 21, 22, 23, restraining actuator movement by to maintain the held pose once the user has selected an operating mode.

Visual Guidance

As shown in FIG. 8, the robotic system 10 also includes visual indicator 201. Other exemplary visual indicators are shown in FIGS. 21-24, 26-42C. The visual indicator may be configured differently depending on user preference. In one configuration and with reference to FIG. 8, the visual indicator may be coupled to the instrument. More particularly, the visual indicator may be coupled to the tool support, the hand-held portion, or a combination thereof. Alternatively, with reference to FIG. 1, the visual indicator may be positioned separately from the instrument, such as on the UI. For example, the visual indicator may take the form of a display screen positioned in the operating room for ease of view by the surgeon. More particularly, the visual indicator may be in the form of a display screen coupled to a navigation cart. Depending on the location of the visual indicator relative to the controller(s) of the system, the visual indicator may be coupled to a transmitter unit. The transmitter unit can include a processing portion and a power supply. As should be appreciated, any of the above components may be distributed across one or more separate devices or locations. The transmitter unit may be electrically coupled to the visual indicator, so as to establish a wired or wireless electrical connection between the transmitter unit and the display visual indicator.

The use of the visual indicator may provide additional robustness in design by avoiding poses that could lead to interruption of the surgical procedure, such as avoiding poses where the limits of the range of motion in one or more degrees of freedom have been met. This is due to the fact that the control system may be configured to determine whether an override to the drive motor is necessary As the control system 60 determines the commanded position or commanded joint angle for each actuator to move the TCP to the target pose, the control system 60 may control activation of the drive motor M based on one or more positions of the plurality of actuators or the tool support. The one or more actuator positions may be based on the commanded joint position of at least one actuator, a measured position of at least one actuator, a previous commanded position of at least one actuator, a previous measured position of at least one actuator, or combinations thereof. In one example, the drive motor M is controlled based on a commanded position of at least one of the actuators 21, 22, 23. The commanded joint position of the at least one actuator 21, 22, 23 is compared with an actuator motor override limit of the at least one actuator 21, 22, 23. The motor override limit may be a value, or a series of values defining the outer bounds of a range. Although this example demonstrates monitoring one actuator, the control system may monitor the commanded position and the actuator motor override limits of each actuator 21, 22, 23. The upper limit and the lower of the actuator motor override limit may be values corresponding to the position of the actuator relative to the operational range of each actuator. The upper limit may correspond to a maximum allowed traveled in a first direction, and the lower limit may correspond to a maximum allowed travel in a second, opposite direction before the drive motor parameter will be adjusted. More specifically, the control system 60 controls a motor parameter of the drive motor M at a first value and a second value based on whether the commanded joint position would keep the actuator position between the upper limit and lower limit of the motor override limits. The control system 60 may control one or more motor parameters of the drive motor M, the one or more motor parameters may be a speed, a torque, an operation time, a current, or a combination thereof. In one example, the motor parameter controlled by the control system 60 is the motor speed, the first value being zero (drive motor M is off) and the second value being greater than zero (drive motor M is on). The control system 60 switches the motor parameter between the first and second values based on the commanded position of the actuator 21, 22, 23. When the commanded position of the actuator 21, 22, 23 places the actuator within the upper limit and lower limit of the motor override limits, the control system 60 may command the second value of the drive motor parameter, allowing the drive motor M to be actuated or continue to be energized. When the commanded actuator position is between the lower and upper motor override limits, a joint velocity command override is not modified In some examples, the drive motor override may be implemented as a lookup table or function that is evaluated based on the actuator position (P) data received. For the example of the joint position velocity override, this would allow the speed of the drive motor to get ramped down proportionally as the joint position approaches its motor override limit. In some examples, there may be no modification when the actuator position is within the lower and upper motor override limits. In other examples, proportional ramp down of drive motor M speed when one or more of the actuators 21, 22, 23 are at a position between 80% travel to 95% travel range, and may be fully disabled above 95% travel, which may provide a continual and gradual feedback to the user that the tool 20 is approaching the operational limits (the lower and upper motor override thresholds). In such an implementation, there may be a plurality of lower motor override thresholds and a plurality of upper motor override threshold, each threshold corresponding to a motor parameter (such as a motor speed) In some cases, the drive motor M speed may not be reduced to zero completely, but rather to a fixed lower speed, allowing the surgeon to be alerted but allowing a determination as to whether to proceed at the surgeon's discretion. When the commanded position of the actuator 21, 22, 23 places the actuator outside of the upper limit and lower limit of the motor override limit, the control system 60 may command the first value of the drive motor parameter, preventing the drive motor M from being actuated or continuing to be energized. The motor override limits for each actuator may be different than the joint thresholds for each actuator described above. For example, the motor override limits may define a narrower range than a range defined the joint thresholds, and the range of the motor override limits may be wholly within the joint threshold range. By utilizing the visual indicator, a user can more easily avoid the upper and lower limits of the motor override limits attributed to each actuator, and minimize interruptions caused by shutting off of the drive motor.

Different control methodologies may be used to control the plurality of actuators to place the tool at a desired location, such as target plane, including but not limited to impedance control, admittance control, position control, or a hybrid control using multiple different control implementations. While an admittance control implementation is described in detail, it should be appreciated that other methodologies may be used. In an admittance control mode, the control system accepts force input (virtual or measured) and commands position (or motion) output. For example, for admittance control, the system models a force or torque at a particular location on a virtual mass and acts to modify the pose of the virtual mass to achieve the desired target state of the tool. In an impedance control mode, the control system accepts position (or motion) input and commands a force or torque output. For example, the impedance control system measures, senses, or calculates a position (i.e., position, orientation, velocity, or acceleration) of the instrument and may apply an appropriate corresponding torque to each of the actuators to achieve the desired target state of the tool. Position control may also be used to control the plurality of actuators towards implementing certain behaviors. It should be appreciated that changes to both the behavior controller and the motion controller would be needed implement these control schemes.

The control system may be configured to determine a pose of the of the hand-held portion in a known coordinate system. The pose of the hand-held portion may be a commanded pose, a simulated commanded pose, a measured pose, a previous commanded pose, a previous measured pose, or combinations thereof. In one particular implementation, the pose of the hand-held portion is a commanded pose, and the commanded pose of the hand-held portion is a relationship between the saw blade and the hand-held portion. Alternatively, the control system may be configured to determine a pose of the tool support in the known coordinate system in a similar way. In the examples described below, the commanded pose is computed for the hand-held portion relative to the target plane (TP). Additional detail on the transforms that are utilized to compute the commanded pose is described with reference to FIG. 10, and in U.S. Provisional Application No. 63/085,651, filed on Sep. 30, 2020, which is hereby incorporated by reference in its entirety. It should be appreciated that the visual indicator may be controlled based on other poses, including poses computed relative to different components of the system.

Based on the computed pose of the hand-held portion relative to the target plane, the control system may determine a pitch value, a roll value, an elevation value or combinations thereof. In other words, the control system may determine a position or orientation of the hand-held portion in one or more degrees of freedom, such as the position in translation (such as z-axis translation, referred to herein as elevation), the orientation in roll, and the orientation in pitch that constitute the commanded pose. Additionally or alternatively, depending on the nature of the actuator assembly, the positions and orientations of the hand-held portion may be computed in other degrees of freedom, such as yaw, x-axis and y-axis translation. These values may be expressed in Cartesian space of the hand-held portion. It should be appreciated that description below is an example of where the visual indicator is controlled based on the positions or orientations of the hand-held portion and the range of motion of the hand-held portion. However, it is also contemplated that similar computations could be made with respect to other portions of the instrument, such as the tool support or the tool. For this reason, throughout the disclosure, any reference to controlling the visual indicator based on a characteristic (such as pose or position or orientation or range of motion) of the hand-held portion can be replaced with controlling the visual indicator based on a characteristic of other parts of the instrument, such as controlling the visual indicator based on the pose/position/orientation or range of motion of the tool support or the tool. Examples for these implementations have been omitted for brevity.

The control system may also be configured to determine or receive a theoretical range of motion of the hand-held portion relative to the tool support. In certain instances, the theoretical range of motion of the hand-held portion may be based on the particular pose of the hand-held portion. This is due to the fact that the range of motion in one or more degrees of freedom may vary based on the position or orientation of the hand-held portion in another degree of freedom. For example, the range of motion in the roll degree of freedom and the pitch degree of freedom may vary based on the position of the hand-held portion in the elevation degree of freedom. In other words, the range of motion in roll may be less at a first elevation value than at a second elevation value. The theoretical range of motion data set may be obtained empirically or mathematically. One such empirical method may be to plot the actual poses of the hand-held portion in a statistically significant number of poses representing a variety of relationships between the tool support and the hand-held portion. Various curve-fitting algorithms and regressions may be used to plot and calculate the theoretical range of motion based on the empirically collected data set. Alternatively, the theoretical range of motion may be computed mathematically based on the kinematics of the actuator assembly.

In one example, the control system may compute the range of motion for each of a plurality of degrees of freedom independently. For example, the control system compute a range of motion in pitch, a range of motion in roll, and a range of motion in elevation. Referring to FIG. 12, the range of motion of the hand-held portion may be a volume defined by Cartesian model 200 in the known coordinate system. The Cartesian model 200 represents a three-dimensional workspace of the hand-held portion relative to the tool support or vice-versa. The Cartesian model is computed in the same coordinate system as the pose used to determine the pitch, roll, translation, etc. of the hand-held portion. The Cartesian model is 200 used to understand the theoretical range of motion. The Cartesian model is mapped to the Cartesian coordinates that are used to express the pose of the tool support in terms of the pitch value, the roll value, or elevation value, i.e., a first degree of freedom, a second degree of freedom, or a third degree of freedom. The Cartesian model 200 is defined by x, y, and z coordinates and hence, can be mapped to roll values, pitch values, and elevation values. As described above, the Cartesian model 200 representing the three-dimensional workspace of the tool support may be derived from empirical data. While a diamond shape is shown for the Cartesian model 200, it should be understood that the Cartesian model can have suitable three dimensional shape, and is not necessarily symmetrical. Furthermore, it should be understood that the Cartesian model may be represented with a plurality of intersecting lines, the equations for each of those intersecting lines can be calculated based on various regressions from the empirical data or based on the kinematics of the actuator assembly.

The shapes of the predetermined Cartesian model may be implemented as a volume, such as an octahedron, an asymmetrical octahedron, a sphere, a cuboid, a cylinder, etc. Particularly, in some examples, the Cartesian model when defined as a volume, may be asymmetrical in shape, such as asymmetrical about a plane position between the tool support 18 and the hand-held portion 16 when each of the actuators are in the home position, with the Cartesian volume being greater above the plane than below the plane. In this example, the volume may be defined by a plurality of Cartesian points. This volume may be less than the dexterous workspace (less than all reachable configurations). Alternatively, the predetermined Cartesian model may be defined in each degree of freedom separately. For example, the Cartesian model may be defined with a plurality of Cartesian points. The predetermined Cartesian space may also be defined by one or more orientations, based on any one, two or three of the axes along which or about which the saw blade can be displaced (x, y, and z).

In essence, the relationship between the Cartesian model 200 used to express the pose of the hand-held portion and the Cartesian coordinate system used to understand the theoretical range of motion is known. To simplify the calculation it will be assumed that the origins of the two Cartesian coordinate systems are aligned with one another or known relative to one another, and may be referred to interchangeably throughout this disclosure. Because the range of motion of certain degrees of freedom may not be critical depending on the actuator configuration, the position or orientation in every degree of freedom need not be compared to the theoretical range of motion.

The Cartesian model 200 may be understood to include a plurality of two-dimensional slices, each slice representing the range of motion in two degrees of freedom based on a position or orientation in a third degree of freedom. In FIG. 12, each two-dimensional slice (202', 202") represents a range of motion in the pitch degree of freedom and the roll degree of freedom at a particular elevation value. With reference to FIG. 12, is readily apparent that the lower elevation slice corresponds to additional range of motion in pitch and roll than the upper elevation slice. As described above with respect to the Cartesian model as a whole, each two-dimensional slice may be represented by a plurality of lines, such as four lines. Each line having an equation defined. The area enclosed by the intersections of those lines can be understood as the two-dimensional slice region.

Referring now to FIGS. 13-20, with respect to the theoretical range of motion of the hand-held portion, the plurality of two-dimensional slices 202'''-202" " can be understood as a plurality of two-dimensional regions, with each region defining its own origin at the particular elevation. Thus, each of the two-dimensional slices can be understood in a polar coordinate system. The outer bounds of the two-dimensional regions corresponding to pitch and roll values (x1, y1; x2, y2; x*, y* . . . ) at the outermost limits of the range of motion of the hand-held portion at that particular elevation. The number of two-dimensional slices is not particularly limited (only two are shown in FIG. 12), and may be plotted at a discrete elevation interval, such as 0.1 mm. In other words, a two-dimensional region may be computed from the minimum to the maximum possible elevation value, at intervals of 0.1 mm, for the entire Cartesian model. Of course, any suitable interval may be used. The control system may select the two-dimensional region that most closely corresponds to the elevation value of that commanded pose.

Generally speaking, the control system is configured to control the visual indicator based on the actual position or orientation of the hand-held portion in one or more degrees of freedom and the range of motion in one or degrees of freedom. This may include controlling the visual indicator based on a position or orientation of the hand-held portion and the range of motion in a first degree of freedom, based on a position or orientation of the hand-held portion and the range of motion in a second degree of freedom, and based on a position or orientation of the hand-held portion and the range of motion in a third degree of freedom. As mentioned, the visual indicator could also be controlled based on the positions and orientations in other degrees of freedom.

Furthermore, it should be understood that the control system may be configured determine a first pose of the hand-held portion and a first range of motion based on the first pose and determine a second pose of the hand-held portion, and determine a second range of motion based on the second pose. It should be understood that the first range of motion and the second range of motion are different and that the first and second poses are different from one another, i.e., represent the poses of the hand-held portion at two different instances of time. Because the range of motion in one or more degrees of freedom may be dependent on the position or orientation of the hand-held portion in another degree of freedom, the range of motion may be different in the first range of motion and the second range of motion. The control system may determine the position or orientation of the hand-held portion based on the first pose in the first degree of freedom and control the visual indicator based on the first position or orientation and the first range of motion; and determine a second position or orientation of the hand-held portion based on the second pose in the first degree of freedom and control the visual indicator based on the second position or orientation and the second range of motion. For example, the control system may determine an orientation of the hand-held portion in roll and a range of motion of the orientation of the hand-held portion in roll at a first time, and determine an orientation of the hand-held portion in roll and a range of motion of the hand-held portion in roll at a second time, with the roll different between the first time and the second time and the range of motion in roll also differing between the first time and the second time, and controlling the visual indicator accordingly. While this example is provided for roll, it should be understood that the same computation could be performed in pitch, translation (such as elevation), or other degrees of freedom. This provides for the visual indicator to convey a precise indication of the range of motion of the hand-held surgical instrument at all times, which can lead to better utilization of the instrument, and less interruption of the surgical procedure because the user has moved the instrument where sufficient range of motion no longer exists.

By way of example, at each elevation value, a particular theoretical range of motion for pitch and roll is achievable. Thus, as described above, it is contemplated the range of motion in pitch or roll may depend on the elevation value for which it is plotted. In other words, at a first elevation (see FIGS. 13-18), the hand-held portion may be capable of reaching a first range of pitch and roll values, and at a second elevation (see FIGS. 19-20), the hand-held portion may be capable of reaching a second range of pitch and roll values, with the first range of pitch and roll values being different from the second range of pitch and roll values. This difference in range of motion at different elevations is based on the kinematics of the actuator assembly and the joints used to couple the plurality of actuators between the tool support and the hand-held portion.

Because the range of motion of the hand-held portion potentially differs at elevation values, the outer boundaries of the various two-dimensional slice regions may also differ from one another and hence the shape and size of the two-dimensional slice regions may different from one another. For example, certain two dimensional slice regions may be symmetric, while others may be asymmetric; certain dimensional slice regions may be polygonal, while others may be circular, and so on. As show in FIGS. 19 and 20, the two dimensional slice regions are triangular in nature, whereas, in FIGS. 13-18, the two-dimensional slice regions are pentagonal in nature. More particularly, referring again to FIGS. 13-18 and FIGS. 19-20, among the plurality of two-dimensional regions that collectively define the range of motion of the hand-held portion, one of the two-dimensional regions correspond to a first range of motion in pitch and roll at a first elevation and another one of the two-dimensional regions correspond to a second range of motion in pitch and roll at a second elevation.

To understand the relationship between the pose of the hand-held and the theoretical range of motion in a scaled manner, one more positions or orientations of the hand-held portion may be modeled based on the plurality of two dimensional slice regions, in a polar coordinate system. The outer boundary of each two-dimensional region may be defined based on at least four pairs of coordinates, such as four pairs of coordinates representing pitch and roll, but is often represented by a series of lines, each having its own equation. More particularly, as mentioned above, the pose may include a pitch value, a roll value, an elevation value or values in other degrees of freedom. First, the two-dimensional region corresponding to the commanded pose of the hand-held portion is selected. In one example, this is done by selecting the two-dimensional region of the theoretical range of motion corresponding to the elevation value of the commanded pose of the hand-held portion.

The pitch value and the roll value corresponding to the elevation value for the commanded pose can be understood as a vector drawn in the two-dimensional slice region. This vector, referred to as the actual deviation vector, extends from an origin of the two-dimensional region to an endpoint defined by the pitch value and the roll value of the commanded pose in Cartesian space. More generally, the actual deviation vector can be understood to extend from the origin of at least one of the plurality of two-dimensional regions to a point defined in the polar coordinate system by the position of the hand-held portion in the second degree of freedom and the position of the hand-held portion in a third degree of freedom, with the first degree of freedom defining which of the plurality of two-dimensional regions is selected for plotting of the actual deviation vector. In certain examples, the end of the deviation vector may be characterized by one or more equations that define the portion of the boundary of the two-dimensional slice that would intersect the actual deviation vector if the actual deviation vector had an infinite magnitude The actual deviation vector exhibits a magnitude and a direction. In FIG. 14, the actual deviation vector is labeled as ADV1, and corresponds to a a roll value of x1, and a pitch value of y1, approximately 8 degrees in pitch and 14 degrees in roll. ADV1 has an angle theta2 of approximately 30 degrees and a magnitude of 16. In FIG. 16, the actual deviation vector is labeled as ADV2, and corresponds to x2, y2, which equates to −10 degrees in roll and −6 degrees in pitch. ADV2 has an angle theta4 of approximately 210 degrees and a magnitude of 12. In FIG. 17, the actual deviation vector is labeled as ADV3, and corresponds to x3, y3, which relates to −4 degrees in roll and −2 degrees in pitch. ADV3 has an angle theta5 of approximately 210 degrees and a magnitude of 5. In FIG. 20, the actual deviation vector is labeled as ADV4 and corresponds to x4, and y4, approximately 12 degrees in roll and 4 degrees in pitch. ADV4 has an angle theta8 of approximately 30 degrees and a magnitude of 13.

Referring to FIGS. 13, 15, 18, and 19, in certain implementations, the control system further determines a range of motion vector (RMV1-4) or a range of motion line (RML1-RML4) with respect to the same two-dimensional slice region that was used to model the actual deviation vector, i.e., the same elevation. The length of the range of motion lines (RML1-4) represents the range of motion that is possible for that elevation value with the particular combination of pitch and roll values, whereas the length of the range of motion vector represents the range of motion that is possible for that elevation value on one side of the origin with the particular combination of pitch and roll values. More particularly, the control system is configured to determine a range of motion line in the polar coordinate system based on the position or orientation of the hand-held portion in the first degree of freedom. The range of motion line extending from the boundary point of a two-dimensional region to a boundary point of the same two-dimensional region, at the opposite angle of the boundary point. In other words, the range of motion line can be understood as two line segments, the first having a first angle and the second segment have a line segment at the first angle +180 degrees. In this manner, the first and second line segments both extend from the same origin, and both extend from the origin to points on the outer boundary of the two-dimensional slice. The first angle is always equal to the angle of the deviation vector for each calculation. Based on this composition, the range of motion line is always colinear with the actual deviation vector, but not fully coextensive with the actual deviation vector. The magnitude of the range of motion line may be computed in various ways. In one example, an intersection point between the range of motion line and one lines that define the two-dimensional slice region. It should be understood that the range of motion line may be represented by an equation as well, and the equations for the range of motion line and the lines that define the portion of the boundary region that intersects the range of motion can be solved to determine the two sets of x, y values of the intersection of the range of motion line and the two-dimensional slice region at each end of the range of motion line. Based on these two sets of x y values, the magnitude of the range of motion line can be computed. The range of motion vector has an angle equal to the angle of the actual deviation vector. One segment of the range of motion line may consist of the range of motion vector.

In FIG. 13, the range of motion vector is labeled as RMV1, and corresponds to a pitch value of y5 and a roll value of x5, approximately 10 degrees in pitch and 18 degrees in roll. RMV1 has an angle theta1 of approximately 30 degrees and a magnitude of 21. In FIG. 15, the range of motion vector is labeled as RMV2, and corresponds to x3, y3, which equates to −12 degrees in roll and −7 degrees in pitch. RMV2 has an angle theta3 of approximately 210 degrees and a magnitude of 14. In FIG. 18, the range of motion vector is labeled as RMV3, and corresponds to x9, x9, which relates to 18 degrees in roll and 12 degrees in pitch. RMV3 has an angle theta6 of approximately 30 degrees and a magnitude of 22. In FIG. 19, the range of motion vector is labeled as RMV4 and corresponds to x11, y11, approximately 20 degrees in roll and 6 degrees in pitch. RMV4 has an angle theta7 of approximately 30 degrees and a magnitude of 21. RML1 (ending at x6, y6), RML2 (ending at x7, y7), RML3 (ending at x10, y10), and RML4 (ending at x12, y12) are each larger than their respective RMV. However, as can be appreciated from the Figures, the magnitude of the RMLs is not necessary double the magnitude of the RMVs. This is because the two-dimensional regions are not necessary symmetrical about their origin at each angle of the RMV. While the specific examples described below refer to controlling the visual indicators based on a comparison of the magnitude of the range of motion vector and the magnitude of the actual deviation vector, it is also contemplated that the visual indicators may be controlled based on the magnitude (i.e., length) of the range of motion line.

To appropriately compare the range of motion line or vector and the actual deviation vector, the direction of the deviation vector must be equal to a direction of a segment of the range of motion line or angle of the deviation vector, in other words, angle theta for each must be equal to each other. In other words, the range of motion line or the range of motion vector is computed based on the direction of the actual deviation vector Similarly, to appropriately compare magnitudes of the two vectors or compare magnitudes of the actual deviation vector and the range of motion line, range of motion line must extend through the same origin that the actual deviation vector extends from in the two-dimensional region and the range of motion vector must extend from the same origin that the actual deviation vector extends from. The range of motion line may be understood as extending to two boundary points of the two-dimensional region based on the position of the hand-held portion in one or more degrees of freedom, whereas the range of motion vector may be understood as extending to a single boundary point of the two-dimensional region. The magnitude of the range of motion one may be computed based the two-dimensional region and based on two pairs of coordinates defining the end of the range of motion; line on the two-dimensional region, i.e., the boundary points, whereas the magnitude of the range of motion vector may be computed based on the origin of the two-dimensional region and based on a pair of coordinates defining the end of the range of motion vector on the two dimensional region, the boundary point.

Regarding FIGS. 13 and 14, it should be understood that theta1 is equal to theta2, and the magnitude of ADV1 is smaller than RMV1. By mathematically comparing the magnitude of RMV1 and ADV1, the control system can approximate the percentage of range of motion remaining for the hand-held portion at any given pose of the hand-held portion relative to the closest range of motion boundary. For example, by dividing the magnitude of ADV1 by the magnitude of RMV1, it can be understood that approximately 22 percent range of motion remains for the hand-held portion at that pose of the hand-held portion relative to the closest range of motion boundary. These magnitudes of the range of motion vectors and the actual deviation vectors can be used to control the visual indicators described throughout.

Regarding FIGS. 15 and 16, it should be understood that theta3 is equal to theta4, and the magnitude of ADV2 is smaller than RMV2. By mathematically comparing the magnitude of RMV2 and ADV2, the control system can approximate the percentage of range of motion remaining for the hand-held portion at any given pose of the hand-held portion relative to the closest range of motion boundary. For example, by dividing the magnitude of ADV2 by the magnitude of RMV2, it can be understood that approximately 17 percent range of motion remains for the hand-held portion at that pose of the hand-held portion. These magnitudes of the range of motion vectors and the actual deviation vectors can be used to control the visual indicators described throughout.

Regarding FIGS. 15 and 17, it should be understood that theta3 is equal to theta5, and the magnitude of ADV3 is smaller than RMV2. By mathematically comparing the magnitude of RMV2 and ADV3, the control system can approximate the percentage of range of motion remaining for the hand-held portion at any given pose of the hand-held portion relative to the closest range of motion boundary. For example, by dividing the magnitude of ADV3 by the magnitude of RMV2, it can be understood that approximately 66 percent of the range of motion remains for the hand-held portion at that pose of the hand-held portion relative to the closest range of motion boundary. These magnitudes of the range of motion vectors and the actual deviation vectors can be used to control the visual indicators described throughout.

Regarding FIGS. 14 and 18, it should be understood that theta2 is equal to theta6, and the magnitude of ADV1 is smaller than RMV3. By mathematically comparing the magnitude of RMV3 and ADV1, the control system can approximate the percentage of range of motion remaining for the hand-held portion at any given pose of the hand-held portion. For example, by dividing the magnitude of ADV1 by the magnitude of RMV3, it can be understood that approximately 26 percent of the range of motion remains for the hand-held portion at that pose of the hand-held portion relative to the closest range of motion boundary. These magnitudes of the range of motion vectors and the actual deviation vectors can be used to control the visual indicators described throughout. It should be appreciated that the origin of the deviation vectors for 13 and 14 are different, which may result in a changing magnitude of each of the vectors.

The origin may be set for the actual deviation vector in a number of different ways. In one example, the origin may be set as the centroid of the two-dimensional region. Alternatively, the origin may set as a point other than the centroid of the two-dimensional region, such as the geometrical center. Alternatively still, the origin may be set to the range of motion in a particular degree of freedom to be unbalanced on each side of the origin. For example, by comparing FIG. 14 and FIG. 18, relative to the pitch degree of freedom, there is the possibility of greater range of motion above the origin than below the origin. This may result in asymmetrically controlling the visual indicator to lead the user to favor one side or the other side of the range of motion. This is because there is a greater likelihood that the user would be prompted to move his or her hand down than up in FIG. 14 than compared to FIG. 18. The same can be true in the roll degree of freedom. Such a configuration may be advantageous if a user has a tendency to tilt or twist his or her hand a certain way, or based on the cut selected by the user. In other words, the control system may be operated to set the origin of the actual deviation vector based on which cut is elected to be made by the user. Alternatively, the control system may present a user interface that allows the user to select a configuration that changes the origin.

Regarding FIGS. 19 and 20, it should be understood that theta7 is equal to theta8, and the magnitude of ADV4 is smaller than RMV4. By mathematically comparing the magnitude of RMV4 and ADV4, the control system can approximate the percentage of range of motion remaining for the hand-held portion at any given pose of the hand-held portion relative to the closest range of motion boundary. For example, by dividing the magnitude of ADV4 by the magnitude of RMV4, it can be understood that approximately 60 percent of the range of motion remains for the hand-held portion at that pose of the hand-held portion relative to the closest range of motion boundary. These magnitudes of the range of motion line and the actual deviation vectors can be used to control the visual indicators described throughout.

The control system is configured to control the visual indicator based on the magnitude of the actual deviation vector, the magnitude of the range of motion vector, the direction of the actual deviation vector, the direction of the range of motion vector or combinations thereof.

Additionally, by isolating and comparing the x-components (corresponding to roll) and the y-components (corresponding to pitch) of the actual deviation vector, the control system can also control the visual indicators based on the range of motion remaining in the pitch degree of freedom or the roll degree of freedom (or other degrees of freedom) independently. In other words, a pitch indicia of the visual indicator may be based on the y-component of the actual deviation vector. Similarly, a roll indicia may be controlled based on the x-component of the actual deviation vector. Furthermore, an indicia that simultaneously shows pitch and roll, referred to herein as a pitch-roll indicia, may be controlled on both components of the actual deviation vector.

Referring again to FIGS. 14, 16, and 17, as an alternative to controlling the visual indicators based on aspects of the range of motion vector, the control system may also control the visual indicators based on other computations of the range of motion. This alternative method is particularly useful in instances where a separate visual indicator is used and controlled for each degree of freedom. In this alternative example, the range of motion in a particular degree of freedom is computed based on the pose of the hand-held portion (more particularly, based on the one or more degrees of freedom of the commanded pose). For example, with reference to FIG. 14, if the commanded pose is defined as a particular roll, pitch, and elevation, a pitch range of motion is generated and a roll range of motion is generated based on aspects of the commanded pose. The commanded pose in pitch and roll is represented by x1, y1 (14 degrees in roll and 8 degrees in pitch). The range of motion, based on this pose, in the pitch degree of freedom, can be understood as the magnitude of the line extending between on points P1 and P2. In other words, the magnitude of the range of motion available in the pitch degree of freedom is defined by the orientation in the roll degree of freedom at the commanded pose (at 14 degrees of roll, what degrees in pitch are available (−6 to +12.5 degrees). This alternative method of representing the range of motion in a particular degree of freedom selects a range of motion for a degree of freedom (such as pitch) based on the pose in a different degree of freedom (roll in this example) and based on the Cartesian model of the range of motion.

Still with reference to FIG. 14, as another example, the control system may determine the range of motion in roll based on the pose in pitch, such as the commanded pose. The commanded pose in pitch is 8 degrees. The range of motion in roll based on this pose can be understood as the magnitude of the line extending between points R1 and R2. In other words, at +8 degrees in pitch, the range of motion in roll can be understood to extend from −22 to +22 degrees.

With reference now to FIG. 16, the commanded pose of the hand-held portion is determined to be −10 degrees in roll and −6 degrees in pitch (see x2, y2). Based on the value of −10 degrees in the roll degree of freedom, the range of motion in the pitch degree freedom extends from +13 to −9 degrees, or a magnitude of 22 degrees (defined by the magnitude of the line extending from P3 to P4). Based on the value of −6 degrees in in the pitch degree of freedom, the range of motion in the roll degree of freedom is computed to be −15 to +15, or 30 degrees (defined by the magnitude of the line extending from R3 to R4).

With reference to now to FIG. 17, the commanded pose of the hand-held portion is determined to be −4 degrees in roll and −2 degrees in pitch (see x3, y3). Based on the value of −4 degrees in the roll degree of freedom, the range of motion in the pitch degree freedom extends from +12.5 to −14 degrees, or a magnitude of 26.5 degrees (defined by the magnitude of the line extending from P5 to P6). Based on the value of −2 degrees in in the pitch degree of freedom, the range of motion in the roll degree of freedom is computed to be −19 to +19, or 38 degrees (defined by the magnitude of the line extending from R5 to R6).

Furthermore, while it is described that the magnitude of the roll range of motion is based on the pitch component of the commanded pose, it should be appreciated that the magnitude of the roll range of motion could also be determined based on other components of the commanded pose, such as elevation, yaw, x-axis translation or y-axis translation. The same is true for the pitch range of motion, in that it should be appreciated that the magnitude of the pitch range of motion could also be determined based on other components of the commanded pose, such as elevation, yaw, x-axis translation or y-axis translation As described above, the magnitude of the range of motion may be determined differently for different visual indicator configurations. As will be described below, for certain implementations of the visual indicators, particularly those that include a single indicia for each degree of freedom, the magnitude of the range of motion in a particular degree of freedom may be determined based on the value of the degree of freedom for a different degree of freedom and based on the Cartesian model. In other implementations of the visual indicators, such as the array of light sources, that indicate pitch and roll collectively, may rely on the magnitude of the range of motion vector described above or based on the magnitude of the range of motion line.

Referring to FIGS. 1, 21-24 and 26-27C, the visual indicator may comprise one or display screens 300, 401, 500, 600, 700UI. Each display screen may take various forms.

Referring to FIG. 21, the control system may further be configured to control the display screen 300 to display a translation indicia 302 based on the position of the hand-held portion in the first degree of freedom (a translation degree of freedom). The display screen may further include translation reference object 304 sized to denote a threshold in the translation range. The translation indicia 302 may be positioned within, or relative to, the translation reference object 304 based on the position or orientation of the hand-held portion in the translation degree of freedom and a translation threshold value. The translation threshold value may be based on a range of translation threshold values, i.e., the translation threshold value may actually include an upper translation threshold value and a lower translation threshold values. The range of translation thresholds may be based on the Cartesian model representing the three-dimensional workspace described above. In certain instances, the display screen 300 is configured to display two or more translation reference objects 304, at least one translation reference object 304 located on each side of the display screen 300. Each of the translation reference objects 304 may include a translation indicia 302 based on the position of the hand-held portion in a translation degree of freedom, such as the elevation degree of freedom. In one example, if the position of the hand-held portion is determined to be 5 in the elevation degree of freedom (as determined from the commanded pose), and the range of motion in the elevation degree of freedom is determined to be +10 to −10, the translation indicia may be positioned at approximately 75% of the height of the translation reference object. In other words, the position of the translation indicia within the translation reference object provide for a scaled understand of the commanded elevation position relative to the range of motion available for elevation.

Referring to FIG. 22, the control system may be configured to control the display screen 400 to display a roll indicia

402 based on a component of the magnitude of the actual deviator vector in the roll degree of freedom and a magnitude of the range of motion in the roll degree of freedom. As mentioned above, the magnitude of the range of motion in the roll degree of freedom may be based on a pitch component of the commanded pose. Furthermore, the display screen 401 is configured to display a roll reference object 404, wherein the roll indicia 402 is positioned relative to the roll reference object based on the x-component of the actual deviation vector and the magnitude of the range of motion in the pitch degree of freedom. The roll reference object 404 may include a plurality of spatial annotations 406 positioned at prescribed locations about an arc, each spatial annotation 406 identifying a known angle associated therewith, with each spatial annotation 406 thereby enabling a visual assessment of the roll of the hand-held portion relative to the tool support.

Referring to FIGS. 23 and 24, the control system may further be configured to display a pitch-roll indicia 502, 602 based on the magnitude of the x-component and y-component of the actual deviation vector (pitch and roll components) and the magnitude of the range of motion in the roll degree of freedom and the magnitude of the range of motion in the pitch degree of freedom. In certain instances, the pitch-roll indicia 502, 602 is a 2-d representation of a 3-D virtual object, the 2-D representation configured based on the magnitude and direction of the actual deviation vector and the magnitude and direction of the range of motion line. The exemplary 3-D object is a polygon to represent a saw blade, with the polygon having a front and a back, the back of the polygon is position opposite the front of the polygon with the front or the back of the polygon being positioned based on the magnitude of the x-component and y-component of the actual deviation vector (pitch and roll components) and the magnitude of the range of motion in the roll degree of freedom and the magnitude of the range of motion in the pitch degree of freedom. In one implementation, the control system may be configured to determine a y-component (such as pitch component) of the actual deviation vector and a magnitude of the range of motion of the hand-held portion in the pitch degree of freedom and display the pitch-roll indicia based on the y-component of the actual deviation vector and the magnitude of the pitch component of the range of motion. More particularly, the position of the 2-D representation may be scaled to an appropriate position (vertically) within the display screen based on the ratio of these values. Similarly, the control system may be configured to determine a x-component (such as the roll component) of the actual deviation vector and a magnitude of the range of motion of the hand-held portion in the roll degree of freedom, and the display screen is configure configured to display the 2-D representation may be scaled to an appropriate position (rotationally) based on the ratio of the x-component of actual deviation vector and the magnitude of the range of motion in the roll degree of freedom.

With respect to the left-most display 500 in FIG. 23, the ratio of the pitch of the hand-held portion and the magnitude of the pitch range of motion indicates that the y-component of the actual deviation vector is near the bottom of the range of motion (in the pitch-degree of freedom), and hence the front face of the pitch-roll indicia 502 is near the bottom of the screen. With the central display 502' in FIG. 23, the pitch of the hand-held portion is near the top-most range of motion in the pitch degree of freedom and hence the front face pitch-roll indicia 502 is near the top of the display. And with reference to the right-most display 502'' of FIG. 23, the pitch component of the of the hand-held portion is in the center of the range of motion in the pitch degree of freedom, And, hence the front face of the pitch-roll indicia is in the center of the display screen. For each of these, the virtual object is displayed such that what would be the rear face cannot be seen.

With respect to FIG. 24, the pitch-roll indicia 602 is positioned on the display screen 600 in a position that would indicate that the pitch component of the commanded pose is in the lower half of the magnitude of the range of motion in the pitch degree of freedom. As can be seen, the center of the pitch range of motion is between the lower pitch limit #2 and the upper pitch limit #1 (i.e., the median of the magnitude of the pitch range of motion). These upper and lower pitch limits may correspond to the outer bounds of the magnitude of the pitch range of motion Referring now to FIGS. 27A-27C, the instrument is shown withe the hand-held portion and the tool support in three different configurations. With respect to the FIGS. 27A-27C, each display screen shows roll indicia 702, elevation indicia 704, and a pitch-roll indicia 706. FIG. 27A shows the state of the roll indicia 702, the elevation indicia 704, and the pitch-roll indicia 706 based on the hand-held portion based on the hand-held portion having a deviated pitch and roll, and a centered elevation. More particularly, 27A shows the hand-held portion being at the bottom left corner of the range of motion. FIG. 27B shows the state of the roll indicia 702, the elevation indicia 704, and the pitch-roll indicia 706 based on the hand-held portion having a deviated pitch and roll, and an off-center elevation. More particularly, FIG. 27B shows the pitch-roll indicia 706 corresponding to the hand-held portion being at the top right corner of the range of motion. FIG. 27C shows the state of the roll indicia 702, the elevation indicia 704, and the pitch-roll indicia 706 based on the hand-held portion with a deviated pitch, and a desired position in the elevation degree of freedom.

In certain configurations, with reference to FIGS. 28-31, 33A, 34, 37, and 42B, the visual indicator include a plurality of light sources. More particularly, with reference to FIGS. 28-30, the visual indicator 800 may include one or more light sources corresponding to the pitch and roll degrees of freedom, known as the pitch-roll indicator 804, one or more light sources corresponding to the translation degree of freedom (i.e., elevation), known as the translation visual indicator 802, and a light source 806 configured to indicate whether the hand-held portion is within a certain threshold of the home position in more than one degree of freedom. The control system may be configured to control a state of at least one of the plurality of light sources. The control system may control the state of the plurality of light sources 802, 804, 806 based on the magnitude of the actual deviation vector, the direction of the actual deviation vector, the magnitude of the range of motion vector, or the magnitude of the range of motion line, the direction of the range of motion vector, or combinations thereof to simultaneously indicate to the user one more desired changes in one or more of a pitch orientation, a roll orientation, and a translation position. Alternatively, as mentioned above, the visual indicator may include fewer or additional light sources than described above to indicate desired changes in degrees of freedom other than elevation, pitch, and roll.

The state of the plurality of light sources 802, 804, 806 may include whether at least one light source of the plurality of light sources is on or off; a frequency of a light pulse emitted by the at least one light source; an intensity of the light emitted by the at least one light source; a color of the at least one light source; or combinations thereof. These states may be controlled via sending particular commands to the light sources, or controlling the current, voltage, or a combination thereof supplied to the plurality of light sources.

The visual indicator may include the plurality of light sources arranged in a particular manner with respect to one another to maximize delivery of information to the surgeon in an intuitive manner. In one configuration, at least three pitch-roll light sources 804 of the plurality of light sources are in a common plane with one another. This may allow for the surgeon to intuitively understand that the pitch and roll light sources 804 represent the plane of the hand-held portion 16. While three light sources are mentioned here, any number of light sources may be positioned in a common plane with one another, for example, at least four, six, eight, ten, or twelve light sources may be positioned in a common plane with one another. The at least three of the pitch-roll plurality of light sources 804 may be arranged to surround a central axis 808, collectively referred to as the array 805. In other words, the plurality of light sources in the array may be radially spaced an equidistant amount from a central point to give the appearance of a circle, or more generally, the plurality of lights may be arranged to circumscribe the central axis 808.

As described above, the circumscribing array 805 of light sources may be controlled by the control system based on the magnitude of the actual deviation vector. The circumscribing array 805 of light sources may also be controlled based on the magnitude of the range of motion vector. In other words, the control system may compare the magnitude of actual deviation vector the magnitude of range of motion vector, and based on the comparison, illuminate one or more light sources 804 that make up the array 805. The magnitude of the range of motion vector may be divided into predetermined equal fractions, such as quadrants, thirds, or some other fixed percentage intervals. These fractions of the of magnitude of the range of motion vector may be used to generate one or more deviation threshold values, which may facilitate control of the plurality of light sources. For example, the deviation threshold value may include an upper deviation threshold value and a lower deviation threshold value. However, the magnitude may be used to generate any number of thresholds, including thresholds in addition to the upper deviation threshold and the lower deviation threshold value. In addition, the magnitude may be used to generate a set of nested ranges of threshold values, for example within 20% of the center of the magnitude of the range of motion vector may be a first nested range and within 80% of the center of the magnitude of the range of motion vector.

The upper and lower deviation threshold values or ranges may be set based on a position or orientation in a particular degree of freedom that is deemed desirable. More particularly, with respect to pitch, for example, the lower lower nested range may be set to the median 20% of the range of motion (corresponding the 20% of magnitude of the range of motion vector). In other words, if the range of motion in pitch is −10 degrees to 10 degrees, the lower deviation threshold value may be set to −2 to +2 degrees. If the pitch component of the actual deviation vector is within the −2 to the +2 degree range, the control system may control the array 805 to present a particular pattern of illumination, such as all light sources being on, all light sources being off, or the light sources may be controlled to illuminate a particular color. With respect to the roll degree of freedom, the lower nested range may be set to the median 20% of the range of motion in the roll degree of freedom. In other words, if the range of motion in roll is −10 degrees to 10 degrees, the lower nested range may be set to −2 to +2 degrees. If the roll component of the actual deviation vector is within the −2 to the +2 degree range, the control system may control the array 805 to present a particular pattern of illumination, such as all light sources being on, all light sources being off, or all light sources controlled to illuminate a particular color. It is also contemplated that the array 805 may be controlled by the control system based on the lower deviation value ranges for more than one degree of freedom simultaneously. In other words, the control system may control the array 805 based on the pitch and the roll and the nested ranges corresponding to pitch and roll. Accordingly, the array may only present a particular pattern, such as all lights on or all lights off, if both the pitch component and roll component of the commanded pose are within the lower nested range values. The array may similarly be controlled based on whether such as all lights on or all lights off, if both the pitch component and roll component of the commanded pose are within the upper set of nested range values, or if the pitch and the roll component of the commanded pose are outside of both the lower set of nested range values and the upper set of nested range values.

Referring to FIG. 25, a schematic view of the array 805 of the visual indicator 800 is depicted. The control system may be further configured to identify a root light source 810 in the circumscribing array 805 of light sources. This may be computed based on a direction of the actual deviation vector. The root light source 810 may be the pitch-roll light source 804 that is closest to the angle of the deviation vector. The root light source 810 may be designated a real light source or a virtual light source. If it is a virtual light source, then another step is required which is identifying which real light source is closest to the virtual light source. By modeling with real and virtual light sources, the algorithm can be scaled depending on the mechanical configurations of the light array (the same algorithm can be applied to all different spatial configurations of LEDs). In FIG. 25, for simplicity, it will be assumed that all pitch-roll light sources 804 are real light sources. Because theta of the actual deviation vector is closest to the angle that corresponds to the second light source clockwise from the upper most light source, it is deemed the root light source 810.

The control system may be further configured to identify at least two neighboring light sources 812 that are adjacent the root light source 810 on a first side and a second side, i.e., on the right and left of the root light source 810. Once the neighboring light sources 812 are identified, the control system may be configured to control a state of the at least two neighboring light sources based on the magnitude of the actual deviation vector and the magnitude of the range of motion vector. The state of the two neighboring light sources 812 may be whether the at least two neighboring light sources are on or off. Alternatively, the control system may control the frequency of a light pulse emitted by the at least two neighboring light sources; an intensity of the light emitted by the at least two neighboring light sources; a color of the at least two neighboring light sources; or combinations thereof. The neighboring light sources 812 may include a light source in the clockwise direction relative to the root light source, and a light source in the counter-clockwise direction relative to the root light source in the array 805. In one example, if the range of motion is pitch is from −10 to +10 (derived from the range of motion vector), and the pitch value (i.e., the y-component of the deviation vector) is 8, outside of a nested range of −4 to +4), the control system may illuminate the neighboring light sources 812. If the range of motion in pitch is −10 to +10, the nested range is −4 to +4 in pitch, and the pitch component of the commanded pose is 2, which is within the range, the control system may not illuminate the neighboring light sources 812. It should be appreciated that a similar control may be employed for the other degrees of freedom, particularly roll.

In certain implementations, the control system may further be designed to identify an additional group of neighboring light sources ('the secondary neighboring light sources' 814) that are adjacent to the neighboring light sources 812 described above ('the primary neighboring light sources'). The state of this additional group of neighboring light sources 814 may be further controlled based on the magnitude of the actual deviation vector and the magnitude of the range of motion vector. For example, it is contemplated that control system may control the state of the primary neighboring light sources 812 and the secondary neighboring light sources 814 based on comparison to nested ranges. More particularly, the control system may turn on the primary neighboring light sources 812 but not the secondary neighboring light sources 814 if the magnitude of the actual deviation vector within an inner set of ranges. Furthermore, the control system may turn on the secondary neighboring light sources 814 and the primary neighboring light sources 812 if the magnitude of the actual deviation vector is outside an inner nested range but within an outer nested range. It should be appreciated that the secondary neighboring light sources 814 may include any number of light sources other than the root light source 810 and the primary neighboring light sources 812. For example, the secondary neighboring light sources 814 could include the complete remainder of pitch-roll light sources 804 in the circumscribing array 805. In other words, it should be appreciated that when the root light source 810, the primary neighboring light sources 812, and the secondary neighboring light sources 814 are all illuminated, all of the light sources in the circumscribing array 805 may be illuminated. Furthermore, it is contemplated that the control system could be configured to identify yet another group of neighboring light sources ('the tertiary neighboring light sources' 816), and the control system could control the tertiary neighboring light sources 816 in a similar manner, i.e., with a third or fourth nested range. It is also contemplated, the primary and secondary neighboring light sources may each independently include any number of light sources, but typically include a symmetrical number of light sources in the counter clockwise and clockwise direction relative to the root light source 810.

Referring again to FIG. 28, the visual indicator 800 may also include a translation visual indicator 802, which may be controlled differently from the circumscribing array 805. The control system may control a state of the light source associated with the translation visual indicator 802 based on the determined translation value and one or more translation threshold values or translation ranges. The translation threshold values or translation ranges, including nested translation ranges, may be fixed intervals or portions of the magnitude of the translation range of motion. The determined translation value is the position of the hand-held portion in the translation degree of freedom, which may be determined based on the commanded pose. The translation visual indicator 802 may include a plurality of light sources. Each of the light sources may correspond to one or more segments 803a, 803b, of the translation visual indicator. As such, the translation visual indicator 802 may include a first segment, a second segment, and optionally additional segments, each of the segments including one or more light sources. The control system may control a state of the light sources corresponding to the first segment 803a, the second segment 803b, and other segments to indicate to the user to change the translation position of the hand-held portion. In one configuration, the first segment and the second segment are on opposite sides of a midline M of the translation visual indicator 802. In such an implementation, the control system is configured to illuminate the light sources corresponding to the first segment 803a or the second segment 803b to indicate a direction of desired movement of the hand-held portion.

The first 803a and second segments 803b of the translation visual indicator 802 may be aligned on an axis 808. The axis of the translation visual indicator 802 may be perpendicular to a plane defined by the tool support 18 or the tool 20. At least a portion of the translation visual indicator 802 may be surrounded by the circumscribing array 805 of light sources. In addition, the axis of the translation visual indicator 802 may be perpendicular to a plane defined by the circumscribing array 805 of light sources. The control system may be further configured to identify a root translation light source of those light sources associated with the translation visual indicator.

However, the root translation light source is not identified using the angle of the deviation vector, but rather based on the translation value and based on the one or more translation threshold values. The control system may control the state of the light segments corresponding to the translation indicator based on the translation component of the commanded pose and the translation threshold value or the nested translation ranges. Each of the nested translation ranges may include an upper translation threshold value and a lower translation threshold value.

Figure 29B:
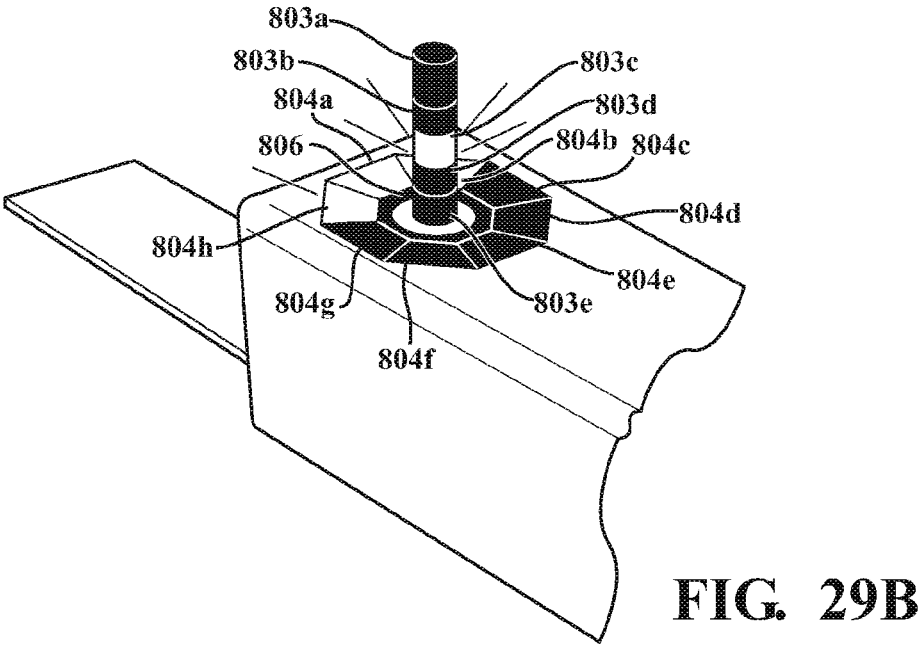

With respect to FIGS. 29A-29G, the statue of the visual indicators are described with reference to exemplary spatial configurations are described. FIG. 29A represents that that the hand-held portion is aligned with the tool support in all degrees of freedom. This is depicted on the visual indicator 800 by illuminating light segment 803c of the translation visual indicator, the median light segment, which indicates that the hand-held portion 16 is within the approximate center of the range of motion in the pitch degree of freedom (or within the innermost translation nested range). The light source 806 is also illuminated because the hand-held portion 16 is within the desired range of motion for pitch and roll degrees of freedom (the pitch component of the hand-held portion is within the innermost pitch nested range and the roll component of the hand-held portion is within the innermost roll nested range.). Furthermore, all light sources within the array 805, such as light sources 804a-804h are illuminated, to indicate that the hand-held portion is generally aligned with the tool support to desired range of motion in the pitch and roll degrees of freedom.

With respect to FIG. 29B, the hand-held portion is pitched relative to the tool support, and the user is desired to tilt the hand-held portion forward to reach the desired range of motion. In this instance, because only a change in pitch is desired, the light segment 803c of the translation visual indicator is illuminated. Furthermore, the root light source 804a is illuminated, because a change in pitch and only pitch is desired (actual deviation vector of approximately 0 degrees). Because the pitch of the hand-held portion exceeds a first threshold, two of the neighboring light sources are also illuminated light segments 804b, 804h.

Figure 29C:
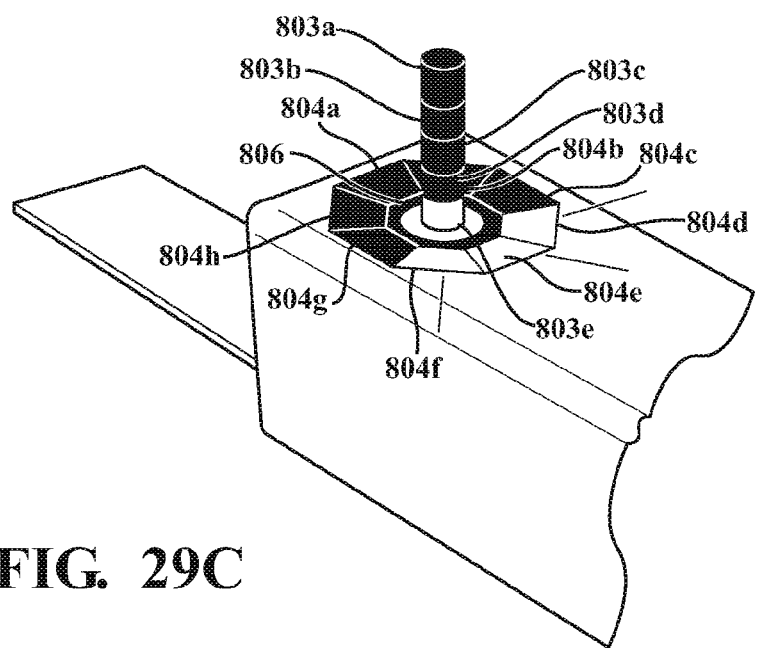

With respect to FIG. 29C, the user is desired to tilt the hand-held portion backwards in the pitch direction and to raise the hand-held portion upwards. To address the raising of the hand-held portion, light source 803e of the translation indicator is illuminated because the translation is near the lowermost translation threshold value. To address the change in pitch desired, the root light source is identified as 804e (actual deviation vector having an angle of approximately 180 degrees). Based on the magnitude of the change in pitch desired, neighboring light sources 804d and 804f are also illuminated.

Figure 29D:
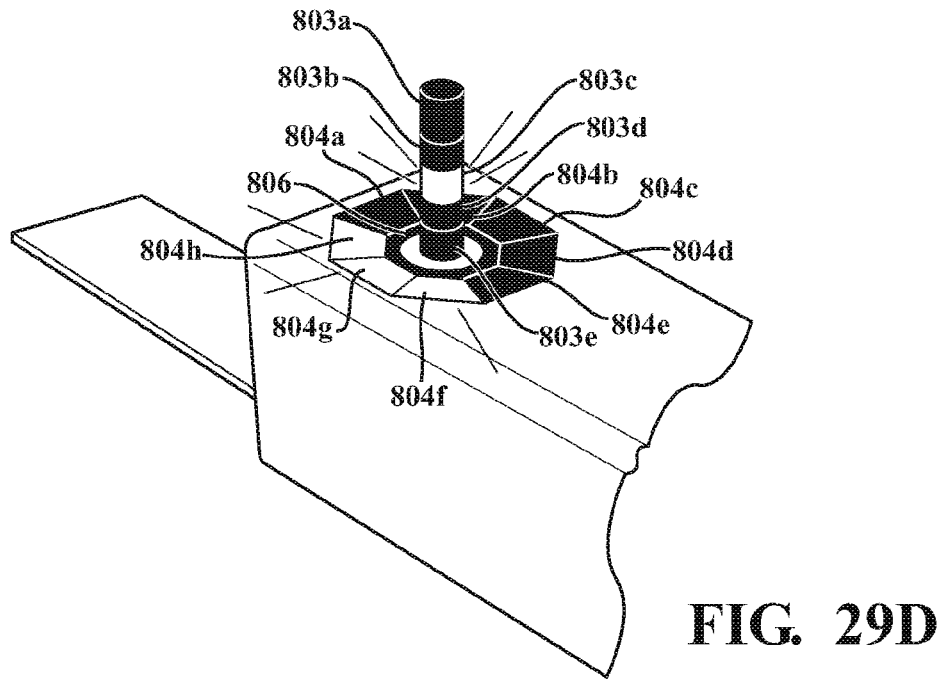

With respect to FIG. 29D, the user is desired to twist the hand-held portion clockwise in the roll degree of freedom and no change in elevation is required. This is depicted on the visual indicator 800 by illuminating light segment 803c of the translation visual indicator, which indicates that the hand-held portion 16 is within the approximate center of the range of motion in the pitch degree of freedom. The root light source 804g is identified and illuminated (actual deviation vector having a direction of approximately 270 degrees). Based on the degree of roll movement required, neighboring pitch-roll light sources 804h and 804f are also illuminated.

Figure 29E:
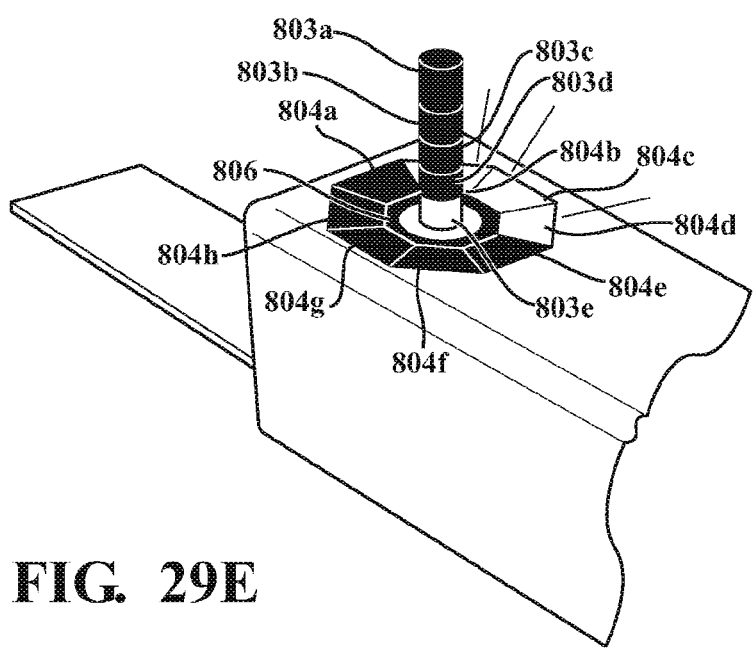

With respect to FIG. 29E, the user is desired to twist the hand-held portion counter-clockwise in the roll degree of freedom. To address the raising of the hand-held portion, light source 803e of the translation indicator is illuminated because the translation is near the lowermost translation threshold value. The root light source 804c is identified and illuminated (actual deviation vector having a direction of approximately 90 degrees). Based on the degree of roll movement required, light sources 804b and 804d are also illuminated, which can be considered the neighboring light sources or neighboring light segments.

Figure 29F:
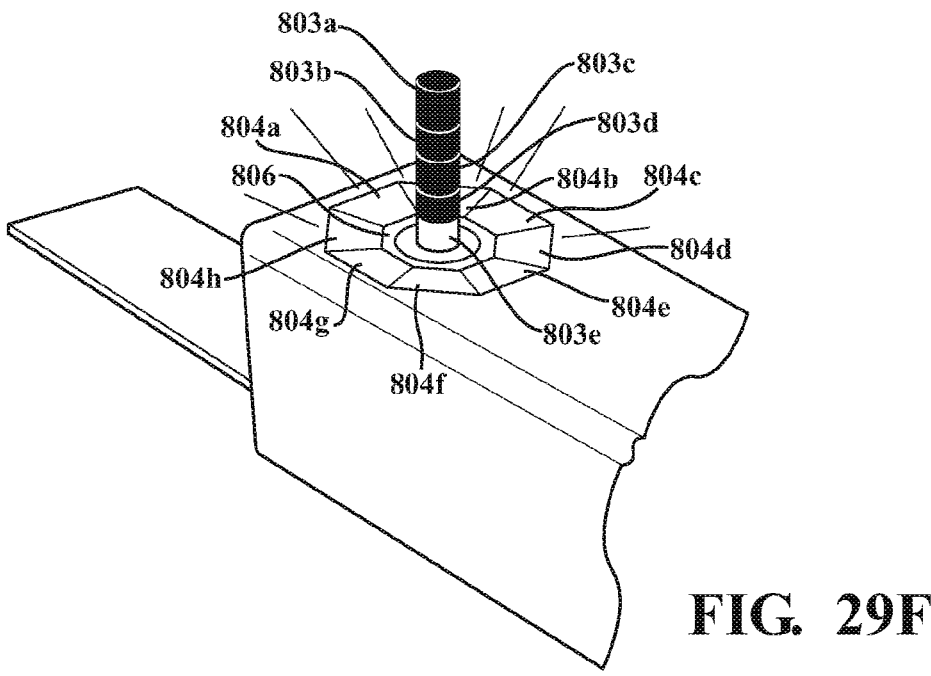

With respect to FIG. 29F, the user is desired to raise the hand-held portion up, i.e., change the elevation, and no change is desired in the pitch and roll degrees of freedom. To address the raising of the hand-held portion, light source 803e of the translation indicator is illuminated because the translation is near the lowermost translation threshold value, or is outside, on the lower side, of the outermost translation nested range. The light source 806 is also illuminated because the pitch and roll components of the commanded pose of the hand-held portion 16 is within the inner most nested ranges for pitch and roll degrees of freedom. Furthermore, all light sources within the array 805, such as light sources 804a-804h are illuminated, to indicate that the hand-held portion is generally aligned with the tool support to desired range of motion in the pitch and roll degrees of freedom.

Figure 29G:
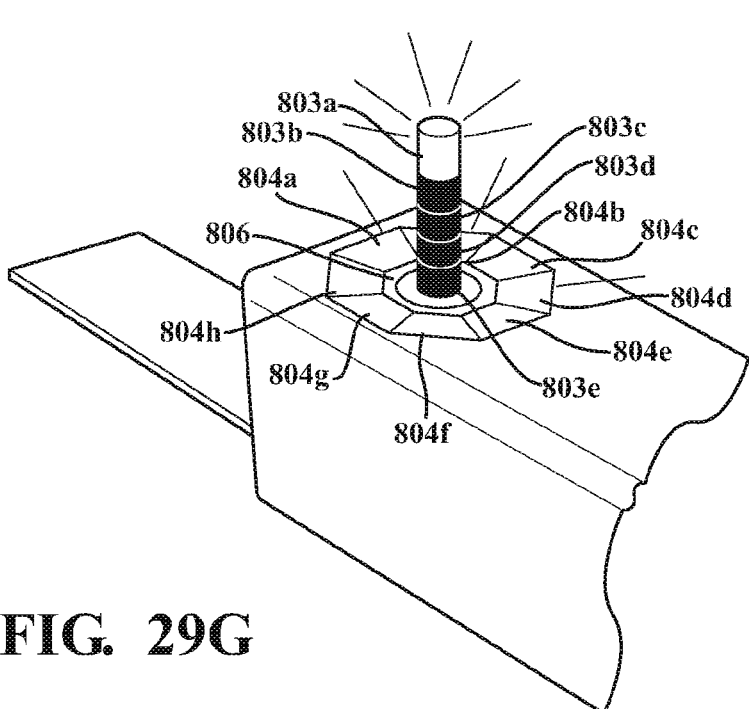

With respect to FIG. 29G, the user is desired to lower the hand-held portion down, i.e., change the elevation, and no change is desired in the pitch and roll degrees of freedom. To address the lowering of the hand-held portion, segment 803a of the translation indicator is illuminated because the translation is near the uppermost translation threshold value. The light source 806 is also illuminated because the hand-held portion 16 is within the desired range of motion for pitch and roll degrees of freedom. Furthermore, all light sources within the array 805, such as light sources 804a-804h are illuminated, to indicate that the hand-held portion is generally aligned with the tool support to desired range of motion in the pitch and roll degrees of freedom.

Figures 30A, 30B, 30C, 30D, 30E:
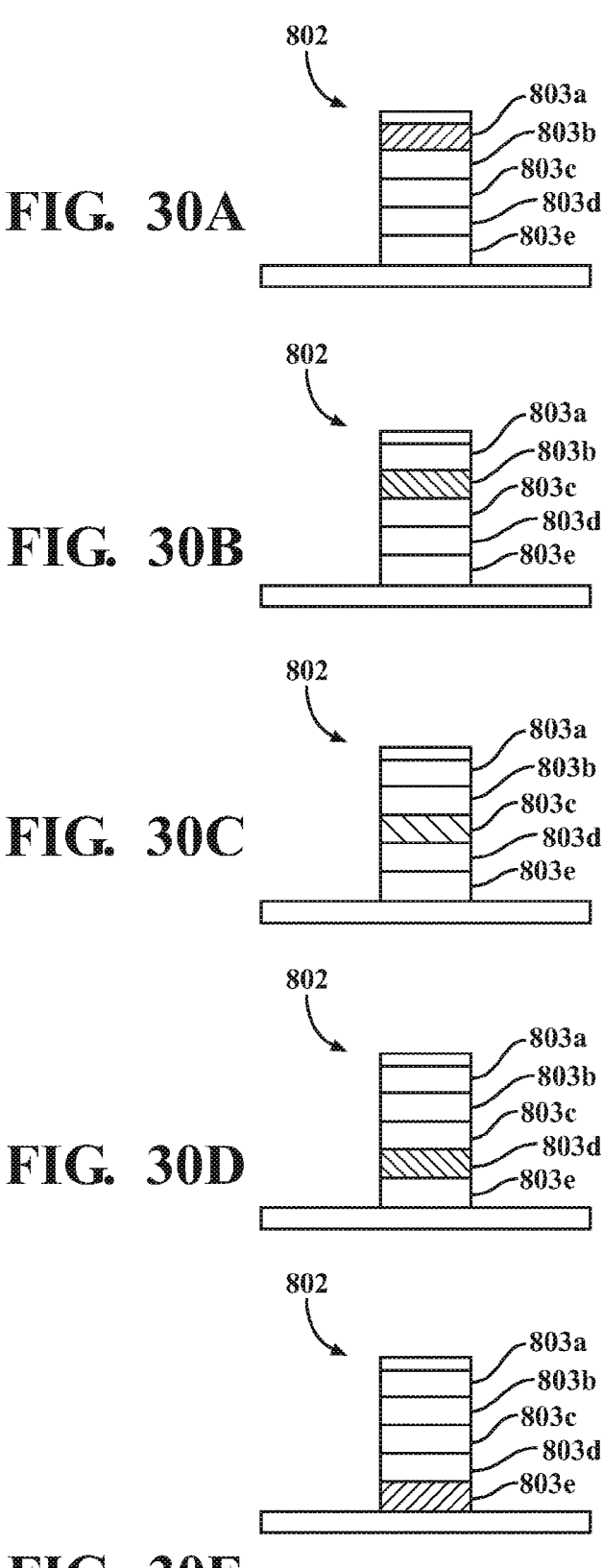

With respect to FIG. 30A-30E, the translation visual indicator 802 is further described. The translation visual indicator 802 can include a plurality of light segments 803a-803e. Each light segment may be associated with one or more light sources. The translation threshold value(s) may comprise a range of translation threshold values. The range of the translation threshold values may be based on the Cartesian model representing the three-dimensional workspace of the tool support relative to the hand-held portion. For example, if the translation value of the hand-held portion is 5, and the range of motion in translation is −10 to +10, the control system would identify the second segment (803b) of the five segment shown as part of the translation indicator (See FIG. 30B). If the translation value is 10, the upper most light source (803a) in the translation visual indicator 802 may be illuminated (See FIG. 30A). One or more of the light segments 803a-803e may be configured to emit a different color than the other light segments. For example, the upper most and lower most light segments (803a) and 803(e) may be configured to emit the same color, whereas the central light segment 803c may be configured to emit a different color from the upper most and lower most light segments. Further still, the intermediate light segments (803b and 803d) may be configured to emit a third color light. By emitting different color lights depending on the translation value, the user can understand how close he or she is to the range of motion limits in translation. FIG. 30A indicates that the elevation value is close to the top of the range of motion limit for elevation. FIG. 30B indicates that the elevation value is in between the top of the range of motion t threshold (which would cause illumination of 803a), and a central range of motion threshold (which would cause illumination of 803c). FIG. 30C has 803c illuminated, which indicates that the elevation value is between a central range of motion threshold range. FIG. 30D is the inverse of FIG. 30B (with segment 803d illuminated), and FIG. 30E is the inverse of FIG. 30A, with 803e illuminated.

FIG. 31 is another representation of a visual indicator 900. The central post 902 may function like the translation visual indicator 802 described above, and include a plurality of segments controlled as described above with respect to FIGS. 30A-30E. The visual indicator 900 may further include the array 905, which may include a plurality of light sources. The array 905 may function as described above with respect to the array 805 and may include a plurality of light sources similar to array 805.

Importantly, based on the visual indicators described above, an operator of the hand-held robotic system can visually understand whether the blade support 18 has a desired range of motion relative to the hand-held portion 16. Particularly, when in the home position, the amount of adjustability of the actuators 21, 22, 23 is maximized to keep the tool 20 at a desired pose. Various levels of adjustment are possible depending on the particular geometry and configuration of the instrument 14. In some examples, when all the actuators 21, 22, 23 are in their home positions, the tool 20 may be adjusted in pitch orientation about +/−18° relative to the home position, assuming zero changes in the roll orientation and no z-axis translation. In some examples, when all the actuators 21, 22, 23 are in their home positions, the tool 20 may be adjusted in roll orientation about +/−33° relative to the home position, assuming zero changes in the pitch orientation and no z-axis translation. In some examples, when all the actuators 21, 22, 23 are in their home positions, the tool 20 may be adjusted in z-axis translation about +/−0.37 inches relative to the home position, assuming zero changes in the pitch orientation and roll orientation. The tool 20 may be adjusted in pitch, roll, and z-axis translation simultaneously, sequentially, or combinations thereof during operation.

FIGS. 32A-C shows a representations of the display screen in which indicia provides intuitive information to the user as to the pitch and roll of the hand-held portion, the or elevation of the hand-held portion. The indicia provided may be indicative of the plane of the hand-held portion relative to the desired cutting plane previously introduced. The indicia may include a circle or other marking representative of desired cutting plane. The circle may be static. The indicia may further include an "X" or other type of marking that is movable relative to the circle. Should the plane of the hand-held portion deviate from the desired cutting plane in pitch, roll, or both, the X may be displayed outside of the circle. For example, deviations in pitch may include the X being displayed above or below the circle, and deviations in roll may include the X being displayed to the right or left of the circle. With the above convention, FIG. 32B shows the plane of the hand-held portion being angled upwardly relative to the desired cutting plane and rolled to the left of the desired cutting plane. FIG. 32C shows the deviation to be less than that of FIG. 32B. The indicia may also incorporate the z-axis position of the hand-held portion relative to the desired cutting plane. In certain implementations, a thickness of the circle may be altered based on the z-axis position of the hand-held portion relative to desired plane. For example, as the hand-held portion is moved upwardly or downwardly, the thickness of the circle increases, as shown in FIG. 32B. The circle may increase in thickness to a predetermined maximum, or be completely filled in upon the hand-held portion reaching a certain pose relative to the desired cutting plane. The display may also provide for a visual working zone with the indicia superimposed on the visual working zone.

FIG. 33A shows the indicia being displayed on an array of LED lights, for example, a five-by-five array. The array is shown as being integrated into the instrument, but may alternatively be shown on the display previously introduced. The selective lighting of the LEDs lights may be such that, when the pitch, roll, and z-axis position of the hand-held portion is correct or at a desired position, a single, centered LED light of the array is illuminated. Otherwise, the illuminated LED lights provide intuitive information as to which one or more of aspects of the pose of the hand-held portion is incorrect. Deviations in pitch and the roll of the hand-held portion may be shown by less than a completed square of the LED lights being illuminated. Further, deviations in the pitch and the roll of the hand-held portion may be shown by the illuminated LED lights not being centered on the array. With the above convention, FIG. 33A(1) show the hand-held portion deviating in one of pitch and roll. In other words, the less than a complete square of the LEDs is illuminated, however the would-be completed square (if the pitch or the roll was correct) is centered on the array. Further, the absence of the lower-right corner of the square indicates to the user that the hand-held portion needs to be generally adjusted in the lower-right direction to rectify the pitch, the roll, or both. FIG. 33A(2-3) shows the hand-held portion deviating in both of pitch and roll. Not only is less than a complete square of the LEDs illuminated, but also the illuminated LEDs of the would-be completed square are not centered on the array. In FIG. 33A(4), the pitch and the roll of the hand-held portion being correct, but the hand-held portion 16 is deviated in the z-axis or elevation. As the instrument 14 is moved upwardly or downwardly and the hand-held portion approaches the desired plane, the size of the square becomes smaller, as shown incrementally in 33_a_ (4-6). FIG. 33A(6) shows the single, centered LED light of the array illuminated, indicative of the when the pitch, roll, and z-axis position of the hand-held portion being correct, as mentioned.

FIG. 33B utilizes a similar arrangement with a progressively illuminating circle as opposed to a square array. Deviations in pitch and the roll of the hand-held portion may be shown by less than a completed circle being illuminated. FIG. 33B(1) of lower-left arc of the circle being absent indicates to the user that the hand-held portion needs to be generally adjusted in the lower-left direction to rectify the pitch, the roll, or both. The z-axis or elevation may be indicated by a position of a dot or other marking along a vertical line bifurcating the circle. Thus, FIG. 33B(2) shows the pitch and the roll of the hand-held portion being correct, as the circle is illuminated, but deviating in the z-axis, as the dot is not centered on the vertical line. As the hand-held portion is moved upwardly or downwardly, the dot moves towards the center of the circle. FIG. 33B(3) shows the circle being illuminated and the dot centered along the vertical line within the circle, indicative of when the pitch, roll, and z-axis position of the hand-held portion being correct.

Referring now to FIG. 34, the visual indicator may include a first visual indicator 1000', a second visual indicator 1000" a third visual indicator 1000''', and a fourth visual indicator 1000''''. In the version shown, each of the visual indicators 1000, 1000', 1000", 1000''' include one or more illumination sources coupled to the control system. In some versions, the illumination sources comprise one or more LEDs which can be illuminated with different intensities/colors. The visual indicators 1000, 1000', 1000", 1000''' shown in FIG. 34 may be post-like in structure and extend upwardly from an upper surface of the tool support 18. The visual indicators 1000, 1000', 1000", 1000''' may be provided in a rectangular arrangement, as shown, or a square or other suitable arrangement. The color of the visual indicators 1000, 1000', 1000", 1000''', and more particularly differences in color between the visual indicators 1000, 1000', 1000", 1000''' may be indicative of the pitch and roll of the hand-held portion relative to the desired plane. For example, the distal two of the visual indicators 1000, 1000', 1000", 1000''' being at least predominately yellow and the proximal two of the visual indicators 1000, 1000', 1000", 1000''' being at least predominately red may be indicative of deviation in pitch relative to the desired cutting plan. Likewise, the left two of the visual indicators 1000, 1000', 1000", 1000''' being at least predominately yellow and the right two of the visual indicators 1000, 1000', 1000", 1000''' being at least predominately red may be indicative of deviation in roll relative to the cutting plane. In other words, causing the colors of all of the visual indicators 1000, 1000', 1000", 1000''' to be the same, may indicate that the orientation of the hand-held portion relative to the desired cutting plane is correct. It is contemplated that less than four of the visual indicators 1000, 1000', 1000", 1000''' may be illuminated to indicate deviation in pitch, roll, or both. The color (not necessarily the differences in color) of visual indicators 1000, 1000', 1000", 1000''' may be indicative of the z-axis position relative to the desired cutting plane. For example, the visual indicators 1000, 1000', 1000", 1000''' being red or yellow may be indicative of deviation in the z-axis position relative to the desired cutting plane, and the visual indicators 1000, 1000', 1000", 1000''' being green may be indicative of the hand-held portion being in the desired position. Taken together, each of the visual indicators 1000, 1000', 1000", 1000''' being the same color, namely green, may be representative of hand-held portion being correct in pitch, roll, and z-axis position.

FIGS. 35A, 35B, and 35C each represent a display screen with a vertical line with a dot to be centered indicative of correct z-axis position. The indicia of FIGS. 35A and 35B include a horizontal line intersecting the vertical line at a center point, and an articulate line intersecting the center point. The indicia may further include additional dots or markings indicative of position in pitch and roll relative to the desired cutting plane. More particularly, a horizontal position of the dot on the horizontal line may be representative of pitch relative to the desired cutting plane, and a position of the dot on the arcuate line may be representative of roll relative to the desired cutting plane. The use of the arcuate line may be particularly intuitive given the movements resulting in deviating in roll; i.e., rotation about the x-axis. When the pitch, roll, and z-axis position of the hand-held portion are correct, the dots converge on the intersection point. FIG. 35A is representative of the hand-held portion being off in pitch, roll, and z-axis position. The deviation in roll is greater than the deviation in pitch, as the dot on the arcuate line is farther from the intersection point than the dot on the horizontal line. FIG. 35B is representative of the pitch and the roll of the hand-held portion being correct, but the hand-held portion being deviating in z-axis position. FIG. 35C is representative of the hand-held portion being correct in pitch, roll, and z-axis position, as the indicia appears as a singular dot at the intersection point.

FIGS. 36A-36C utilizes crosshairs to be representative of any deviation pitch, roll, and z-axis position relative to the desired cutting plane. A horizontal line of the crosshairs may be representative of pitch, and a vertical line of the crosshairs may be representative of roll. An intersection of the horizontal and vertical lines may be representative of the z-axis position relative to an origin, for example, a center of the dashed box shown in FIG. 36A-36C. A progressively thickening one or both of the horizontal and vertical lines may be indicative of deviation in pitch. Thus, FIG. 36A is representative of the hand-held portion deviating in pitch and roll, as the vertical line of the crosshairs is in perspective and the crosshairs are rotated. FIG. 36B is further representative of the hand-held portion deviating in z-axis position, as the crosshairs are not centered on within the box. FIG. 36B is representative of the hand-held portion being correct in pitch and roll, but the hand-held portion being deviated in z-axis position. FIG. 36C is representative of the hand-held portion being correct in pitch, roll, and z-axis position. FIG. 36C also shows the box transforming with the hand-held portion being in the desired position in all controlled degrees of freedom.

Referring to FIG. 37, the visual indicator 1100 may include a first visual indicator 1102, a second visual indicator 1104, and a third visual indicator 1106. The visual indicators 1102, 1104, 1106 of the implementation shown are spherical-shaped LEDs coupled to the tool support and arranged linearly in a front-to-back fashion. The visual indicator 1100 may include a fourth visual indicator 1108 and a fifth visual indicator 1110. The visual indicators 1108, 1110 of the implementation shown are spherical-shaped LEDs coupled to the tool support, and are relatively smaller in diameter than that of the first, second, and third visual indicators 1102, 1104, 1106. The visual indicators 1102, 1104, 1106, 1108, 1110 may be configured to illuminate in a single color, for example, white, blue, grey, black, etc. The visual indicators 1102, 1104, 1106 may be directed to showing pitch and z-axis position of the hand-held portion relative to the desired cutting plane, however other schemes using combinations of the visual indicators 1102, 1104, 1106 are contemplated. The fourth and fifth visual indicators 1108, 1110 may be directed to showing roll of the hand-held portion relative to the desired cutting plane, and thus positioned opposite the row of the first, second, and third visual indicators 1102, 1104, 1106. Thus, illumination of the fourth visual indicator 1108 positioned to the left of the first, second, and third visual indicators 1102, 1104, 1106 with a certain color may be indicative of counterclockwise roll, and illumination of the fifth visual indicator 1110 positioned to the right of the of the first, second, and third visual indicators 1102, 1104, 1106 with a certain color may be indicative of clockwise roll. For the first, second, and third visual indicators 1102, 1104, 1106, illuminating one or more with certain colors may be indicative of deviation in pitch, elevation, or both. In one example, the hand-held portion may be manipulated until the forwardmost visual indicator 1102 is blue, and the second and third visual indicators 1104, 1106 are black, thereby creating a single focal point for the user.

Referring now to FIG. 38, the visual indicator 1200 may be mechanical in form. In particular, the visual indicator 1200 uses alignment features on each of the hand-held portion 16 of the instrument 14 and the tool support 18 of the instrument 14. The guidance array 1200 gives the user visual feedback as to how the tool support 18 is positioned relative to the hand-held portion 16 in an intuitive, familiar manner. In instances where the instrument 14 is a sagittal saw with the tool 20 being a saw blade being oriented parallel to the ground, the features to be described on the hand-held portion 16 may be on the same plane as that of the tool 20 when the instrument 14 is at the nominal or "home" position. A leveler 1210 is coupled to the hand-held portion 16. The leveler 1210 may include two plates 1212 separated by a recess 1214 or void. The plates 1212 are arranged coplanar to one another. The leveler 1210 is coupled to the hand-held portion 16 such that, when the tool 20 is at the home position, the tool 20 is parallel to the plates 1212. In one example, the tool 20 may be coplanar with the plates 1212. Deviation in pitch and roll is readily ascertainable visually based on the relative orientation of the tool 20 to the plates 1212 of the leveler 1210.

FIG. 39 shows another implementation of the visual indicator 1300 in which the leveler 1310 is coupled to the hand-held portion 16. The leveler 1310 includes an arm 1312 coupled to the hand-held portion 16 extending to a sight 1314 adjacent the tool support 18. The sight 1314 may be an opening with crosshairs disposed about the opening. A beacon 1316 may be coupled to the tool support 18 and arranged to be aligned with the sight 1314 when the tool 20 is at the home position. The beacon 1316 may also include crosshairs configured to be aligned to the crosshairs of the sight 1314. It is appreciated that as the tool 20 and the tool support 18 move relative to the hand-held portion 16 during operation of the instrument 14, the beacon 1316 moves relative to the sight 1314. With the instrument 14 maintaining the desired cutting plane as described, the user may manipulate the hand-held portion 16 in a manner to align the beacon 1316 with the sight 1314.

FIG. 40 show another schematic representation of the instrument 14 with another implementation of the visual indicator 1400. The visual indicator 1400 includes at least one arm 1402 coupled to the hand-held portion 16. The illustrated implementation includes a plurality of arms 1402, optionally arranged equiangularly in a star-like pattern. The visual indicator 1400 includes at least one fork 1408 coupled to the tool support 18, and the illustrated implementation includes five forks 1408 at the end of other arms 1404 arranged equiangularly in a star-like pattern complementary to the star-like pattern of the arms 222. At the end of each arm 1402 is a geometry 1406, for example a sphere, configured to be situated between the tines of the fork 1408 when the tool 20 is at the home position. More particularly, the geometries 1406 may be coplanar with and equally spaced from opposing tines of the fork 1408 when the tool 20 is at the home position. Again, the tool 20 and the tool support 18 move relative to the hand-held portion 16 during operation of the instrument 14. The geometries 1406 move relative to the forks 1408. The lack of alignment is readily apparent visually to the user, and the user may manipulate the hand-held portion 16 in a manner to realign the geometries 1406 with the forks 1408.

Referring to FIG. 41, another schematic representation of the instrument 14 with a visual indicator 1500 in which a window 1502 is disposed within the hand-held portion 16 adjacent to the tool support 18. More specifically, a proximal end of the tool support 18 is visible through the window 1502. The hand-held portion 16 and the proximal end 230 of the tool support 18 may include complementary markings configured to be aligned when the tool 20 is in the home position. The marking on the proximal end of the tool support 18 may be a horizontal line, and the marking on the hand-held portion 16 being opposing projections adjacent the window 1502. With the tool 20 in the home position, the horizontal line and the opposing projections are coplanar. Should the tool 20 and the tool support 18 move relative to the hand-held portion 16, the complementary markings are no longer in alignment.

Referring to FIG. 42A, another exemplary visual indicator 1600 is shown on a display screen. This includes similar translation indicia 1602 as described above, with a different visualization for pitch and roll indicia 1604. The circles and cross-hairs may each move relative to one another based on the pitch value, roll value, or both, and the angle of the actual deviation vector. Similarly, it is contemplated that the position of the circles or crosshairs may be controlled based on the magnitude, direction, or both, of the actual deviation vector or the range of motion vector.

Referring to FIG. 42B, the visual indicator 1700 may include three linear arrangement of visual indicators 1702, 1704, 1706 intersecting one another. The color of each segment of the visual indicators, and more particularly differences in color between the visual indicators may be indicative of the pitch and roll of the tool 20 relative to the desired cutting plane. The plurality of light sources may be controlled in a manner described above with respect to FIGS. 29 and 30. The visual indicator 1700 may be coupled to the tool support.

Referring to FIG. 42C, another exemplary visual indicator 1800 is shown. The position of the cross-hair may change based on the pitch, the roll, or both of the hand-held portion. The position of the cross-hair may be controlled in the same manner as the pitch-roll indicia described above with respect to FIGS. 24, 26, and 27.

The instrument controller 28 may switch enable the visual indicator based on an input signal, such as activation of an input device (e.g. footswitch, trigger, mouse click or touch screen press on navigation UI, 38, etc.). Alternatively, the instrument controller 28 may be configured enable the visual indicator based on the position of the tool 20 and the position of a reference location of bone in a known coordinate system, such as patient trackers 54, 56. A reference location may be a point, surface, or volume in the coordinate system used to locate the instrument 14 relative a target state, such as a target object. In one particular implementation, the reference location is a planned entry of the bone. For example, the reference location may be a surface of a bone, a point within a bone, an imaginary or virtual point within the known coordinate system, a volume in the coordinate system, or a combination thereof. The position or orientation of the reference location is known with respect to the patient tracker through registration and suitable planning steps. The instrument controller 28 may switch modes or operate differently based on a distance parameter computed between two objects, such as a distance between the tool and a reference location. A distance parameter may be a distance (e.g. how far apart two objects are), magnitude (the direction of the distance relative to one object), or both. In some examples, the instrument controller 28 may switch modes when the distance parameter has a direction away from bone and a magnitude greater than a first threshold value.

In this application, including the definitions below, the term "controller" may be replaced with the term "circuit." The term "controller" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The controller(s)/control system may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The controller may communicate with other controllers using the interface circuit(s). Although the controller may be depicted in the present disclosure as logically communicating directly with other controllers, in various configurations the controller may actually communicate via a communications system. The communications system includes physical or virtual networking equipment such as hubs, switches, routers, and gateways. In some configurations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various configurations, the functionality of the controller may be distributed among multiple controllers that are connected via the communications system. For example, multiple controllers may implement the same functionality distributed by a load balancing system. In a further example, the functionality of the controller may be split between a server (also known as remote, or cloud) controller and a client (or, user) controller.

Some or all hardware features of a controller may be defined using a language for hardware description, such as IEEE Standard 1364-2005 (commonly called "Verilog") and IEEE Standard 10182-2008 (commonly called "VHDL"). The hardware description language may be used to manufacture or program a hardware circuit. In some configurations, some or all features of a controller may be defined by a language, such as IEEE 1666-2005 (commonly called "SystemC"), that encompasses both code, as described below, and hardware description.

The various controller programs may be stored on a memory circuit. The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input or output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SENSORLINK, and Python®.

Clause I. A method of controlling a visual indicia of a hand-held robotic system for use with a saw blade, the robotic system including a localizer, and a hand-held instrument having a hand-held portion to be held by a user and a blade support movably coupled to the hand-held portion to support the saw blade, an actuator assembly operatively interconnecting the blade support and the hand-held portion, the actuator assembly including a plurality of actuators, the blade support including a saw drive motor, the method comprising the steps of: determining a position or orientation of the hand-held portion in a first degree of freedom in a known coordinate system; determining a range of motion of the tool support in a second degree of freedom based on the position or orientation of the hand-held portion in the first degree of freedom; determining a position and/or orientation of the hand-held portion in the second degree of freedom in the known coordinate system; and controlling the visual indicator based on the position and/or orientation of the hand-held portion and the range of motion in the second degree of freedom.

Clause II. A hand-held robotic system for use with a tool, the system comprising: an instrument comprising; a hand-held portion to be held by a user and a tool support coupled to the hand-held portion, the tool support comprising a tool drive motor to drive motion of the tool; and an actuator assembly operatively interconnecting the tool support and the hand-held portion to move the tool support to move the tool in a plurality of degrees of freedom relative to the hand-held portion to align the tool, the actuator assembly including a plurality of actuators; a visual indicator to guide the user; a control system coupled to the plurality of actuators, the control system configured to: determine a position and/or orientation of the hand-held portion in a first degree of freedom and a second degree of freedom in a known coordinate system; and control the visual indicator based on the position and/or orientation of the hand-held portion in the first and second degrees of freedom and a range of motion of the tool support relative to the hand-held portion in the first and second degrees of freedom.

Clause III. A method of controlling a visual indicia of a hand-held robotic system for use with a saw blade, the robotic system including a localizer, and a hand-held instrument having a hand-held portion to be held by a user and a blade support movably coupled to the hand-held portion to support the saw blade, an actuator assembly operatively interconnecting the blade support and the hand-held portion, the actuator assembly including a plurality of actuators, the blade support including a saw drive motor, the method comprising the steps of: determining a first pose of the hand-held portion in a known coordinate system; determining a first range of motion in a first degree of freedom based on the first pose; determining a second pose of the hand-held portion in the known coordinate system; determining a second range of motion in the first degree of freedom based on the second pose, wherein the first and second range of motion are different and the first and second poses are different;

determining a first position and/or orientation of the handheld portion based on the first pose in the first degree of freedom and control the visual indicator based on the first position and/or orientation and the first range of motion; and determining a second position and/or orientation of the handheld portion based on the second pose in the first degree of and control the visual indicator based on second position and/or orientation and the second range of motion.

Clause IV. A hand-held robotic system for use with a surgical tool, the system comprising: an instrument comprising; a hand-held portion to be held by a user and a tool support coupled to the hand-held portion, the tool support comprising a tool drive motor to drive motion of the tool; and an actuator assembly operatively interconnecting the tool support and the hand-held portion to move the tool support to move the tool in a plurality of degrees of freedom relative to the hand-held portion, the actuator assembly including a plurality of actuators; a visual indicator to guide the user where to place the hand-held portion; a control system coupled to the plurality of actuators and the visual indicator, the control system being configured to:

determine a position and/or orientation of the tool support in a first degree of freedom in a known coordinate system; determine a range of motion of the tool support in a second degree of freedom based on the position and/or orientation of the tool support and/or the hand-held portion in the first degree of freedom; determine a position and/or orientation of the tool support and/or the hand-held portion in the second degree of freedom in the known coordinate system; and control the visual indicator based on the position and/or orientation of the hand-held portion and/or the tool support and the range of motion in the second degree of freedom.

Clause V. A hand-held robotic system for use with a surgical tool, the system comprising: an instrument comprising; a hand-held portion to be held by a user and a tool support coupled to the hand-held portion, the tool support comprising a tool drive motor to drive motion of the tool; and an actuator assembly operatively interconnecting the tool support and the hand-held portion to move the tool support to move the tool in a plurality of degrees of freedom relative to the hand-held portion, the actuator assembly including a plurality of actuators; a visual indicator to guide the user where to place the hand-held portion; a control system coupled to the plurality of actuators and the visual indicator, the control system being configured to: determine a first pose of the tool support in a known coordinate system; determine a first range of motion in a first degree of freedom based on the first pose; determine a second pose of the tool support in the known coordinate system; determine a second range of motion in the first degree of freedom based on the second pose, wherein the first and second range of motion are different and the first and second poses are different; determine a first position and/or orientation of the tool support based on the first pose in the first degree of freedom and control the visual indicator based on the first position and/or orientation and the first range of motion; and determine a second position and/or orientation of the tool support based on the second pose in the first degree of freedom and control the visual indicator based on second position and/or orientation and the second range of motion.

Throughout this disclosure, certain indicia are described with particular degrees of freedom—e.g., the pitch-roll indicia. It should be appreciated than any of the indicia described throughout could be used to indicate the position and/or orientation in other degrees of freedom in a similar way, such as yaw, x-axis translation, or y-axis translation. It may be useful to convey the position and/or orientation of these other degrees of freedom depending on the actuator assembly used and the degrees of freedom available for movement of the tool relative to the hand-held portion Any of the control systems claimed herein may also feature one or more of the features described below. The control system may be further configured to determine, in a known coordinate system, a pose of the saw blade, a pose of the hand-held portion, a target pose of the saw blade, and a boundary, and control the plurality of actuators to align the saw blade in the plurality of controlled degrees of freedom based on the pose of the hand-held portion and the target pose of the saw blade. The target pose may be a target plane defined in at least three degrees of freedom. The boundary may be a boundary mesh, wherein controlling the saw drive motor comprises controlling a motor parameter of the saw drive motor at a first value and a second value, wherein the first value is different than the second value, the controller operable to change operation from the first value to the second value based on the boundary mesh and based on the pose of the saw blade. The motor parameter may be selected from a group comprising speed, torque, current, acceleration, or combinations thereof. The control system determining a distance parameter with respect a portion of the saw blade and the boundary, wherein controlling the saw drive motor is based on the distance parameter. The control system may be configured to determine a position of each of the actuators of the plurality of actuators, and determine the pose of the hand-held portion based on the pose of the saw blade and the position of each of the actuators of the plurality of actuators. The control system may configured to determine a pose of a tracker coupled to the blade support in the known coordinate system, and determine the pose of the saw blade based on the pose of the tracker coupled to the blade support in the known coordinate system. The control system may also be configured to determine a pose of a tracker coupled to the hand-held portion in the known coordinate system; and determine the pose of the hand-held portion based on the pose of the tracker coupled to the hand-held portion in the known coordinate system.

The invention claimed is:

1. A hand-held robotic system for use with a surgical tool, the system comprising:

an instrument comprising;

a hand-held portion to be held by a user and a tool support coupled to the hand-held portion, the tool support comprising a tool drive motor to drive motion of the surgical tool; and an actuator assembly operatively interconnecting the tool support and the hand-held portion to move the tool support to move the surgical tool in a plurality of degrees of freedom relative to the hand-held portion, the actuator assembly including a plurality of actuators;

a visual indicator to guide the user where to place the hand-held portion;

a control system coupled to the plurality of actuators and the visual indicator, the control system being configured to:

determine a position or orientation of the hand-held portion in a first degree of freedom in a known coordinate system;

determine a theoretical range of motion of the hand-held portion relative to the tool support in a second degree of freedom based on the position or orientation of the hand-held portion in the first degree of freedom;

determine a position or orientation of the hand-held portion in the second degree of freedom in the known coordinate system; and control the visual indicator based on the position or orientation of the hand-held portion and the theoretical range of motion in the second degree of freedom to guide the user as to where to move the hand-held portion to provide the instrument with maximum adjustability of the plurality of actuators.

2. The hand-held robotic system of claim 1, wherein the control system is further configured to determine a theoretical range of motion of the hand-held portion relative to the tool support in a third degree of freedom based on the position or orientation of the hand-held portion in a first degree of freedom, determine a position or orientation of the hand-held portion in the third degree of freedom in the known coordinate system, and control the visual indicator based on the position or orientation of the hand-held portion and the theoretical range of motion in the second degree of freedom and based on the position or orientation of the hand-held portion and the theoretical range of motion in the third degree of freedom.

3. The hand-held robotic system of claim 2, wherein the control system is further configured to determine the theoretical range of motion of the tool support in the second degree of freedom based on the position or orientation of the hand-held portion in the first degree of freedom and based on a Cartesian model representing a three-dimensional workspace of the tool support relative to the hand-held portion.

4. The hand-held robotic system of claim 3, wherein the model is defined a plurality of roll values, pitch values, and elevation values.

5. The hand-held robotic system of claim 3, wherein the model representing the three-dimensional workspace of the tool support is derived from empirical data.

6. The hand-held robotic system of claim 3, wherein the control system is further configured to determine an actual deviation vector in a polar coordinate system that represents a two-dimensional area corresponding to a height value of the pose of the hand-held portion as the theoretical range of motion of the hand-held portion based on the orientation of the hand-held portion in the second degree of freedom and the orientation of the hand-held portion in the third degree of freedom, the actual deviation vector having a magnitude and a direction, and wherein the control system is configured to control the visual indicator based on the magnitude of the actual deviation vector, the direction of the actual deviation vector, or combinations thereof.

7. The hand-held robotic system of claim 6, wherein the Cartesian model includes a plurality of two-dimensional regions, each region surrounding its own origin, the actual deviation vector extending from the origin of at least one of the plurality of two-dimensional regions to a point defined in a polar coordinate system by the orientation of the hand-held portion in the second degree of freedom and the orientation of the hand-held portion in a third degree of freedom.

8. The hand-held robotic system of claim 7, wherein each of the plurality of two-dimensional regions is defined by plurality of roll values and a plurality of pitch values.

9. The hand-held robotic system of claim 8, wherein the control system is further configured to determine a range of motion vector in the polar coordinate system based on the position of the hand-held portion in the first degree of freedom, the range of motion vector having a magnitude, the range of motion vector extending from the origin of at least one of the plurality of two-dimensional regions to a boundary points of the two-dimensional region, wherein the control system is configured to control the visual indicator based on the magnitude of the actual deviation vector, the magnitude of the range of motion vector, the direction of the actual deviation vector combinations thereof.

10. The hand-held robotic system of claim 9, wherein the direction of the actual deviation vector and the direction of the range of motion vector are equal to one another, and the origin of the actual deviation vector is the same as the origin of the range of motion vector.

11. The hand-held robotic system of claim 9, wherein the first degree of freedom is elevation, and the control system is configured to determine a boundary point of the two-dimensional region based on the position of the hand-held portion in the first degree of freedom.

12. The hand-held robotic system of claim 11, wherein the control system is configured to determine the magnitude of the range of motion vector based on a pair of coordinates defining the boundary point of the two-dimensional region.

13. The hand-held robotic system of claim 12, wherein the two-dimensional region is asymmetrical about the origin.

14. The hand-held robotic system of claim 8, wherein the control system is configured to control the visual indicator based on the magnitude of the actual deviation vector and the magnitude of the range of motion vector.

15. The hand-held robotic system of claim 1, wherein the control system is configured to determine a pose of the hand-held portion in the known coordinate system, and the control system is configured to compute the position of the hand-held portion in the first degree of freedom and the position or orientation of the hand-held portion in the second degree of freedom based on the pose of the hand-held portion.

16. The hand-held robotic system of claim 15, wherein the pose of the hand-held portion is a commanded pose, a simulated commanded pose, a measured pose, a previous commanded pose, a previous measured pose, or combinations thereof.

17. The hand-held robotic system of claim 16, wherein the pose of the hand-held portion is a commanded pose, wherein the surgical tool is a saw blade, the tool support is defined as a blade support, and the saw blade is coupled to the blade support, wherein the commanded pose of the hand-held portion is a relationship between the saw blade and the hand-held portion.

18. The hand-held robotic system of claim 1, wherein the visual indicator is a display screen separate from the instrument.

19. The hand-held robotic system of claim 18, wherein the display screen is coupled to a navigation cart.

20. A hand-held robotic system for use with a surgical tool, the system comprising:

an instrument comprising;

a hand-held portion to be held by a user and a tool support coupled to the hand-held portion, the tool support comprising a tool drive motor to drive motion of the surgical tool; and an actuator assembly operatively interconnecting the tool support and the hand-held portion to move the tool support to move the tool in a plurality of degrees of freedom relative to the hand-held portion, the actuator assembly including a plurality of actuators;

a visual indicator to guide the user where to place the hand-held portion; and a control system coupled to the plurality of actuators and the visual indicator, the control system being configured to:

determine a first pose of the hand-held portion in a known coordinate system;

determine a first theoretical range of motion in a first degree of freedom based on a component of the first pose;

determine a second pose of the hand-held portion in the known coordinate system;

determine a second theoretical range of motion in the first degree of freedom based on a component of the second pose, wherein the first theoretical range of motion and the second theoretical range of motion are different and the first pose and the second pose are different;

determine a first position or orientation of the hand-held portion based on the first pose in the first degree of freedom and control the visual indicator based on the first position or orientation and the first range of motion; and determine a second position or orientation of the hand-held portion based on the second pose in the first degree of freedom and control the visual indicator based on the second position or orientation and the second range of motion to guide the user as to how to move the hand-held portion to provide the instrument with maximum adjustability of the plurality of actuators.

21. A method of controlling a visual indicia of a hand-held robotic system for use with a surgical tool, the robotic system including a localizer, and a hand-held instrument, the hand-held instrument having a hand-held portion to be held by a user, a tool support movably coupled to the hand-held portion to support the surgical tool, and an actuator assembly operatively interconnecting the tool support and the hand-held portion, the actuator assembly including a plurality of actuators, and the tool support including a saw drive motor, the method comprising the steps of:

the instrument controller determining a position or orientation of the hand-held portion in a first degree of freedom in a known coordinate system;

the instrument controller determining a theoretical range of motion of the hand-held portion relative to the tool support in a second degree of freedom based on the position or orientation of the hand-held portion in the first degree of freedom;

determining a position or orientation of the hand-held portion in the second degree of freedom in the known coordinate system; and the instrument controller controlling the visual indicator based on the position or orientation of the hand-held portion and the theoretical range of motion in the second degree of freedom to guide the user as to how to move the hand-held portion to provide the instrument with maximum adjustability of the plurality of actuators.

* * * * *